US008063101B2

(12) United States Patent
Lockwood et al.

(10) Patent No.: US 8,063,101 B2
(45) Date of Patent: Nov. 22, 2011

(54) CAROTENOID ANALOGS AND DERIVATIVES FOR THE PREVENTION OF PLATELET AGGREGATION

(75) Inventors: Samuel F. Lockwood, Lake Linden, MI (US); R. Preston Mason, Manchester, MA (US)

(73) Assignee: Cardax Pharmaceuticals, Inc., Honolulu, HI (US)

( * ) Notice: Subject to any disclaimer, the term of this patent is extended or adjusted under 35 U.S.C. 154(b) by 887 days.

(21) Appl. No.: 12/079,253

(22) Filed: Mar. 24, 2008

(65) Prior Publication Data

US 2009/0124574 A1    May 14, 2009

Related U.S. Application Data

(60) Provisional application No. 60/919,637, filed on Mar. 23, 2007, provisional application No. 60/948,787, filed on Jul. 10, 2007.

(51) Int. Cl.
*A61K 31/335*    (2006.01)
*C07C 403/24*    (2006.01)
(52) U.S. Cl. .................................. 514/460; 585/351
(58) Field of Classification Search .................. 514/460; 585/351
See application file for complete search history.

(56) References Cited

U.S. PATENT DOCUMENTS

| | | |
|---|---|---|
| 2,768,198 A | 10/1956 | Marbet |
| 3,206,316 A | 9/1965 | Klaui |
| 3,788,468 A | 1/1974 | Gainer |
| 3,853,993 A | 12/1974 | Gainer |
| 3,975,445 A | 8/1976 | Kienzle et al. |
| 4,156,090 A | 5/1979 | Kienzle |
| 4,851,339 A | 7/1989 | Hills |
| 5,605,699 A | 2/1997 | Bernhard et al. |
| 6,271,408 B1 | 8/2001 | Pfander et al. |
| 6,540,654 B2 | 4/2003 | Levy et al. |
| 2002/0051998 A1 | 5/2002 | Schmidt-Dannert et al. |
| 2002/0169334 A1 | 11/2002 | Levy et al. |
| 2003/0100045 A1 | 5/2003 | Cheng et al. |
| 2003/0182687 A1 | 9/2003 | Cheng et al. |
| 2004/0110849 A1 | 6/2004 | Zelkha et al. |
| 2006/0058269 A1 | 3/2006 | Lockwood et al. |
| 2006/0088904 A1 | 4/2006 | Lockwood et al. |
| 2006/0088905 A1 | 4/2006 | Lockwood et al. |
| 2006/0111580 A1 | 5/2006 | Lockwood et al. |
| 2006/0155150 A1 | 7/2006 | Lockwood et al. |
| 2006/0167319 A1 | 7/2006 | Lockwood et al. |
| 2006/0178538 A1 | 8/2006 | Lockwood et al. |
| 2006/0183185 A1 | 8/2006 | Lockwood et al. |
| 2006/0183947 A1 | 8/2006 | Lockwood et al. |

FOREIGN PATENT DOCUMENTS

| | | |
|---|---|---|
| DE | 19950327 A | 4/2000 |
| EP | 0542632 | 5/1993 |
| JP | 2000-143688 | 5/2000 |
| WO | WO 96/40092 | 12/1996 |

OTHER PUBLICATIONS

Foss et al. "Natural Occurrence of Enantiomeric and Meso Astaxanthin. 7. Crustaceans Including Zooplankton" Comp. Biochem. Physiol. B Comp. Biochem. (1987) 86: 313-314.
Fuhrhop et al. "Bolaform Amphiphiles with a Rigid Hydrophobic Bixin Core in Surface Monolayers and Lipid Membranes" Langmuir (1990) 6, 497-505.
Gabrielska et al. "Zeaxanthin (dihydroxy-B-carotene) but not B-Carotene Rigidifies Lipid Membranres: a 1H-NMR Study of Carotenoid-Egg Phosphatidylcholine Liposomes" Biochim. Biophys. Acta (1996) 1285, 167.
Gartner et al. "Preferential Increase in Chylomicron Levels of the Xanthophylls Lutein and Zeaxanthin Compared to B-Carotene in the Human" Int. J. Vitam. Nutr. Res. (1996) 66, 119.
Furr et al. "Intestinal Absorption and Tissue Distribution of Carotenoids" Nutritional Biochemistry (1997) 8, 364.
Gartner et al. "Lycopene is More Bioavailable from Tomato Paste than from Fresh Tomatoes." Am. J. Clin. Nutr. (1997) 66: 116-122.
Clark et al. "A Comparison of Lycopene and Astaxanthin Absorption From Corn Oil and Olive Oil Emulsions" Lipids (2000) 35(7), 803-806.
Frank et al. "Effect of the Solvent Environment on the Spectroscopic Properties and Dynamics of the Lowest Excited States of Carotenoids" J. Phys. Chem. B (2000) 104 , 4569-4577.
Bodor et al."Drug Targeting by Retrometabolic Design: Soft Drugs and Chemical Delivery Systems" J. Recept. Signal Transduct. Res. (2001) 21: 287-310.
Buchwald et al. "Physicochemical Aspects of the Enzymatic Hydrolysis of Carboxylic Esters." Phamiazie (2002) 57 (2), 87-93.
Zechmeister "Cis-Trans Isomerization and Stereochemistry of Carotenoids and Diphenylpolyenes" Chem. Rev. 34 (1944) 267-344.
Karrer et al. in "Carotenoids, Special Part: XIII. Carotenoid Carboxylic Acids 1. Bixin" Elsevier, New York—Amsterdam—London—Brussels (1950) 256-271.
Robinson "Lysolecithin" Pharm. Pharmacol. (1961) 13, 321.
Markham et al. "Carotenoids of Higher Plants I. The Structures of Lycoxanthin and Lycophyll" Phytochemistry (1968) 7, 839.
Isler in "Carotenoids" Isler, O., Ed.; Birkhäuser: Basel, 1971; 11-28.

(Continued)

*Primary Examiner* — Taofiq A Solola
(74) *Attorney, Agent, or Firm* — Meyertons, Hood, Kivlin, Kowert & Goetzel, P.C.; Eric B. Meyertons

(57) ABSTRACT

The presently described embodiments are directed to compositions that include one or more carotenoid analogs or derivatives for use in the treatment of a disorder associated with platelet aggregation. Certain embodiments provide for the use of said carotenoid analogs or derivatives in preparing compositions suitable for use in such treatments. Further embodiments provide for pharmaceutical compositions that include one or more carotenoid analogs or derivatives in combination with one or more additional compositions or medicaments suitable for the treatment of a disorder associated with platelet aggregation. Yet further embodiments provide for methods of treating a disorder associated with platelet aggregation that include administering to a subject who would benefit from such treatment pharmaceutical compositions suitable for inhibiting platelet aggregation in a subject undergoing said treatments, and that include carotenoid analogs or derivatives, optionally in combination with one or more additional antiplatelet agents.

23 Claims, 21 Drawing Sheets

OTHER PUBLICATIONS

Kelly et al. "Carotenoids of Higher Plants. 4. The Stereochemistry of Lycoxanthin and Lycophyll" Chem. Scand., Ser. A (1971) 25, 1607.

Weedon In Carotenoids; Isler, O., Ed.; Birkhäuser: Basel, 1971; pp. 29-59.

Pfander et al. "Synthese von neuen Carotinoid-Glycosylestern" Chimia (1980) 34, 20.

Lindig et al. "Rate Parameters for the Quenching of Singlet Oxygen by Water-Soluble and Lipid-Soluble Substrates in Aqueous and Micellar Systems" Photochem. Photobiol. (1981) 33, 627.

Hertzberg et al. "Carotenoid sulfates. 4. Synthesis and Properties of Carotenoid Sulfates" Acta Chemica Scandinavica B (1985) 39, 629-638.

Milon et al. "Organization of Carotenoid-Phospholipid Bilayer Systems. Incorporation of Zeaxanthin, Astaxanthin, and their C50 Homologues into Dimyristoylphosphatidylcholine Vesicles" Helv. Chim. Acta (1986) 69:12-24.

Di Mascio et al. "Lycopene as the Most Efficient Biological Carotenoid Singlet Oxygen Quencher" Arch. Biochem. Biophys. (1989) 274, 532.

Torrissen et al. "Pigmentation of Salmonids—Carotenoid Deposition and Metabolism" CRC Crit. Rev. Aquat. Sci. (1989) 1: 209-225.

Lee et al. "Effects, Quenching Mechanisms, and Kinetics of Carotenoids in Chlorophyll-Sensitized Photooxidation of Soybean Oil" J. Agric. Food Chem. (1990) 38, 1630.

Speranza et al. "Interaction Between Singlet Oxygen and Biologically Active Compounds in Aqueous Solution. III. Physical and Chemical Singlet Oxygen Quenching Rate Constants of 6,6-diapocarotenoids." (1990) J. Photochem. Photobiol. B8, 51-61.

Mathews-Roth "Recent Progress in the Medical Applications of Carotenoids" Pure Appl. Chem (1991) 63, 147-156.

Beecher et al. "Qualitative Relationship of Dietary and Plasma Carotenoids in Human Beings" Ann NY Acad Sci (1992) 669: 320-321.

Devasagayam et al. "Synthetic Carotenoids, Novel Polyene Polyketones and New Capsorubin Isomers as Efficient Quenchers of Singlet Molecular Oxygen" Photochem. Photobiol. (1992) 55:511-514.

Khachik et al. "Separation and Quantification of Carotenoids in Human Plasma" in "Carotenoids. Part A. Chemistry, separation, quantitation, and antioxidation" Packer L, editor.; San Diego: Academic Press, Inc., (1992) 205-219.

Ames et al. "DNA Lesions, Inducible DNA Repair, and Cell Division: Three Key Factors in Mutagenesis and Carcinogenesis" Environ Health Perspect (1993) 101 (Suppl. 5): 35-44.

Blanchard-Desce et al. "Caroviologens. Synthesis and Optical Properties of A,O-bis-Pyridine and A-O-bis-Pyridinium Polyenes" Bull. Soc. Chim. Fr. (1993) 130, 266-272.

Jyonouchi et al. "Studies of Immunomodulating Actions of Carotenoids. II. Astaxanthin Enhances in vitro Antibody Production to T-dependent Antigens without Facilitating Polyclonal B-cell Activation" Nutr. Cancer (1993) 19, 269-280.

Hirayama et al. "Singlet Oxygen Quenchiing Ability of Naturally Occurring Carotenes" Lipids (1994) 29, 149.

Koga et al. "Synthesis of Phosphatidyl Derivative of Vitamin E and its Antioxidant Activity in Phospholipid Bilayers" Lipids (1994) 29, 83.

Olson "Absorption, Transport, and Metabolism of Carotenoids in Humans" Pure & Applied Chemistry (1994) 66, 1011.

Jyonouchi et al. "Astaxanthin, a Carotenoid Without Vitamin A Activity, Augments Antibody Responses in Cultures Including T-Helper Cell Clones and Suboptimal Doses of Antigen" J. Nutr. (1995) 125, 2483-2492.

Meyer Vol. 1A: Isolation and Analysis; Britton, G.; Liaaen-Jensen, S.; Pfander, H., Eds.; Birkhäuser: Basel, (1995) pp. 277-282.

Frank et al. "Carotenoids in Photosynthesis" Photochem. Photobiol. (1996) 63: 257-264.

Kelly et al. "NMR, MS, and X-Ray Crystal Structure Determination of the Bixin Family of Apocarotenoids" J. Chem. Res. (M) (1996) 2637-2645.

Koepke et al. "The Crystal Structure of the Light-Harvesting Complex II (B800-850) from Rhodospirillum Molischianum" Structure (1996) 4,581-597.

Mori et al. "Bistable Aggregate of all-Trans-Astaxanthin in an Aqueous Solution" Chem. Phys. Lett. (1996) 254,84-88.

Olson "Beneftis and Liabilities of Vitamin A and Carotenoids" J. Nutr. (1996) 126: 1208S-1212S.

Partali et al. "Stable, Highly Unsaturated Glycerides—Enzymatic Synthesis with a Carotenoic Acid" Angew. Chem. Int. Ed. (1996) 35,329-330.

Van Vliet "Absorption of B-Carotene and Other Carotenoids in Humans and Animal Models" Eur. J. Clin. Nutr. (1996) 50 Suppl 3, S32.

Halliwell "Antioxidants and Human Disease: A general Introduction" Nutr. Rev. (1997) 55,544-552.

Levy et al. "Plasma Antioxidants and Lipid Peroxidation in Acute Myocardial Infarction and Thrombolysis" Analyst (1997) 122 977-980.

Pfander et al. "Carotenoid Synthesis: A Progress Report" Pure Appl. Chem. (1997) 69,2047.

Beckman et al. "The Free Radical Theory of Aging Matures" Physiol Rev. (1998) 78,547-581.

Koga et al. "Protective Effect of a Vitamin E Analogue, Phophatidylchromanol, Against Oxidative Hemolysis of Human Erythrocytes" J. Lipids (1998) 33, 589.

Krinsky "The Antioxidant and Biological Properties of the Carotenoids" Ann. N. Y. Acad. Sci. (1998) 854, 443.

Russell "Pysiological and Clinical Significance of Carotenoids" Int. J. Vitam. Nutr. Res. (1998) 68, 349.

Mercadante, A. "New carotenoids: Recent Progress" Pure Appl. Chem., (1999) vol. 71, No. 12, 2263-2272.

Olson "Bioavailability of Carotenoids" Arch. Latinoam. Nutr. (1999) 49, 21S-25S.

Ruttimann "Dienolether Condensations—a Powerful Tool in Carotenoid Synthesis" Pure Appl. Chem. (1999) 71, 2285.

Yuan et al. "Hydrolysis Kinetics of Astaxanthin Esters and Stability of Astaxanthin of Haematococcus Pluvialis During Saponification" J. Agric. Food Chem. (1999) 47, 31.

Yuan et al. "Isomerization of trans-Astaxanthin to cis-Isomers in Organic Solvents" J. Agric. Food Chem. (1999) 47, 3656.

Baroli et al. "Molecular Genetics of Xanthophylldependent Photoprotection in Green Algae and Plants" Philos. Trans. R. Soc. Lond. B Biol. Sci. (2000) 355, 1385-1394.

Bell et al. "Depletion of alpha-Tocopherol and Astaxanthin in Atlantic Salmon (Salmo salar) Affects Autoxidative Defense and Fatty Acid Metabolism" J. Nutr. (2000) 130, 1800-1808.

Neveu et al. "Gap Junctions and Neoplasia" in: E.L. Hertzberg, E.E. Bittar (Eds.), Gap Junctions, JAI Press, Greenwich, CT, (2000) pp. 221-262.

Tahir et al. "Regio- and Chemoselective Alkylation of L-Ascorbic Acid under Mitsunobu Conditions" J. Org. Chem. (2000) 65(3), 911-913.

Beutner et al. "Quantitative Assessment of Antioxidant Properties of Natural Colorants and Phytochemicals: Carotenoids, Avonoids, Phenols and Indigoids. The Role of b-Carotene in Antioxidant Functions" J Sci Food Agric. (2001) 81, 559-568.

Hakimelahi et al. "Synthesis and Biological Evaluation of Purine-Containing Butenolides" J. Med. Chem. (2001) 44 (11) 1749-1757.

Horn et al. "Organic Nanoparticles in the Aqueous Phase—Theory, Experiment, and Use" Angew. Chem., Int. Ed. Engl. (2001) 40, 4330-4361.

Kiefer et al. "Identification and Characterization of a Mammalian Enzyme Catalyzing the Asymmetric Oxidative Cleavage of Provitamin" A. J. Biol. Chem. (2001) 276: 14110-14116.

Mortensen et al. "The Interaction of Dietary Carotenoids with Radical Species" Arch Biochem Biophys (2001) 385:13-19.

Shibata et al. "Molecular Characteristics of Astaxanthin and B-Carotene in the Phospholipid Monolayer and Their Distributions in the Phospholipid Bilayer" Chem. Phys. Lipids (2001) 113, 11-22.

Sugarawa et al. "Lysophosphatidylcholine Enhances Carotenoid Uptake from Mixed Micelles by Caco-2 Human Intestinal Cells" J. Nutr. (2001) 131, 2921.

Yanishlieva et al. "B-Apo-8'-Carotenoic Acid and its Derivatives" J. Am. Oil Chem. Soc. (2001) 78, 641-644.

Wang et al. "A Quantum Chemistry Study of Binding Carotenoids in the Bacterial Light-Harvesting Complexes" J. Am. Chem. Soc. (2002) 124, 8445-8451.

Zaripheh et al. "Factors That Influence the Bioavailablity of Xanthophylls" J. Nutr. (2002) 132, 531S.

Cholnoky et al. "The Structure of Lycoxanthin and Lycophyll" Tetrahedron Lett. (1968) 16, 1931.

Davis et al. "Reconstitution of the Bacterial Core Light-Harvesting Complexes of Rhodobacter sphaeroides and Rhodospirillumrubrum with Isolated a- and b-Polypeptides, Bacteriochlorophyll a, and Carotenoid" J. Biol. Chem. (1995) 270, 5793-5804.

Froescheis et al. "Determination of Lycopene in Tissues and Plasma of Rats by Normal-Phase High-Performance Liquid Chromatography With Photometric Detection" J. Chromatogr. B Biomed. Sci. Appl. (2000) 739, 291.

Zsila, F., et al, "Color and chirality: carotenoid self-assemblies in flower petals," Planta 213, (2001), pp. 937-942.

Britton, G., et al., "Carotenoids: Isolation and Analysis," Birkhauser: Basel, vol. la, (1995), p. 82.

Boileau et al. "Bioavailability of all-Trans and cis-Isomers of Lycopene" Exp. Biol. Med. (Maywood) (2002) 227, 914-919.

Jyonouchi et al. "Studies of Immunomodulating Actions of Carotenoids. I. Effects of beta-Carotene and Astaxanthin on Murine Lymphocyte Functions and Cell Surface Marker Expression in in vitro Culture System" Nutr. Cancer (1991) 16: 93-105.

Subczynski, W., et al., "Effect of polar carotenoids on the oxygen diffusion-concentration product in lipid bilayers; An EPR spin label study," Biochim Biophys Acta, 1068, (1991), pp. 68-72.

Kjosen et al. "Carotenoids of Higher Plants 6. Total Synthesis of Lycoxanthin and Lycophyll" Acta. Chem. Scand. 26 (1972) 10 4121-4129.

Huang, D., et al., "Development and Validation of Oxygen Radical Absorbance Capacity Assay for Lipophilic Antioxidants Using Randomly Methylated beta-Cyclodextrin as the Solubility Enhancer" J Agric Food Chem.(2002) 50, 1815-1821.

Jensen, S., et al., "All-rac-alpha-tocopherol acetate is a better vitamin E source thasn all-rac-alpha-tocopherol succinate for broilers," J Nutr, 129: (1999), pp. 1355-1360.

Hara et al. "Stabilization of Liposomal Membranes by Thermozeaxanthins: Carotenoid-Glucoside Esters" Biochim. Biophys. Abst. (1999) 1461, 147-154.

Bowen et al. "Esterification Does Not Impair Lutein Bioavailability in Humans" J. Nutr. (2002) 32, 3668-3673.

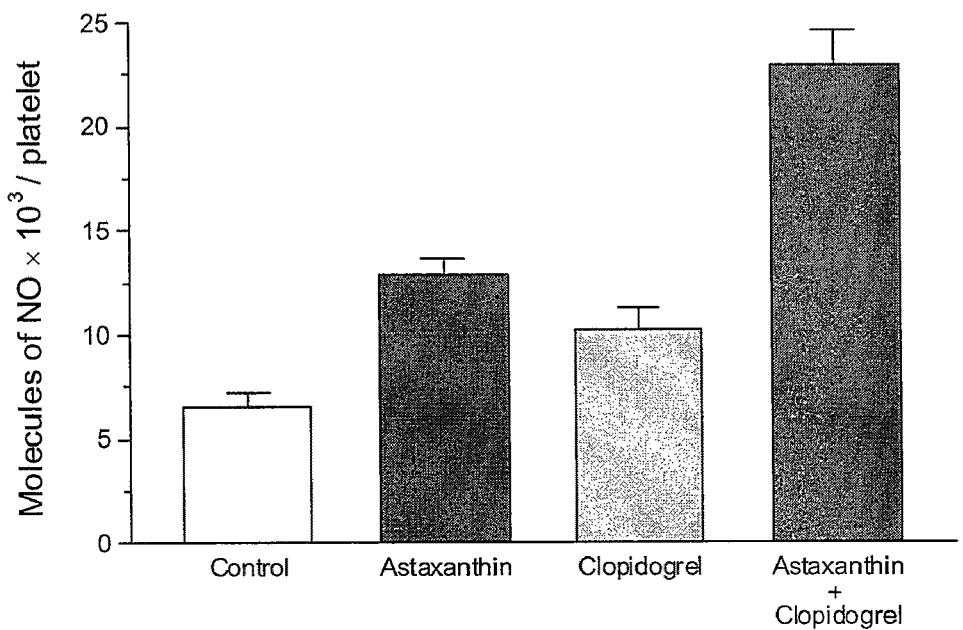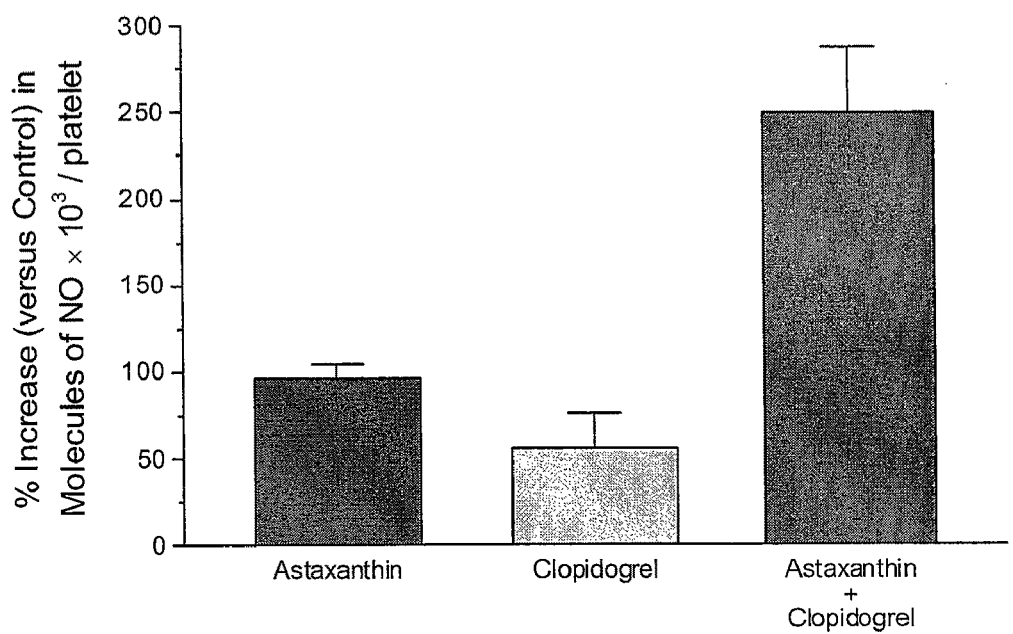
FIG. 3

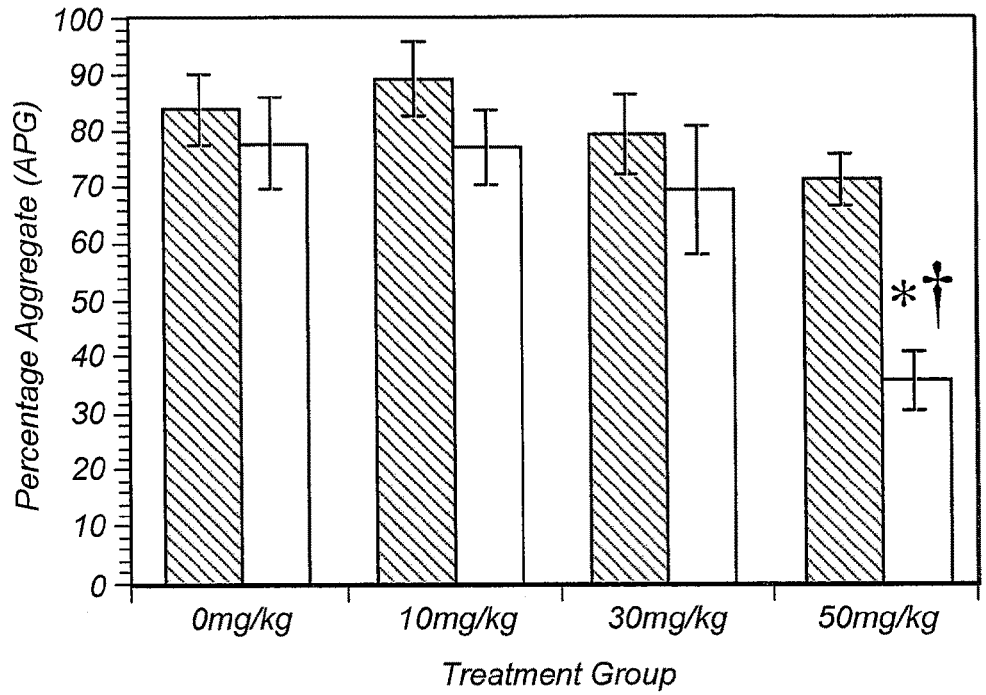
FIG. 8A
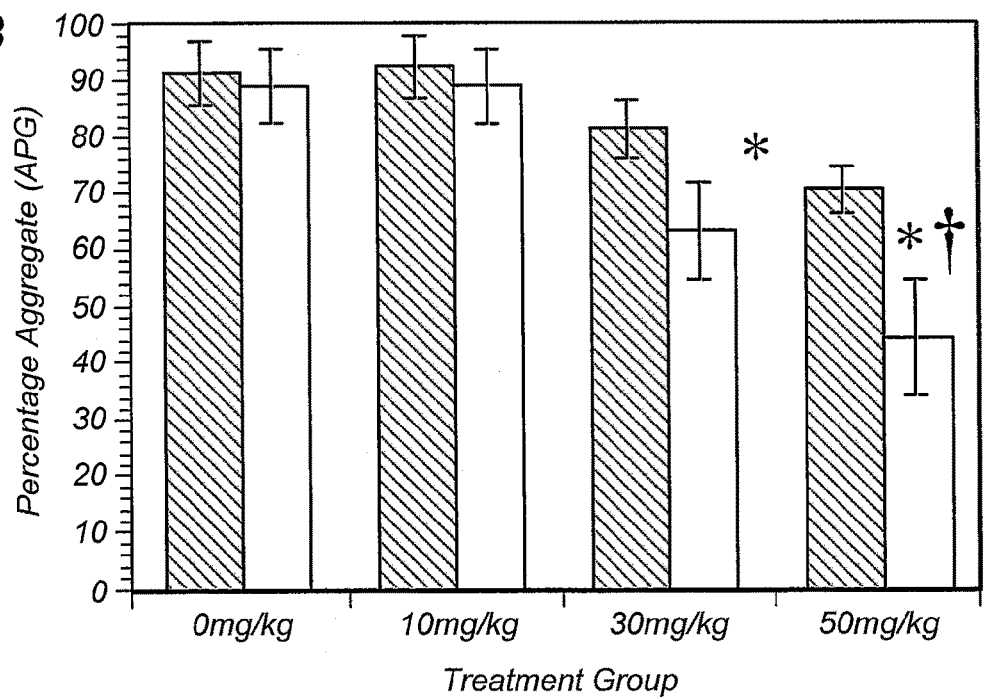
FIG. 8B
FIG. 8

PK Studies

| PK Study | Species | Test article | Formulation | Route | Dose | Frequency | Number |
|---|---|---|---|---|---|---|---|
| CXPK07201 | Rat | ADL | Lipid suspension | PO | 500 mg/kg | Single | n = 10 |
| | | ADS | Lipid suspension | PO | 500 mg/kg | Single | n = 10 |
| | | Asta | Lipid suspension | PO | 500 mg/kg | Single | n = 10 |
| CXPK07202 | Rat | ADG | Water | IV | 5 mg/kg | Single | n = 3 |
| | | ADSa | Water | IV | 5 mg/kg | Single | n = 3 |
| | | ADL | Water | IV | 5 mg/kg | Single | n = 3 |
| | | ADG | Aqueous suspension, 0.5% CMC | PO | 40 mg/kg | Single | n = 3 |
| | | ADSa | Aqueous suspension, 0.5% CMC | PO | 40 mg/kg | Single | n = 3 |
| | | ADL | Aqueous suspension, 0.5% CMC | PO | 40 mg/kg | Single | n = 3 |
| CXPK07402 | Beagle dog (non-naïve) | ADL | Saline | IV | 5 mg/kg | Single | n = 3 |
| | | ADL | Aqueous suspension, 0.5% CMC | PO | 10 mg/kg | Single | n = 3 |
| | | ADL | Aqueous suspension, 0.5% CMC | PO | 100 mg/kg | Single | n = 3 |
| | | ADL | Aqueous suspension, 0.5% CMC | PO | 500 mg/kg | Single | n = 3 |
| CXPK07404 | Beagle dog (naïve) | ADL | Aqueous suspension, 0.5% CMC | PO | 75 mg/kg | bid × 6 days | n = 3 |
| CXPK07405 | Beagle dog (non-naïve) | ADG | Aqueous suspension, 0.5% CMC | PO | 20 mg/kg | Single | n = 3 |
| | | ADL | Aqueous suspension, 0.5% CMC | PO | 20 mg/kg | Single | n = 3 |
| | | ADSa | Aqueous suspension, 0.5% CMC | PO | 20 mg/kg | Single | n = 3 |
| | | ADA | Aqueous suspension, 0.5% CMC | PO | 20 mg/kg | Single | n = 3 |
| | | ADS | Aqueous suspension, 0.5% CMC | PO | 20 mg/kg | Single | n = 3 |
| CXPK07406 | Beagle dog (non-naïve) | ADG | Aqueous suspension, 0.5% CMC | PO | 50 mg/kg | Single | n = 3 |
| | | ADG | Aqueous suspension, 0.5% CMC | PO | 100 mg/kg | Single | n = 3 |
| | | ADSa | Aqueous suspension, 0.5% CMC | PO | 50 mg/kg | Single | n = 3 |
| | | ADSa | Aqueous suspension, 0.5% CMC | PO | 100 mg/kg | Single | n = 3 |
| CXPK07502 | Monkey (non-naïve) | ADSa | Water | IV | 5 mg/kg | Single | n = 3 |
| | | ADSa | Aqueous suspension, 0.5% CMC | PO | 10 mg/kg | Single | n = 3 |
| | | ADSa | Aqueous suspension, 0.5% CMC | PO | 500 mg/kg | Single | n = 3 |
| | | ADSa | Aqueous suspension, 0.5% CMC | PO | 500 mg/kg | Single | n = 3 |

ADSa = all-trans 3S,3'S-astaxanthin diester disarcosinate dihydrochloride salt
ADG = all-trans 3S,3'S-astaxanthin diester digiyoinate dihydrochloride salt
ADL = all-trans 3S,3'S-astaxanthin diester dilysinate tetrahydrochloride salt
ADA = all-trans 3S,3'S-astaxanthin diester di-beta-alanine dihydrochloride salt
ADS = all-trans 3S,3'S-astaxanthin diester disuccinate disodium salt
Asta = all-trans 3S,3'S-astaxanthin CMC = carboxymethylcellulose

*FIG. 20*

PK Study – CXPK07202

Astaxanthin following administration of ADG, ADSa, ADL in rats

| Total Asta | ADG IV 5 mg/kg | ADG PO 40 mg/kg | ADSa IV 5 mg/kg | ADSa PO 40 mg/kg | ADL IV 5 mg/kg | ADL PO 40 mg/kg |
|---|---|---|---|---|---|---|
| $T_{max}$ (hr) | 6.0 ± 2.0 | 6.7 ± 1.2 | 4.7 ± 1.2 | 5.3 ± 1.2 | 3.5 ± 0.8 | 5.3 ± 1.2 |
| $C_{max}$ (µg/ml) | 5.0 ± 0.3 | 4.8 ± 2.2 | 1.9 ± 1.0 | 1.5 ± 0.5 | 1.8 ± 0.2 | 3.2 ± 0.6 |
| AUC (µg·hr/ml) | 124.0 ± 14.9 | 37.4 ± 11.9 | 73.8 ± 44.9 | 9.6 ± 1.7 | 63.1 ± 12.0 | 23.8 ± 5.1 |
| F (%) | - | 4 | - | 2 | - | 4 |
| T ½ (hr) | (20.2 ± 3.7) | 6.9 ± 2.7 | (22.1 ± 3.1) | 4.2 ± 2.4 | (24.4 ± 5.4) | 6.5 ± 1.9 |

| Trans Asta | ADG IV 5 mg/kg | ADG PO 40 mg/kg | ADSa IV 5 mg/kg | ADSa PO 40 mg/kg | ADL IV 5 mg/kg | ADL PO 40 mg/kg |
|---|---|---|---|---|---|---|
| $T_{max}$ (hr) | 11.3 ± 11.0 | 7.3 ± 1.2 | 4.7 ± 1.2 | 4.0 ± 2.0 | 0.7 ± 0.3 | 4.7 ± 1.2 |
| $C_{max}$ (µg/ml) | 0.9 ± 0.2 | 1.4 ± 0.3 | 1.3 ± 0.7 | 0.9 ± 0.6 | 1.0 ± 0.1 | 1.4 ± 0.2 |
| AUC (µg·hr/ml) | 37.4 ± 6.8 | 11.4 ± 3.2 | 52.4 ± 36.3 | 5.3 ± 1.9 | 28.5 ± 5.8 | 9.6 ± 2.3 |
| T ½ (hr) | (24.1 ± 1.3) | 8.0 ± 2.4 | (19.6 ± 2.4) | 4.1 ± 2.5 | (24.0 ± 2.6) | 6.0 ± 1.2 |

| Cis Asta | ADG IV 5 mg/kg | ADG PO 40 mg/kg | ADSa IV 5 mg/kg | ADSa PO 40 mg/kg | ADL IV 5 mg/kg | ADL PO 40 mg/kg |
|---|---|---|---|---|---|---|
| $T_{max}$ (hr) | 6.0 ± 2.0 | 6.7 ± 1.2 | 4.0 ± 2.0 | 5.3 ± 1.2 | 6.7 ± 4.6 | 5.3 ± 1.2 |
| $C_{max}$ (µg/ml) | 4.3 ± 0.3 | 3.5 ± 2.1 | 0.6 ± 0.3 | 1.5 ± 0.5 | 1.0 ± 0.2 | 1.8 ± 0.3 |
| AUC (µg·hr/ml) | 85.8 ± 7.9 | 25.8 ± 8.6 | 20.6 ± 8.9 | 9.6 ± 1.7 | 34.1 ± 8.8 | 14.3 ± 2.5 |
| T ½ (hr) | (20.8 ± 2.1) | 7.6 ± 3.6 | (26.0 ± 3.7) | 4.2 ± 2.4 | (22.4 ± 4.5) | 7.9 ± 1.7 |

FIG. 22

PK Study – CXPK07402

Total Astaxanthin following administration of ADL in dogs

| | IV 5 mg/kg** | PO 10 mg/kg | PO 100 mg/kg* | PO 500 mg/kg* |
|---|---|---|---|---|
| $T_{max}$ (hr) | 5.0 ± 1.4 | 3.3 ± 1.2 | 5.0 ± 1.4 | 5.0 ± 1.4 |
| $C_{max}$ (ng/mL) | 123 ± 28 | 106 ± 67 | (260 ± 19) | (1653 ± 959) |
| $C_{max}/D$ | 25 ± 6 | 10.6 ± 6.7 | (2.6 ± 0.2) | (3.3 ± 1.9) |
| AUC (ng·hr/mL) | 4377 ± 36 | 1104 ± 353 | (3111 ± 144) | (11809 ± 6856) |
| AUC/D | 875 ± 7 | 110 ± 35 | (31 ± 1.0) | (24 ± 14) |
| F (%) | – | 13 | (4) | (3) |
| CL (ml/min/kg) | 19 ± 0.2 | 161 ± 45 | (536 ± 25) | (849 ± 493) |
| V (L/kg) | 62 ± 3 | 160 ± 51 | (432 ± 85) | (1317 ± 262) |
| $T_{½}$ (hr) | 37.5 ± 2.0 | 11.4 ± 1.2 | 9.3 ± 1.4 | (20.3 ± 8.2) |

*: the animals didn't receive the full dose due to the emesis n=2
**: n=2

*FIG. 23*

PK Study – CXPK07404

Astaxanthin following administration of ADL in dogs

Total Asta (ng/g)

| Tissues | Day 1 | SD | Day 3 | SD | Day 5 | SD |
|---|---|---|---|---|---|---|
| Liver | 706 | 707 | 2315 | 2190 | 3801 | 1911 |
| Brain | 16 | 22 | 49 | 20 | 19 | 8 |
| Heart | 378 | 18 | 12524 | 661 | 20637 | 897 |
| Plasma | 1095 | 714 | 3930 | 1584 | 7030 | 1613 |

Trans Asta (ng/g)

| Tissues | Day 1 | SD | Day 3 | SD | Day 5 | SD |
|---|---|---|---|---|---|---|
| Liver | 632 | 631 | 1948 | 1800 | 3217 | 1438 |
| Brain | 16 | 22 | 47 | 17 | 19 | 8 |
| Heart | 378 | 18 | 11547 | 619 | 19075 | 812 |
| Plasma | 502 | 322 | 1730 | 622 | 2800 | 467 |

Cis Asta (ng/g)

| Tissues | Day 1 | SD | Day 3 | SD | Day 5 | SD |
|---|---|---|---|---|---|---|
| Liver | 74 | 76 | 368 | 391 | 584 | 473 |
| Brain | ND | ND | 2 | 3 | ND | ND |
| Heart | ND | ND | 977 | 72 | 1562 | 95 |
| Plasma | 593 | 392 | 2200 | 962 | 4230 | 1146 |

FIG. 24

PK Study – CXPK07406

Total Astaxanthin following administration of ADG and ADSa in dogs

| Total Asta | ADG 50 mg/kg | ADG 100 mg/kg | ADSa 50 mg/kg | ADSa 100 mg/kg |
|---|---|---|---|---|
| $T_{max}$ (hr) | 6.7 ± 1.2 | 5.3 ± 1.2 | 8.7 ± 3.1 | 5.0 ± 1.4* |
| $C_{max}$ (µg/ml) | 12.2 ± 7.2 | 16.0 ± 7.7 | 1.7 ± 1.9 | 4.8 ± 4.7 |
| AUC (µg•hr/ml) | 170.3 ± 98.4 | 272.0 ± 103.0 | 27.1 ± 30.5 | 65.0 ± 57.9 |
| T ½ (hr) | 19.6 ± 6.1 | 19.3 ± 4.3 | 9.5 ± 2.9 | 9.6 ± 2.4 |

PK Study – CXPK07502

Astaxanthin following administration of ADSa in monkeys

| Total Asta | IV 5 mg/kg | PO 10 mg/kg | PO 300 mg/kg | PO 500 mg/kg |
|---|---|---|---|---|
| $T_{max}$ (hr) | 0.5 | 8 | 8 | 8 |
| $C_{max}$ (µg/ml) | 11.4 | 4.4 | 35.4 | 44.0 |
| AUC (µg·hr/ml) | 378.9 | 74.6 | 513.7 | 704.4 |
| F (%) | – | 10 | 3 | 2 |
| T ½ (hr) | 28 | 28 | 29 | 26 |

| Trans Asta | IV 5 mg/kg | PO 10 mg/kg | PO 300 mg/kg | PO 500 mg/kg |
|---|---|---|---|---|
| $T_{max}$ (hr) | 0.5 | 8 | 8 | 8 |
| $C_{max}$ (µg/ml) | 6.3 | 2.5 | 21.5 | 24.8 |
| AUC (µg·hr/ml) | 226.0 | 35.2 | 260.9 | 330.0 |
| F (%) | – | 5 | 1 | 1 |
| T ½ (hr) | 27 | 21 | 23 | 30 |

| Cis Asta | IV 5 mg/kg | PO 10 mg/kg | PO 300 mg/kg | PO 500 mg/kg |
|---|---|---|---|---|
| $T_{max}$ (hr) | 0.5 | 8 | 8 | 8 |
| $C_{max}$ (µg/ml) | 5.1 | 2.0 | 14.0 | 19.2 |
| AUC (µg·hr/ml) | 152.8 | 40.3 | 251.2 | 374.0 |
| F (%) | – | 5 | 1 | 1 |
| T ½ (hr) | 29 | 27 | 27 | 24 |

FIG. 27

CAROTENOID ANALOGS AND DERIVATIVES FOR THE PREVENTION OF PLATELET AGGREGATION

PRIORITY CLAIM

This application claims the benefit of priority under 35 U.S.C. 119(d)(e) to Provisional Patent Application Ser. No. 60/919,637, entitled "CAROTENOID ANALOGS AND DERIVATIVES FOR THE INHIBITION OF AGGREGATION" filed Mar. 23, 2007 and to Provisional Patent Application Ser. No. 60/948,787, entitled "CAROTENOID ANALOGS AND DERIVATIVES FOR THE PREVENTION OF PLATELET AGGREGATION," filed Jul. 10, 2007. The above-cited applications are commonly assigned with the present invention, and the entire contents thereof are incorporated by reference as though fully set forth herein.

BACKGROUND OF THE INVENTION

1. Field of the Invention

The present invention generally relates to the field of medicinal chemistry. More specifically, the present invention relates to the use of synthetic carotenoid analogs, derivatives and compositions made using same for the treatment and prevention of platelet aggregation and thrombus formation in a subject.

2. Description of the Relevant Art

Platelet accumulation at sites of vascular injury is a dynamic process that mediates formation of both the primary hemostatic plug and pathologic thrombus formation. The mechanisms by which platelet surface proteins direct platelet recruitment to thrombi under flow conditions have been studied in detail. In addition to directing initial platelet adhesion, cell-surface receptor interactions activate intracellular signaling. Intracellular signaling stimulates the release of thrombogenic substances from platelet granules. Signaling also mediates activation of the platelet integrin $\alpha_{IIb}\beta_3$ (gpIIb-IIIa) that facilitates firm adhesion of platelets to thrombi.

Arterial thrombosis mediates tissue infarction in coronary artery disease, cerebrovascular disease, and peripheral vascular disease, and, thus, is the single most common cause of morbidity and mortality in the United States. Platelets are key mediators of arterial thrombosis. Thus, the identification of compounds that inhibit platelet function is of great importance to medicine.

Platelets form the body's primary means of hemostasis and, as such, have developed an elaborate mechanism of surveying the vasculature for defects in endothelial integrity. This mechanism involves the ability to respond to subendothelial matrices, shear forces, neighboring platelets, the adrenal axis, as well as soluble proteinacious, nucleotide, and lipid signals. Despite this plethora of physiologic activators, the platelet has only a small repertoire of major functional outputs. Upon activation, platelets change shape, aggregate, and secrete their granular contents. The process of platelet activation involves the expression of activities not shared by functionally merit resting platelets, including, for example, ATP release, serotonin release, lysosomal release, alpha granule release, dense granule release, and cell surface expression of markers of activated platelets (including, but not limited to CD9, gpIb, gpIIb, gpIIIa, CDIa-IIa, P-selectin, PECAM-1, activated gpIIb/IIIa, and vitronectin receptor). In addition, platelet activation results in the aggregation of platelets with each other and with non-platelet surrounding cells. The granular contents of platelets supply additional adhesion molecules, growth factors, coagulation enzymes and other specialized molecules instrumental in the process of thrombus formation and the initiation of the healing process.

In addition to coronary artery disease/myocardial infarction, cerebrovascular disease and peripheral vascular disease, diseases and disorders associated with inappropriate platelet activity and arterial thrombosis also include, for example, stable and unstable angina, transient ischemic attacks, placental insufficiency, unwanted thromboses subsequent to surgical procedures (e.g., aortocoronary bypass surgery, angioplasty and stent placement, and heart valve replacement), or thromboses subsequent to atrial fibrillation. Inhibitors of platelet activity can provide therapeutic and preventive benefits for each of these diseases or disorders. It is also possible that inappropriate platelet activation plays a role in venous thrombosis, such that platelet inhibitors can be useful for the treatment or prevention of disorders associated with such thromboses.

A connection is emerging between platelet activation and inflammation, particularly allergic inflammation (e.g., in asthma) and inflammation at the sites of atherosclerotic damage. Therefore, compounds that inhibit platelet activation can also be useful in the treatment or prevention of disorders involving inflammation.

There are a number of agents presently available that target platelet function. For example, aspirin is a relatively weak platelet inhibitor. However, aspirin can cause life-threatening allergic reactions in sensitive individuals.

Another platelet inhibiting agent is ticlopidine (TICLID™, Roche Pharmaceuticals). Because it requires the production of active metabolites to be effective, the effect of ticlopidine is delayed 24-48 hours. The drug can also cause thrombotic thrombocytopenic purpura, a life-threatening condition, as well as nausea, abdominal pain, dyspepsia, diarrhea and skin rash.

Clodiprogel (PLAVIX™, Bristol-Meyers Squibb/Sanofi Pharmaceuticals) is another platelet inhibitor that requires the generation of active metabolites for its therapeutic efficacy. Therefore, clodiprogel also has a delay of 24-48 hours for its effect. Clodiprogel can also cause thrombotic thrombocytopenia purpura as well as agranulocytopenia, both life-threatening conditions. The drug has also been associated with rash, edema, hypertension, hypercholesterolemia, nausea, abdominal pain, dyspepsia, diarrhea, urinary tract infections, liver enzyme elevations and arthralgia.

The platelet inhibitory agents Abiximab and c7E3 Fab (REOPRO ABCIXIMAB™, manufacturer—Centocor B.V., distributor—Eli Lilly and Co.) are only available in a parenteral form. The drugs can cause severe thrombocytopenia. Both have a very long half-life and, therefore, complicate surgery that is sometimes required in the setting of life-threatening arterial occlusion (e.g., emergent cardiac surgery in the setting of a myocardial infarction).

Tirofiban (AGGRASTAT™, Merck and Co., Inc.) is another platelet inhibitory agent that is only available in a parenteral form. Tirofiban can cause thrombocytopenia, coronary artery dissection, bradycardia and edema, as well as dizziness and vasovagal reactions.

Eptifibatide (INTEGRILIN™, COR Therapeutics, Inc., Key Pharmaceuticals Inc.) is another platelet inhibitory agent that is only available for parenteral administration. It can cause hypotension.

There is only limited clinical experience with the oral anti-GPIIbIIIa agents lamifiban, sibrafiban, orofiban and xemilofiban. Similarly, clinical experience is limited with the phosphodiesterase inhibitors cilostazol, trapidil and trifusal.

There is more clinical experience with the phosphodiesterase inhibitor dipyridamole, but its activity is so weak that it is not frequently used.

There is a need in the art for additional platelet inhibitory agents for the treatment and prevention of diseases or disorders characterized by platelet activation and thrombosis. There is a need in the area of cardiovascular and cerebrovascular therapeutics for an agent that can be used in the prevention and treatment of thrombi, with minimal side effects, such as unwanted prolongation of bleeding, while preventing or treating target thrombi.

Antioxidant Properties of Carotenoids

Carotenoids are a group of natural pigments produced principally by plants, yeast, and microalgae. The family of related compounds now numbers greater than 750 described members, exclusive of Z and E isomers. Humans and other animals cannot synthesize carotenoids de novo and must obtain them from their diet. All carotenoids share common chemical features, such as a polyisoprenoid structure, a long polyene chain forming the chromophore, and near symmetry around the central double bond. Tail-to-tail linkage of two $C_{20}$ geranylgeranyl diphosphate molecules produces the parent $C_{40}$ carbon skeleton. Carotenoids without oxygenated functional groups are called "carotenes", reflecting their hydrocarbon nature; oxygenated carotenes are known as "xanthophylls." "Parent" carotenoids may generally refer to those natural compounds utilized as starting scaffold for structural carotenoid analog synthesis. Carotenoid derivatives may be derived from a naturally occurring carotenoid. Naturally occurring carotenoids may include lycopene, lycophyll, lycoxanthin, astaxanthin, beta-carotene, lutein, zeaxanthin, and/or canthaxanthin to name a few.

Cyclization at one or both ends of the molecule yields 7 identified end groups (illustrative structures shown in FIG. 1). Examples of uses of carotenoid derivatives and analogs are illustrated in U.S. patent application Ser. No. 10/793,671 filed on Mar. 4, 2004, entitled "CAROTENOID ETHER ANALOGS OR DERIVATIVES FOR THE INHIBITION AND AMELIORATION OF DISEASE" by Lockwood et al. published on Jan. 13, 2005, as Publication No. US-2005-0009758 and PCT International Application Number PCT/US2003/023706 filed on Jul. 29, 2003, entitled "STRUCTURAL CAROTENOID ANALOGS FOR THE INHIBITION AND AMELIORATION OF DISEASE" by Lockwood et al. (International Publication Number WO 2004/011423 A2, published on Feb. 5, 2004) both of which are incorporated by reference as though fully set forth herein.

Documented carotenoid functions in nature include light harvesting, photoprotection, and protective and sex-related coloration in microscopic organisms, mammals, and birds, respectively. A relatively recent observation has been the protective role of carotenoids against age-related diseases in humans as part of a complex antioxidant network within cells. This role is dictated by the close relationship between the physicochemical properties of individual carotenoids and their in vivo functions in organisms. The long system of alternating double and single bonds in the central part of the molecule (delocalizing the π-orbital electrons over the entire length of the polyene chain) confers the distinctive molecular shape, chemical reactivity, and light-absorbing properties of carotenoids. Additionally, isomerism around C=C double bonds yields distinctly different molecular structures that may be isolated as separate compounds (known as Z ("cis") and E ("trans"), or geometric, isomers). Of the more than 750 described carotenoids, an even greater number of the theoretically possible mono-Z and poly-Z isomers are sometimes encountered in nature. The presence of a Z double bond creates greater steric hindrance between nearby hydrogen atoms and/or methyl groups, so that Z isomers are generally less stable thermodynamically, and more chemically reactive, than the corresponding all-E form. The all-E configuration is an extended, linear, and rigid molecule. Z-isomers are, by contrast, not simple, linear molecules (the so-called "bent-chain" isomers). The presence of any Z in the polyene chain creates a bent-chain molecule. The tendency of Z-isomers to crystallize or aggregate is much less than all-E, and Z isomers are more readily solubilized, absorbed, and transported in vivo than their all-E counterparts. This has important implications for enteral (e.g., oral) and parenteral (e.g., intravenous, intra-arterial, intramuscular, and subcutaneous) dosing in mammals.

Carotenoids with chiral centers may exist either as the R (rectus) or S (sinister) configurations. As an example, astaxanthin (with 2 chiral centers at the 3 and 3' carbons) may exist as 4 possible stereoisomers: 3S, 3'S; 3R, 3'S and 3S, 3'R (identical meso forms); or 3R, 3'R. The relative proportions of each of the stereoisomers may vary by natural source. For example, *Haematococcus pluvialis* microalgal meal is 99% 3S, 3'S astaxanthin, and is likely the predominant human evolutionary source of astaxanthin. Krill (3R,3'R) and yeast sources yield different stereoisomer compositions than the microalgal source. Synthetic astaxanthin, produced by large manufacturers such as Hoffmann-LaRoche AG, Buckton Scott (USA), or BASF AG, are provided as defined geometric isomer mixtures of a 1:2:1 stereoisomer mixture [3S, 3'S; 3R, 3'S, 3'R,3S (meso); 3R, 3'R] of non-esterified, free astaxanthin. Natural source astaxanthin from salmonid fish is predominantly a single stereoisomer (3S,3'S), but does contain a mixture of geometric isomers. Astaxanthin from the natural source *Haematococcus pluvialis* may contain nearly 50% Z isomers. As stated above, the Z conformational change may lead to a higher steric interference between the two parts of the carotenoid molecule, rendering it less stable, more reactive, and more susceptible to reactivity at low oxygen tensions. In such a situation, in relation to the all-E form, the Z forms: (1) may be degraded first; (2) may better suppress the attack of cells by reactive oxygen species such as superoxide anion; and (3) may preferentially slow the formation of radicals. Overall, the Z forms may initially be thermodynamically favored to protect the lipophilic portions of the cell and the cell membrane from destruction. It is important to note, however, that the all-E form of astaxanthin, unlike β-carotene, retains significant oral bioavailability as well as antioxidant capacity in the form of its dihydroxy- and diketo-substitutions on the β-ionone rings, and has been demonstrated to have increased efficacy over β-carotene in most studies. The all-E form of astaxanthin has also been postulated to have the most membrane-stabilizing effect on cells in vivo. Therefore, it is likely that the all-E form of astaxanthin in natural and synthetic mixtures of stereoisomers is also extremely important in antioxidant mechanisms, and may be the form most suitable for particular pharmaceutical preparations.

The antioxidant mechanism(s) of carotenoids, and in particular astaxanthin, includes singlet oxygen quenching, direct radical scavenging, and lipid peroxidation chain-breaking. The polyene chain of the carotenoid absorbs the excited energy of singlet oxygen, effectively stabilizing the energy transfer by delocalization along the chain, and dissipates the energy to the local environment as heat. Transfer of energy from triplet-state chlorophyll (in plants) or other porphyrins and proto-porphyrins (in mammals) to carotenoids occurs much more readily than the alternative energy transfer to oxygen to form the highly reactive and destructive singlet oxygen ($^1O_2$). Carotenoids may also accept the excitation energy from singlet oxygen if any should be formed in situ, and again dissipate the energy as heat to the local environment. This singlet oxygen quenching ability has significant implications in cardiac ischemia, macular degeneration, porphyria, and other disease states in which production of singlet oxygen has damaging effects. In the physical quenching mechanism, the carotenoid molecule may be regenerated (most frequently), or be lost. Carotenoids are also excellent chain-breaking antioxidants, a mechanism important in inhibiting the peroxidation of lipids. Astaxanthin can donate a hydrogen (H) to the unstable polyunsaturated fatty acid (PUFA) radical, stopping the chain reaction. Peroxyl radicals may also, by addition to the polyene chain of carotenoids, be the proximate cause for lipid peroxide chain termination. The appropriate dose of astaxanthin has been shown to completely suppress the peroxyl radical chain reaction in liposome systems. Astaxanthin shares with vitamin E this dual antioxidant defense system of singlet oxygen quenching and direct radical scavenging, and in most instances (and particularly at low oxygen tension in vivo) is superior to vitamin E as a radical scavenger and physical quencher of singlet oxygen.

Carotenoids, and in particular astaxanthin, are potent direct radical scavengers and singlet oxygen quenchers and possess all the desirable qualities of such therapeutic agents for inhibition or amelioration of ischemia-reperfusion (I/R) injury. Synthesis of novel carotenoid derivatives with "soft-drug" properties (i.e. activity in the derivatized form), with physiologically relevant, cleavable linkages to pro-moieties, can generate significant levels of free carotenoids in both plasma and solid organs. This is critically important, for in mammals, diesters of carotenoids generate the non-esterified or "free" parent carotenoid, and may be viewed as elegant synthetic and novel delivery vehicles with improved properties for delivery of free carotenoid to the systemic circulation and ultimately to target tissue. In the case of non-esterified, free astaxanthin, this is a particularly useful embodiment (characteristics specific to non-esterified, free astaxanthin below):

- Lipid soluble in natural form; may be modified to become more water soluble
- Molecular weight of 597 Daltons [size<600 daltons (Da) readily crosses the blood brain barrier, or BBB]
- Long polyene chain characteristic of carotenoids effective in singlet oxygen quenching and lipid peroxidation chain breaking
- No pro-vitamin A activity in mammals (eliminating concerns of hypervitaminosis A and retinoid toxicity in humans).

The administration of antioxidants that are potent singlet oxygen quenchers and direct radical scavengers, particularly of superoxide anion, should limit hepatic fibrosis and the progression to cirrhosis by affecting the activation of hepatic stellate cells early in the fibrogenetic pathway. Reduction in the level of ROS by the administration of a potent antioxidant can therefore be crucial in the prevention of the activation of both HSC and Kupffer cells. This protective antioxidant effect appears to be spread across the range of potential therapeutic antioxidants, including water-soluble (e.g., vitamin C, glutathione, resveratrol) and lipophilic (e.g., vitamin E, β-carotene, astaxanthin) agents. Therefore, a co-antioxidant derivative strategy in which water-soluble and lipophilic agents are combined synthetically is a particularly useful embodiment.

Vitamin E is generally considered the reference antioxidant. When compared with vitamin E, carotenoids are more efficient in quenching singlet oxygen in homogeneous organic solvents and in liposome systems. They are better chain-breaking antioxidants as well in liposomal systems. They have demonstrated increased efficacy and potency in vivo. They are particularly effective at low oxygen tension, and in low concentration, making them extremely effective agents in disease conditions in which ischemia is an important part of the tissue injury and pathology. These carotenoids also have a natural tropism for the liver after oral administration. Therefore, therapeutic administration of carotenoids should provide a greater benefit in limiting fibrosis than vitamin E.

Problems related to the use of naturally occurring carotenoids and some structural carotenoid analogs include: (1) the complex isomeric mixtures, including non-carotenoid contaminants, provided in natural and synthetic sources leading to costly increases in safety and efficacy tests required by such agencies as the FDA; (2) limited bioavailability upon administration to a subject; and (3) the differential induction of cytochrome P450 enzymes (this family of enzymes exhibits species-specific differences which must be taken into account when extrapolating animal work to human studies).

SUMMARY OF THE INVENTION

This present application provides methods and compositions suitable for use in preventing or treating diseases or conditions associated with platelet aggregation; such diseases including but not limited to venous thrombosis, thrombophlebitis, arterial embolism, coronary and cerebral arterial thrombosis, unstable angina, myocardial infarction, stroke, cerebral embolism, kidney embolisms and pulmonary embolisms. The method is also directed to a method of preventing, treating or reducing the incidence of: thrombosis, thrombotic events, embolic events or pathological conditions associated with such events, where the thrombosis, thrombotic event or embolic event occurs during or after surgery.

In some embodiments, uses of carotenoids, carotenoid analogs or derivatives, including pharmaceutically acceptable salts thereof, may include the uses thereof in the formulation of pharmaceutical compositions suitable for the treatment of a disorder associated with platelet aggregation in a subject.

In some embodiments, pharmaceutical compositions suitable for use in the treatment of a disorder associated with platelet aggregation in a subject may include one or more carotenoid analogs or derivatives in an amount sufficient to at least partially decrease the risk of thrombotic events occurring in a subject.

In an embodiment, pharmaceutical compositions formulated for use in the treatment of a disorder associated with platelet aggregation may include one or more carotenoid analogs or derivatives in an amount sufficient to affect one or more biochemical pathways associated with platelet activation, including but not limited to increasing the bioavailability of NO to platelets, increasing the production and secretion of NO by platelets, and or reducing sources of oxidative stress and peroxynitrite formation.

In some embodiments, pharmaceutical compositions formulated for use in the treatment of a disorder associated with platelet aggregation are provided that may include one or more carotenoid analogs or derivatives in combination with one or more additional compositions or medicaments used in the treatment of platelet disorders, including but not limited to one or more additional agents that inhibit platelet aggregation. A composition in accordance with such an embodiment may include, for example, one or more carotenoid analogs or derivatives in combination with one or more additional antiplatelet agents.

In some embodiments, methods are provided for treating a disorder associated with platelet aggregation in a subject.

Such methods may include administering to an individual who would benefit from such treatment a therapeutically effective amount of a pharmaceutical composition that includes one or more carotenoid analogs or derivatives. Methods are also provided for the treatment a disorder associated with platelet aggregation, such methods comprising administering to an individual having need for such treatment a therapeutically effective amount of a pharmaceutical composition that includes one or more carotenoid analogs or derivatives and also administering to such an individual a therapeutically effective amount of one or more additional anti-platelet agents.

In certain embodiments, the carotenoid analogs or derivatives may be administered to a subject concurrently with one or more additional compositions or medicaments used in the treatment of a disorder associated with platelet aggregation, including but not limited to one or more additional anti-platelet agents. In an embodiment, the one or more additional compositions or medicaments may be administered to the subject either as a co-formulation, or as separate pharmaceutical and/or nutraceutical formulation administered as part of a co-therapy regimen. In one such embodiment, carotenoid analogs or derivatives may be administered to the subject undergoing such treatment prior to the commencement of drug therapy with the one or more additional compositions or medicaments used in the treatment of a disorder associated with platelet aggregation. In another embodiment, carotenoids analogs or derivatives may be administered to the subject following the commencement of drug therapy with the one or more additional compositions or medicaments used in the treatment of a disorder associated with platelet aggregation.

Administration of the carotenoid analogs or derivatives to a subject in accordance with the preceding embodiments may be provided to a subject with the intention of at least partially inhibiting and/or influencing some of the negative or undesirable cellular and/or biochemical processes that occur in pathologies associated with platelet aggregation. Administering one or more carotenoid analogs or derivatives by one skilled in the art as provided for herein—including consideration of the pharmacokinetics and pharmacodynamics of therapeutic drug delivery is expected to reduce and/or ameliorate at least a portion of the of the negative or undesirable cellular and/or biochemical processes that occur in disorders associated with platelet aggregation.

In some of the foregoing embodiments, analogs or derivatives of carotenoids may be at least partially water-soluble. "Water-soluble" structural carotenoid analogs or derivatives are those analogs or derivatives that may be formulated in aqueous solution, either alone or with one or more excipients. Water-soluble carotenoid analogs or derivatives may include those compounds and synthetic derivatives that form molecular self-assemblies, and may be more properly termed "water dispersible" carotenoid analogs or derivatives. Water-soluble and/or "water-dispersible" carotenoid analogs or derivatives may be preferred in some embodiments.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/ml-10 mg/mL. In certain embodiments, water-soluble carotenoid analogs or derivatives may have a water solubility of greater than about 20 mg/mL. In certain embodiments, water-soluble carotenoid analogs or derivatives may have a water solubility of greater than about 25 mg/mL. In some embodiments, water-soluble carotenoid analogs or derivatives may have a water solubility of greater than about 50 mg/mL.

In some embodiments, water-soluble analogs or derivatives of carotenoids may be administered to a subject alone or in combination with additional carotenoids or structural analogs or derivatives thereof. In some embodiments, water-soluble analogs or derivatives of carotenoids may be administered to a subject alone or in combination with other antioxidants.

The uses, methods and compositions contemplated herein include the use of one or more carotenoid analogs or derivatives. In some embodiments, a carotenoid analogs or derivatives may have the structure:

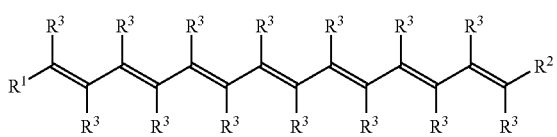

where each $R^3$ is independently hydrogen or methyl, and where $R^1$ and $R^2$ are each independently:

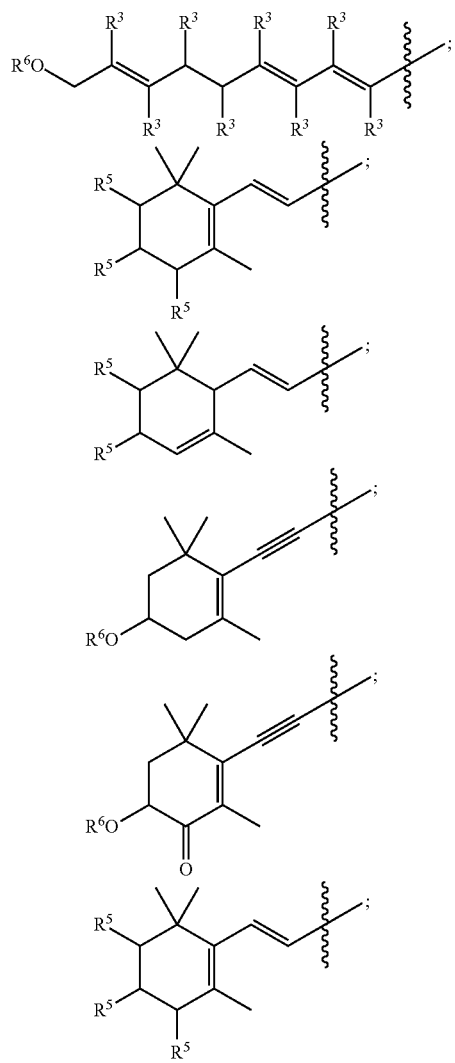

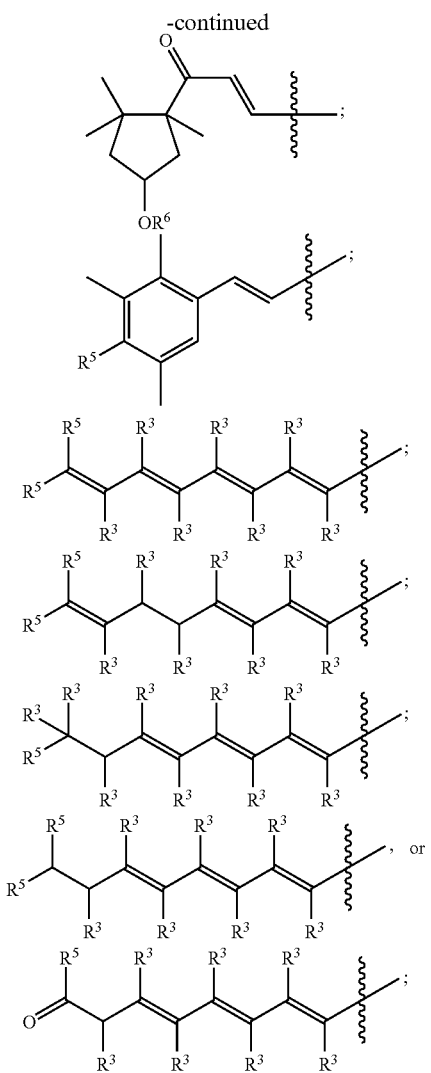

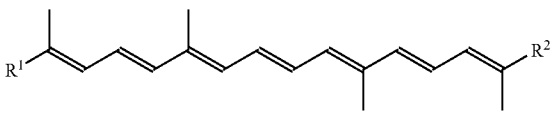

where each $R^1$ and $R^2$ are independently:

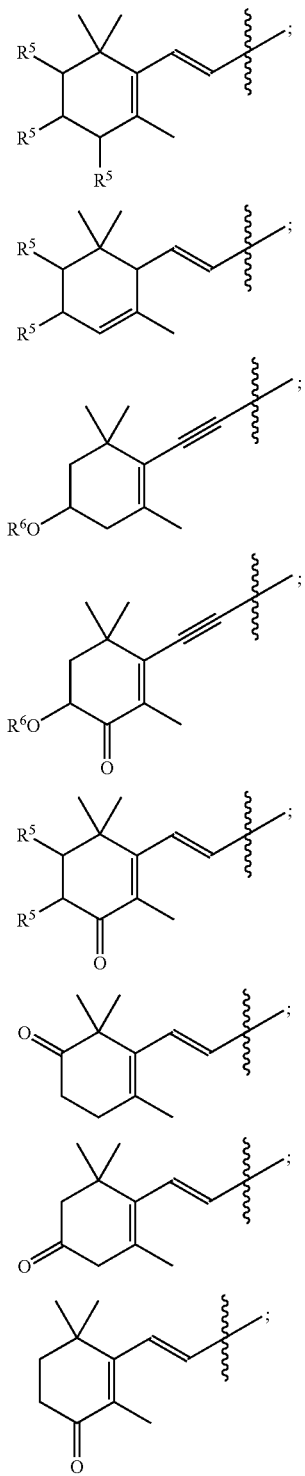

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-$N(R^7)_2$; -aryl-$N(R^7)_2$; -alkyl-$N^+(R^7)_3$; -aryl-$N^+(R^7)_3$; -alkyl-$CO_2R^9$; -aryl-$CO_2R^9$; -alkyl-$CO_2^-$; -aryl-$CO_2^-$; —C(O)-alkyl-$N(R^7)_2$; —C(O)-aryl-$N(R^7)_2$; —C(O)-alkyl-$N^+(R^7)_3$; —C(O)-aryl-$N^+(R^7)_3$; —C(O)-alkyl-$CO_2R^9$; —C(O)-aryl-$CO_2R^9$; —C(O)-alkyl-$CO_2^-$; —C(O)-aryl-$CO_2^-$; —C(O)—$(NR^7)$-alkyl-$N(R^7)_2$; —C(O)—$(NR^7)$-aryl-$N(R^7)_2$; —C(O)—$(NR^7)$-alkyl-$N^+(R^7)_3$; —C(O)—$(NR^7)$-aryl-$N^+(R^7)_3$; —C(O)—$(NR^7)$-alkyl-$CO_2R^9$; —C(O)—$(NR^7)$-aryl-$CO_2R^9$; —C(O)—$(NR^7)$-alkyl-$CO_2^-$; —C(O)—$(NR^7)$-aryl-$CO_2^-$; —C(O)—$(NR^7)$-alkyl-$N(R^7)$-alkyl-$N(R^7)_2$; —C(O)—$OR^8$; —P(O)$(OR^8)_2$; —S(O)$(OR^8)_2$; —C(O)—[$C_6$-$C_{24}$ saturated hydrocarbon]; —C(O)—[$C_6$-$C_{24}$ monounsaturated hydrocarbon]; —C(O)—[$C_6$-$C_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)$(OR^8)_2$, —S(O)$(OR^8)_2$, an amino acid, a peptide, a carbohydrate, a nucleoside, or a co-antioxidant.

In some embodiments, carotenoid analogs or derivatives suitable for use with the present compositions, methods and uses may have the structure

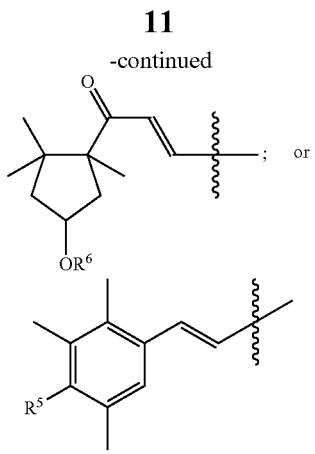

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-N($R^7$)$_2$; -aryl-N($R^7$)$_2$; -alkyl-N$^+$($R^7$)$_3$; -aryl-N$^+$($R^7$)$_3$; -alkyl-CO$_2R^9$; -aryl-CO$_2R^9$; -alkyl-CO$_2^-$; -aryl-CO$_2^-$; —C(O)-alkyl-N($R^7$)$_2$; —C(O)-aryl-N($R^7$)$_2$; —C(O)-alkyl-N$^+$($R^7$)$_3$; —C(O)-aryl-N$^+$($R^7$)$_3$; —C(O)-alkyl-CO$_2R^9$; —C(O)-aryl-CO$_2R^9$; —C(O)-alkyl-CO$_2^-$; —C(O)-aryl-CO$_2^-$; —C(O)—(NR$^7$)-alkyl-N($R^7$)$_2$; —C(O)—(NR$^7$)-aryl-N($R^7$)$_2$; —C(O)—(NR$^7$)-alkyl-N$^+$($R^7$)$_3$; —C(O)—(NR$^7$)-aryl-N$^+$($R^7$)$_3$; —C(O)—(NR$^7$)-alkyl-CO$_2R^9$; —C(O)—(NR$^7$)-aryl-CO$_2R^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N($R^7$)$_2$; —C(O)—OR$^8$; —P(O)(OR$^8$)$_2$; —S(O)(OR$^8$)$_2$; —C(O)-amino acid; —C(NR$^7$)-amino acid; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, each —$OR^6$ group may independently be

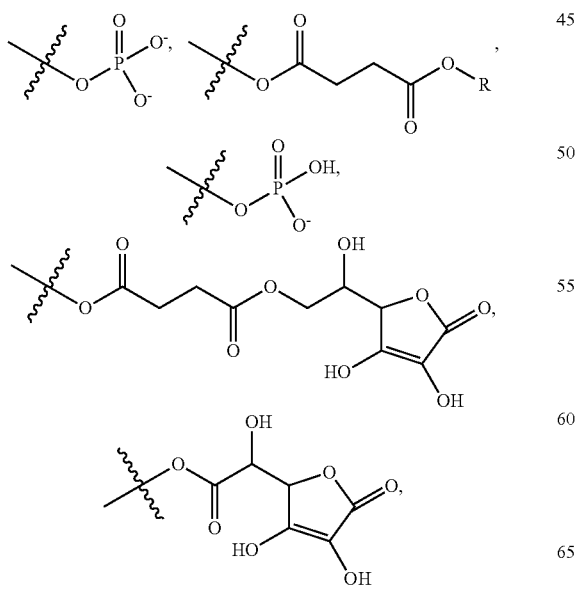

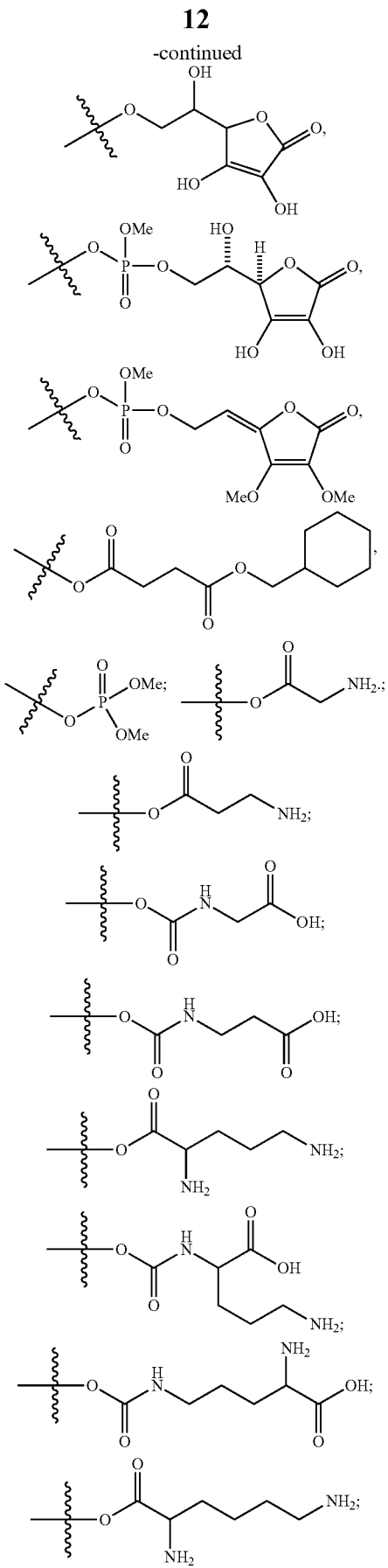

13

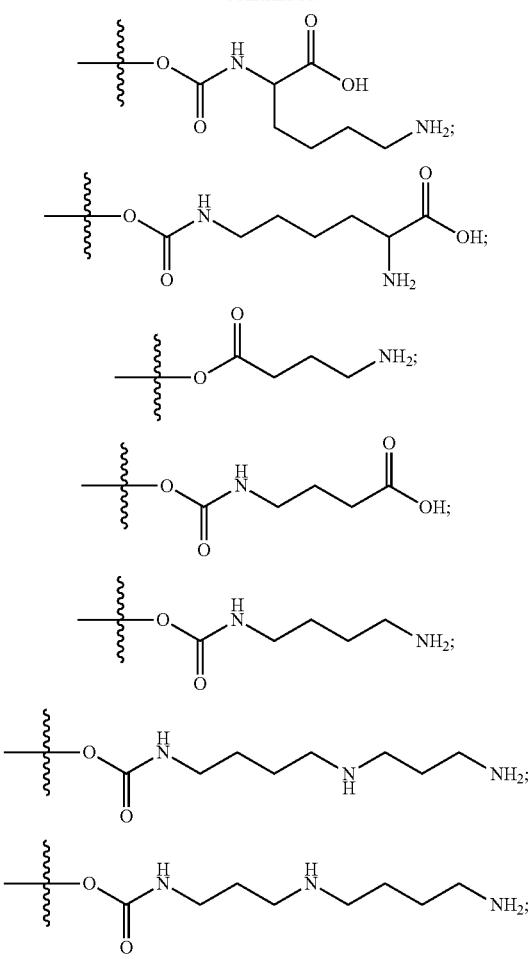

—C(O)—CH$_2$—NHMe, —C(O)—NHMe-CH$_2$—CO$_2$R$^9$, and pharmaceutically acceptable salts of any of these compounds, where each R is independently H, alkyl, aryl, benzyl, Group IA metal, or co-antioxidant.

In some embodiments, carotenoid analogs or derivatives suitable for use with the present compositions, methods and uses may have the structure

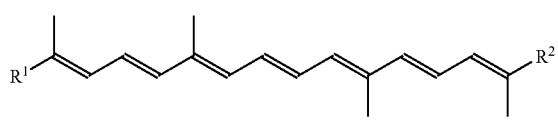

where each R$^3$ is independently hydrogen or methyl, and wherein each R$^1$ and R$^2$ are independently:

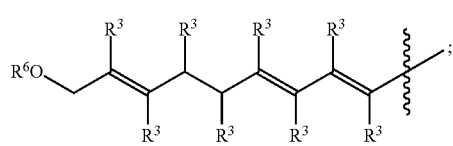

14

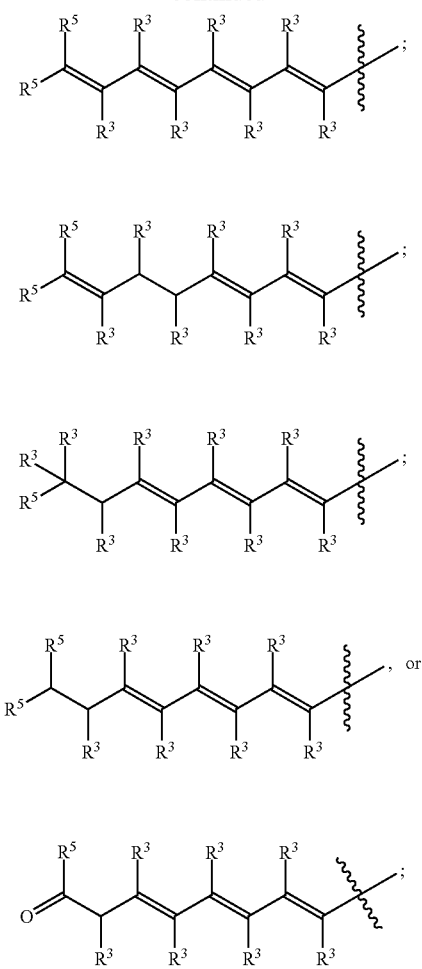

where each R$^5$ is independently hydrogen, —CH$_3$, —OH, —CH$_2$OH or —OR$^6$ wherein at least one R$^5$ group in the carotenoid analog or derivative is —OR$^6$; wherein each R$^6$ is independently: H; alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2$$^-$; -aryl-CO$_2$$^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2$$^-$; —C(O)-aryl-CO$_2$$^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(R$^7$)-aryl-CO$_2$R$^9$; —C(O)—(NR$^7$)-alkyl-CO$_2$$^-$; —C(O)—(NR$^7$)-aryl-CO$_2$$^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)-amino acid; —C(NR$^7$)-amino acid; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where R$^7$ is hydrogen, alkyl, or aryl; where R$^8$ is hydrogen, alkyl, aryl, benzyl or a co-antioxidant; and where R$^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, carotenoid analogs or derivatives suitable for use with the present compositions, methods and uses may have the structure:

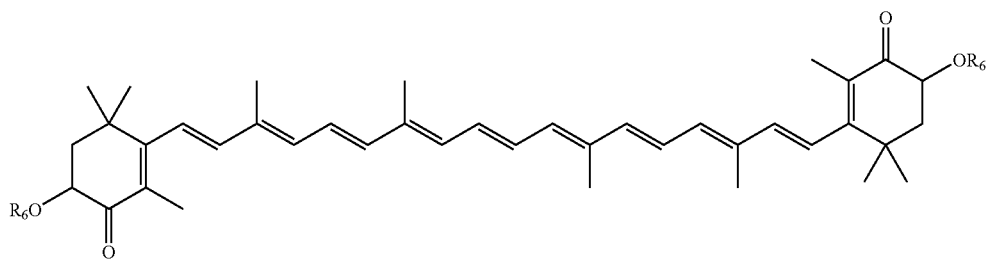

wherein each $R^6$ is independently: H; alkyl; aryl; -alkyl-N$(R^7)_2$; -aryl-N$(R^7)_2$; -alkyl-N$^+(R^7)_3$; -aryl-N$^+(R^7)_3$; -alkyl-CO$_2$R$^9$; -aryl-CO$_2$R$^9$; -alkyl-CO$_2^-$; -aryl-CO$_2^-$; —C(O)-alkyl-N$(R^7)_2$; —C(O)-aryl-N$(R^7)_2$; —C(O)-alkyl-N$^+(R^7)_3$; —C(O)-aryl-N$^+(R^7)_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N$(R^7)_2$; —C(O)—(NR$^7$)-aryl-N$(R^7)_2$; —C(O)—(NR$^7$)-alkyl-N$^+(R^7)_3$; —C(O)—(NR$^7$)-aryl-N$^+(R^7)_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N$(R^7)_2$; —C(O)—OR$^8$; —P(O)(OR$^8$)$_2$; —S(O)(OR$^8$)$_2$; —C(O)-amino acid; —C(NR$^7$)-amino acid; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a method for treating a disorder associated with platelet aggregation in a subject may include administering to the subject an effective amount of a pharmaceutically acceptable formulation including a synthetic analog or derivative of a carotenoid. The synthetic analog or derivative of the carotenoid may have the structure (I)

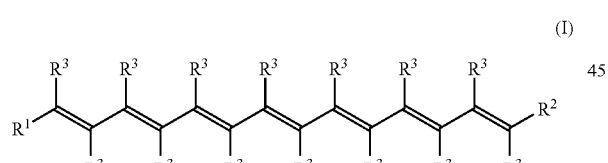

where each $R^3$ is independently hydrogen or methyl, and where $R^1$ and $R^2$ are each independently:

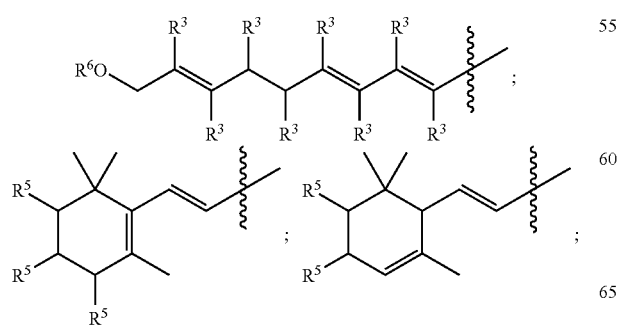

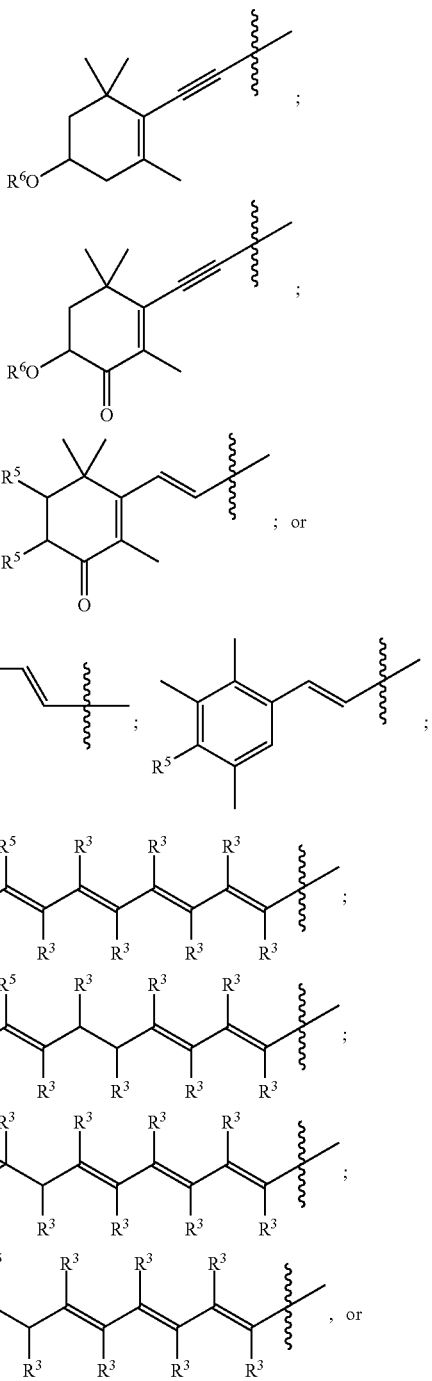

-continued

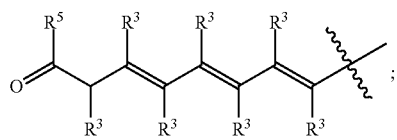

wherein $R^4$ is independently hydrogen, —OH, —CH$_2$OH, or —OR$^6$; where each $R^5$ is independently hydrogen, —CH$_3$, —OH, —CH$_2$OH or —OR$^6$ wherein at least one $R^5$ group in the carotenoid analog or derivative is —OR$^6$; wherein each $R^6$ is independently: H; alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)-amino acid; —C(NR$^7$)-amino acid; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a method for treating a disorder associated with platelet aggregation in a subject may include administering to the subject an effective amount of a pharmaceutically acceptable formulation including a synthetic analog or derivative of a carotenoid where each —OR$^6$ group may independently be:

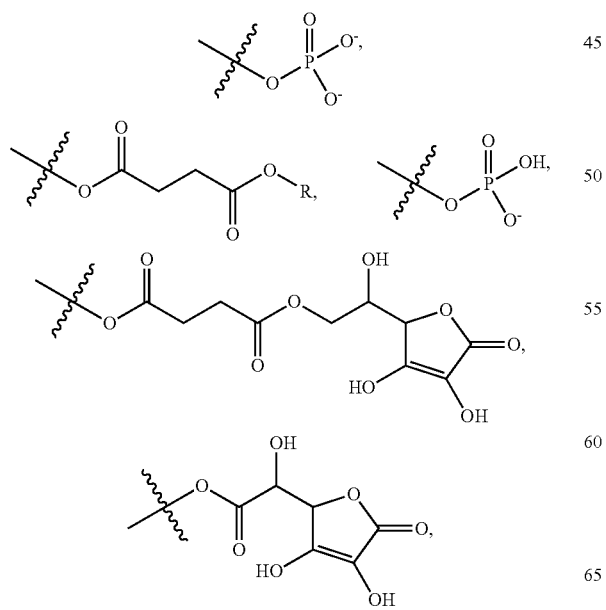

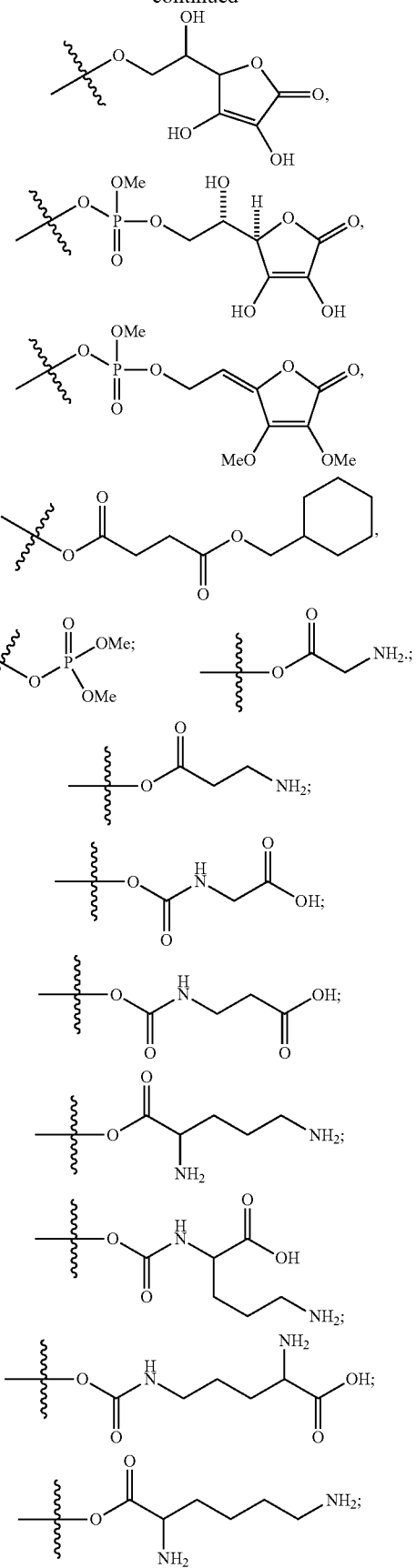

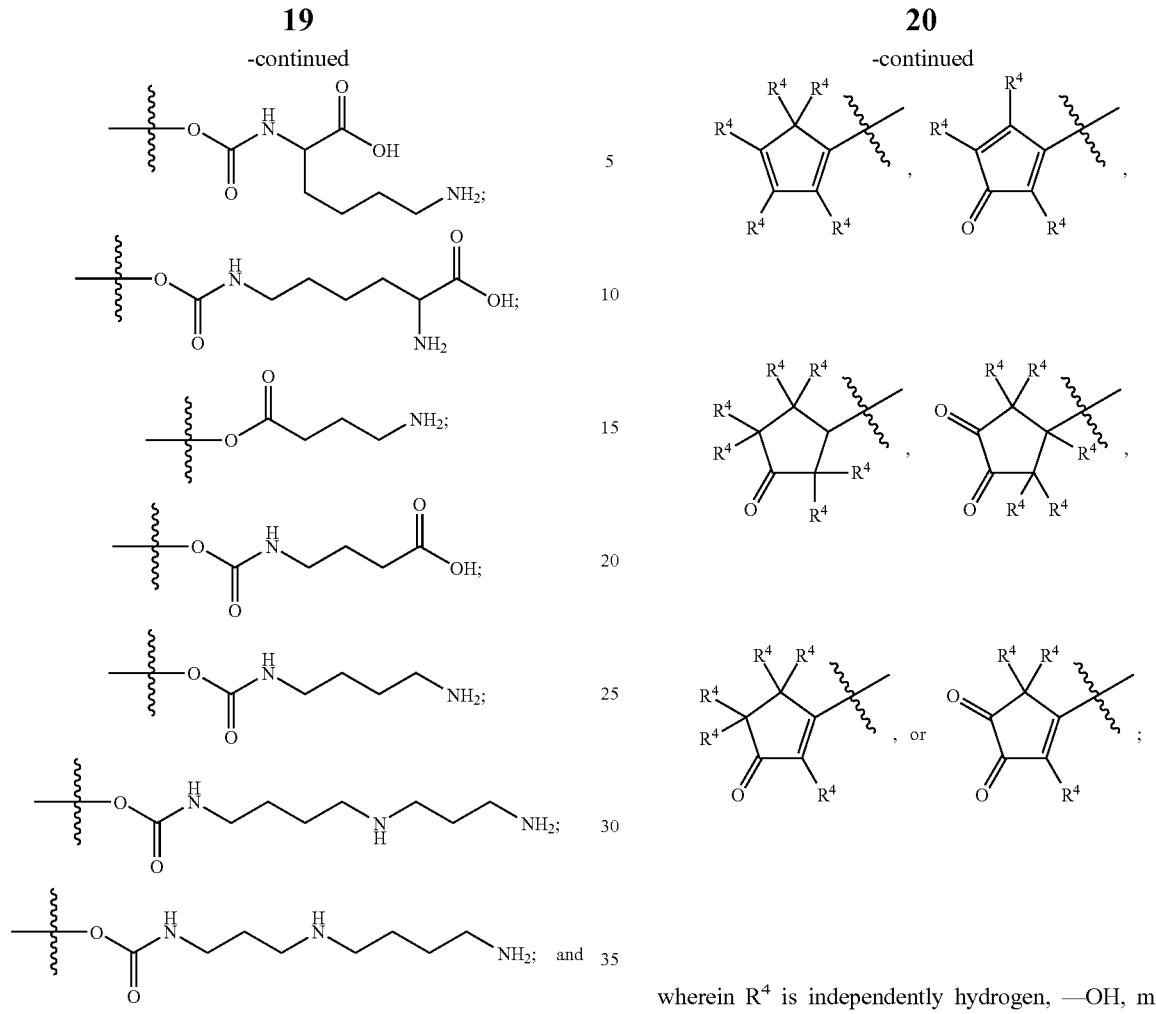

pharmaceutically acceptable salts of any of these compounds, where each R is independently H, alkyl, aryl, benzyl, Group IA metal, or co-antioxidant.

In some embodiments, a composition may include one or more carotenoids, carotenoid analogs, carotenoid derivatives, and pharmaceutically acceptable derivatives of carotenoids, carotenoid analogs, and carotenoid derivatives having the general structure:

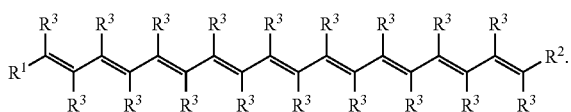

Each $R^3$ may be independently hydrogen or methyl. Each $R^1$ and $R^2$ may be independently:

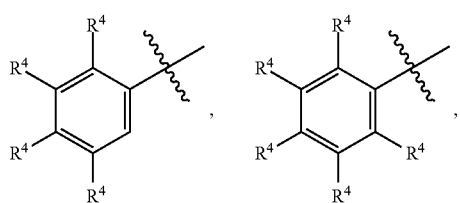

wherein $R^4$ is independently hydrogen, —OH, methyl, —CH$_2$OH, or —OR$^5$; wherein at least one $R^4$ group in the carotenoid analog or derivative may be —OR$^5$; wherein each $R^5$ is independently: alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a composition may include one or more carotenoids, carotenoid analogs, carotenoid derivatives, and pharmaceutically acceptable derivatives of carotenoids, carotenoid analogs, and carotenoid derivatives having the general structure:

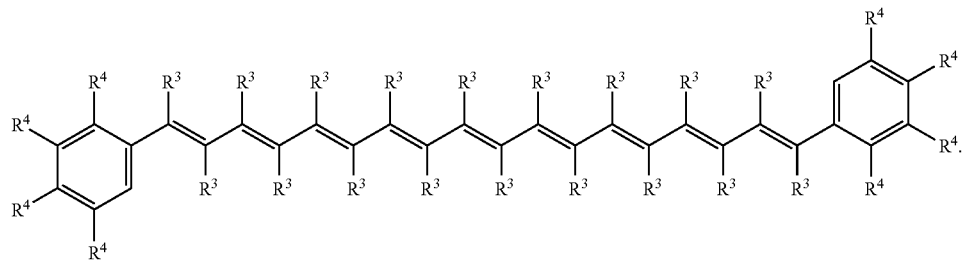

wherein $R^4$ is independently hydrogen, —OH, methyl, —CH$_2$OH, or —OR$^5$; wherein at least one $R^4$ group in the carotenoid analog or derivative may be —OR$^5$; wherein each $R^5$ is independently: alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a composition may include one or more carotenoids, carotenoid analogs, carotenoid derivatives, and pharmaceutically acceptable derivatives of carotenoids, carotenoid analogs, and carotenoid derivatives having the general structure:

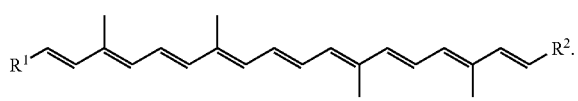

Each $R^3$ may be independently hydrogen or methyl, and where each $R^1$ and $R^2$ may be independently:

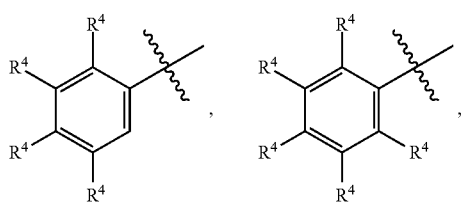

-continued

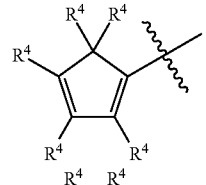

wherein $R^4$ is independently hydrogen, —OH, methyl, —CH$_2$OH, or —OR$^5$; wherein at least one $R^4$ group in the carotenoid analog or derivative may be —OR$^5$; wherein each $R^5$ is independently: alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a composition may include one or more carotenoids, carotenoid analogs, carotenoid derivatives, and pharmaceutically acceptable derivatives of carotenoids, carotenoid analogs, and carotenoid derivatives having the general structure:

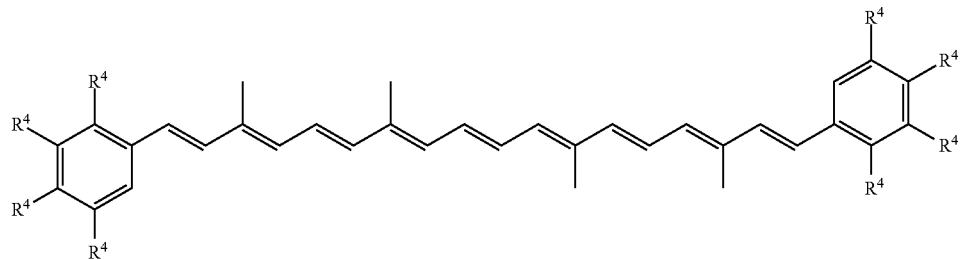

wherein R⁴ is independently hydrogen, —OH, methyl, —CH₂OH, or —OR⁵; wherein at least one R⁴ group in the carotenoid analog or derivative may be —OR⁵; wherein each R⁵ is independently: alkyl; aryl; -alkyl-N(R⁷)₂; -aryl-N(R⁷)₂; -alkyl-N⁺(R⁷)₃; -aryl-N⁺(R⁷)₃; -alkyl-CO₂R⁹; -aryl-CO₂R⁹; -alkyl-CO₂⁻; -aryl-CO₂⁻; —C(O)-alkyl-N(R⁷)₂; —C(O)-aryl-N(R⁷)₂; —C(O)-alkyl-N⁺(R⁷)₃; —C(O)-aryl-N⁺(R⁷)₃; —C(O)-alkyl-CO₂R⁹; —C(O)-aryl-CO₂R⁹; —C(O)-alkyl-CO₂⁻; —C(O)-aryl-CO₂⁻; —C(O)—(NR⁷)-alkyl-N(R⁷)₂; —C(O)—(NR⁷)-aryl-N(R⁷)₂; —C(O)—(NR⁷)-alkyl-N⁺(R⁷)₃; —C(O)—(NR⁷)-aryl-N⁺(R⁷)₃; —C(O)—(NR⁷)-alkyl-CO₂R⁹; —C(O)—(NR⁷)-aryl-CO₂R⁹; —C(O)—(R⁷)-alkyl-CO₂⁻; —C(O)—(NR⁷)-aryl-CO₂⁻; —C(O)—(NR⁷)-alkyl-N(R⁷)-alkyl-N(R⁷)₂; —C(O)—OR⁸; —P(O)(OR⁸)₂; —S(O)(OR⁸)₂; —C(O)—[C₆-C₂₄ saturated hydrocarbon]; —C(O)—[C₆-C₂₄ monounsaturated hydrocarbon]; —C(O)—[C₆-C₂₄ polyunsaturated hydrocarbon]; a peptide; a carbohydrate; a nucleoside reside; or a co-antioxidant; where R⁷ is hydrogen, alkyl, or aryl; where R⁸ is hydrogen, alkyl, aryl, benzyl or a co-antioxidant; and where R⁹ is hydrogen, alkyl, aryl, —P(O)(OR⁸)₂, —S(O)(OR⁸)₂, an amino acid, a peptide, a carbohydrate, a nucleoside, or a co-antioxidant.

Each co-antioxidant may be independently Vitamin C, Vitamin C analogs, Vitamin C derivatives, Vitamin E, Vitamin E analogs, Vitamin E derivatives, flavonoids, flavonoid derivatives, or flavonoid analogs. Flavonoids include, but are not limited to, quercetin, xanthohumol, isoxanthohumol, or genistein. Selection of the co-antioxidant should not be seen as limiting for the therapeutic application of the current invention.

In some embodiments, pharmaceutical compositions are provided that may include one or more carotenoids ("a co-formulation" strategy), or synthetic derivatives or analogs thereof, in combination with one or more additional compositions or medicaments used in the treatment of platelet disorders. Certain embodiments may be further directed to pharmaceutical compositions that include combinations of two or more carotenoids or synthetic analogs or derivatives thereof.

In some embodiments, separate pharmaceutical compositions are provided, such that the one or more additional compositions or medicaments used in the treatment of a disorder associated with platelet aggregation is/are delivered separately from the carotenoid, or synthetic derivatives or analogs thereof (sometimes referred to in the art as a "co-administration"strategy). The pharmaceutical compositions may be adapted to be administered orally, or by one or more parenteral routes of administration. In an embodiment, the pharmaceutical composition may be adapted such that at least a portion of the dosage of the carotenoid or synthetic derivative or analog thereof is delivered prior to, during, or after at least a portion of the one or more additional compositions or medicaments used in the treatment of a disorder associated with platelet aggregation is/are delivered to the subject.

Embodiments directed to pharmaceutical compositions may further include appropriate vehicles for delivery of said pharmaceutical composition to a desired site of action (i.e., the site a subject's body where the biological effect of the pharmaceutical composition is most desired). Pharmaceutical compositions including carotenoids or analogs that may be administered orally or intravenously may be particularly advantageous for and suited to embodiments described herein. In yet a further embodiment, an injectable pharmaceutical composition may be prepared.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings.

FIGS. 3A and B show the effects of nitric oxide release from vascular platelets following incubation with homochiral astaxanthin and clopidogrel, either alone or in combination;

FIG. 8 shows the percent platelet aggregation responses to ADP (A) and AA (B) before and after occlusive thrombus formation in the LCA and subsequent treatment with DDA (10, 30 or 50 mg/kg) or 0.9% NaCl solution (0 mg/kg DDA) followed immediately by rt-PA;

FIG. 20 shows a table summarizing the experiments run to determine the metabolism of carotenoid derivatives in various animals;

FIG. 22 shows pharmacokinetic data determined after the administration of carotenoid derivatives to rats;

FIG. 23 shows pharmacokinetic data determined after the administration of ADL carotenoid derivatives to dogs;

FIG. 24 shows accumulation of carotenoid in various tissues after the administration of carotenoid derivatives to dogs;

FIG. 26 shows pharmacokinetic data determined after the administration of ADG and ADSa carotenoid derivatives to dogs; and FIG. 27 shows pharmacokinetic data determined after the administration of carotenoid derivatives to monkeys.

Figure 1A:
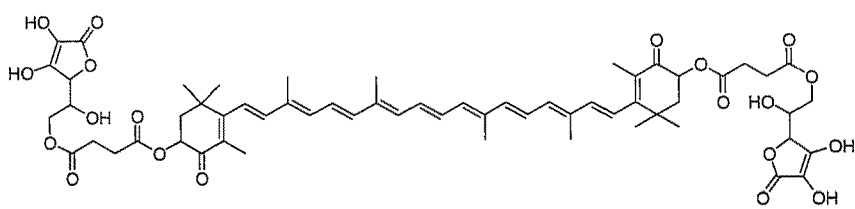
FIG. 1 shows several examples of the structures of various synthetic carotenoid derivatives or analogs that may be used according to some embodiments. (A) disuccinate divitamin C astaxanthin; (B) disodium disuccinic acid ester astaxanthin salt; (C) dilysinate astaxanthin ester salt.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE EMBODIMENTS

Definitions

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a linker" includes one or more linkers. It is to be yet further understood that any terminology used herein is for the purpose of describing particular embodiments only, and is not intended to be limiting.

The terms used throughout this specification generally have their ordinary meanings in the art, within the context of the invention, and in the specific context where each term is used. Certain terms are discussed below, or elsewhere in the specification, to provide additional guidance to the practitioner in describing the general embodiments of the invention, as well as how to make and use them. It will be readily appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein the term "carotenoid analogs and derivatives" may be generally defined as biologically active structural analogs and derivatives of carotenoids. Typical analogs include molecules which demonstrate equivalent or improved biologically useful and relevant function, but which differ structurally from the parent (i.e., naturally occurring) compounds. Parent carotenoids are selected from the more than 600 naturally-occurring carotenoids described in the literature, and their stereo- and geometric isomers. Such analogs may include, but are not limited to, esters, ethers, carbonates, amides, carbamates, phosphate esters and ethers, sulfates, glycoside ethers, with or without spacers (linkers).

As used herein, the term "xanthophyll carotenoid" generally refers to a naturally occurring or synthetic 40-carbon polyene chain with a carotenoid structure that contains at least one oxygen-containing functional group. The chain may include terminal cyclic end groups. Exemplary, though non-limiting, xanthophyll carotenoids include astaxanthin, zeaxanthin, lutein, echinenone, lycophyll, canthaxanthin, and the like. Non-limiting examples of carotenoids that are not xanthophyll carotenoids include β-carotene and lycopene.

As used herein, terms such as "carotenoid analog" and "carotenoid derivative" generally refer to chemical compounds or compositions derived from a naturally occurring or synthetic carotenoid. Terms such as carotenoid analog and carotenoid derivative may also generally refer to chemical compounds or compositions that are synthetically derived from non-carotenoid based parent compounds; however, which ultimately substantially resemble a carotenoid derived analog. Non-limiting examples of carotenoid analogs and derivatives that may be used according to some of the embodiments described herein are depicted schematically in FIG. 1.

As used herein, the term "organ", when used in reference to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

As used herein the terms "reducing," "inhibiting" and "ameliorating," when used in the context of modulating a pathological or disease state, generally refers to the prevention and/or reduction of at least a portion of the negative consequences of the disease state. When used in the context of a biochemical event or pathway, the term generally refers to a net reduction in the magnitude or activity of said pathway.

As used herein, the phrase "increase the bioavailability of nitric oxide (NO)" generally refers to a physiological event, stimulus or treatment that produces a net increase in the amount of biologically active NO available to affect physiological responses dependent thereon. In the context of the present application, the phrase, unless other wise specified, is generally meant in reference to net amount of biologically active NO that is available to affect platelet function. The bioactive NO described in the context of the instant application is not limited to any one particular source or sources. Nevertheless, it will be readily appreciated by the skilled practitioner that the majority of bioactive NO available to platelets is typically derived from vascular endothelium as well as from the platelets themselves. Generally, NO has a net inhibitory effect on platelet aggregation.

As used herein, the term "platelet" generally refers to the cell fragments circulating in the blood that are involved in the cellular mechanisms of primary hemostasis leading to the formation of blood clots. Dysfunction or low levels of platelets predisposes to bleeding, while high levels, although usually asymptomatic, may increase the risk of thrombosis. Platelets are produced in the bone marrow and are the fragmented products of megakaryocytes. Platelets are anuclear and discoid cell fragments measuring 1.5-3.0 µm in diameter. The body has a very limited reserve of platelets, so they can be rapidly depleted. They contain RNA, mitochondria, a canalicular system, and several different types of granules; lysosomes (containing acid hydrolases), dense bodies (containing ADP, ATP, serotonin and calcium) and alpha granules (containing fibrinogen, factor V, vitronectin, thrombospondin and von Willebrand factor), the contents of which are released upon activation of the platelet. Platelets are activated when brought into contact with collagen (which is exposed when the endothelial blood vessel lining is damaged), thrombin (primarily through PAR-1), ADP, receptors expressed on white blood cells or the endothelial cells of the blood vessels, a negatively charged surface (e.g., glass), or several other activating factors. Once activated, they release a number of different coagulation factors and platelet activating factors. Platelet activation further results in the transport of negatively charged phospholipids to the platelet surface. These phospholipids provide a catalytic surface (with the charge provided by phosphatidylserine and phosphatidylethanolamine) for the tenase and prothrombinase complexes. The platelets adhere to each other via adhesion receptors or integrins, and to the endothelial cells in the wall of the blood vessel forming a haemostatic plug in conjunction with fibrin. The high concentration of myosin and actin filaments to platelets are stimulated to contract during aggregation, further reinforcing the plug. The most abundant platelet adhesion receptor is glycoprotein (GP) IIb/IIIa; this is a calcium-dependent receptor for fibrinogen, fibronectin, vitronectin, thrombospondin and von Willebrand factor (vWF). Other receptors include GPIb-V-IX complex (vWF) and GPVI (collagen).

A variety of molecules are know to function as platelet activators. Examples of platelet activating molecules include: collagen, which is exposed when endothelial blood vessel lining is damaged and binds to its receptors GPVI and $\alpha_{2b}$-$\beta_1$; von Willebrand factor (vWF), which circulates in the blood and binds to its receptor GPIb-IX-V; thrombin, primarily through cleavage of the extracellular domain of PAR1 and PAR4; thromboxane $A_2$ ($TXA_2$), which binds to its receptor, TP-R; ADP through action on its two cell surface receptors, $P2Y_1$ and $P2Y_{12}$; adrenaline through its receptor (alpha 2); serotonin, through its receptor (5HT-2c); human neutrophil elastase (HNE), which cleaves the $\alpha_{IIb}$-$\beta_3$ integrin on the platelet surface; and P-selectin, which is exposed on the surface of activated platelets and which binds PSGL-1 on endothelial cells and white blood cells.

Likewise, a variety of endogenous molecules are know to function as platelet inhibitors. Examples of endogenous molecules known to inhibit platelet function include: prostacyclin, which opposes the actions of most if not all platelet agonists by increasing intracellular cAMP levels; adenosine, which signals through its receptor (A2 receptor) on the surface of platelets and increases intracellular cAMP levels; nitric oxide (NO), which is released by vascular endothelial cells and activated platelets, increases cGMP levels in platelets by directly activating the enzyme guanylyl cyclase in platelets; clotting factors II, IX, X, XI, XII; and nucleotidases, such as CD39 ecto-ADPase, which hydrolyze ADP.

Various drugs are known to inhibit platelet function. Non-limiting examples of platlet inhibitor drugs include: Aspirin, which irreversibly inhibits cyclooxygenase-1 and blocks the formation of $TXA_2$ to platelets; clopidogrel, which is an antiplatelet drug that irreversibly inhibits ADP receptors, non-steroidal anti-inflammatory drugs (NSAIDs), which inhibit prostaglandin synthesis, Abciximab, another antiplatelet drug, which blocks fibrinogen receptors; and quinidine, a calcium channel blocker.

As used herein, phrases such as "one or more additional medicaments or compositions suitable for the treatment of a disorder associated with platelet aggregation in a subject," or more simply, "one or more additional compositions or medicaments," generally refer to a pharmaceutical composition that contains at least one pharmaceutically active compound that is used for the treatment of platelet aggregation disorders, but which is distinct from the carotenoid analogs or derivatives that form the basis of the present disclosure. Typically one or more additional medicaments or compositions suitable for the treatment of a disorder associated with platelet aggregation in a subject as presently described may include one or more antiplatelet agents. Exemplary though non-limiting antiplatelet agents suitable for use in the presently described embodiments include: anticoagulants; statins; ADP receptor inhibitors (e.g., thienopyridines); thrombin inhibitors; factor Xa inhibitors; agonists of purinergic receptors; antagonists of CD40 or CD40 ligand (CD40L) or compounds that disrupt (e.g., reduce) the interaction of CD40 and CD40L; eicosanoid related targets (e.g., COX inhibitors, PGE1 agonists, PG synthase inhibitors, TX synthase inhibitors, and $TXA_2$ antagonists); and glycoprotein IIb/IIIa antagonists. Exemplary anticoaglulants suitable for use in accordance with the presently disclosed treatment methods include, e.g., aspirin, warfarin, a combination of aspirin and warfarin. Exemplary non-fractionated or fractionated heparins may include low molecular weight heparins, such as ardeparin, certoparin, dalteparin, enoxaparin, nadroparin, reviparin, or tinazaparin, and those compounds described in WO 97/35592. Exemplary statins suitable for use in accordance with the presently disclosed treatment methods include, e.g., atorvastatin, fluvastatin, lovastatin, pravastatin, or simvastatin. Exemplary ADP receptor inhibitors suitable for use in accordance with the presently disclosed treatment methods include, e.g., clopidogrel, ditazole, pirozadil, sarpogrelate, and ticlopidine. Exemplary thrombin inhibitors suitable for use in accordance with the presently disclosed treatment methods include, e.g., argatroban, dermatan, desirudin, efegatran, inogatran, lepirudin, melagatran, mesoglycan, PEG-r-hirudin, and reviparin. Factor Xa inhibitors include, for example, danaparoid, fondaparinux, and tifacogin. Exemplary purinergic receptor agonists suitable for use in accordance with the presently disclosed treatment methods include, e.g., adenosine and adenosine analogs, e.g., 2-(N-pyrazolyl) derivatives of adenosine (e.g., CVT 3146), and 2-propynylcyclohexyl-5'-N-ethylcarboxamido derivatives of adenosine (e.g., ATL-146e (4-(3-[6-amino-9-(5-ethylcarbamoyl-3,4-dihydroxy-tetrahydro-furan-2-yl)-9H-purin-2-yl]-prop-2-ynyl)-cyclohexanecarboxylic acid methyl ester), and ATL-193. Exemplary antagonists of CD40 or CD40 ligand (CD40L) or compounds that disrupt (e.g., reduce) the interaction of CD40 and CD40L include monoclonal antibodies (e.g., Antora and IDEC 131 and see US 2002/0031512 and WO01/34649), free CD40, and antisense nucleic acids. Exemplary eicosanoid related targets include alprostadil, beraprost, carbasalate, cloricromene, epoprost, etersalate, iloprost, indobufin, indometacin farnesil, limaprost, ozagrel, pamicogrel, picotamide, ramatroban, terbogrel, and triflusal. Exemplary glycoprotein IIb/IIIa antagonists for use in the methods and compositions of the invention include xemilofiban, abciximab, cromafiban, elarofiban, orbofiban, roxifiban, sibrafiban, RPR 109891, eptifibatide, and tirofiban.

The term "nitric oxide" (NO), as used herein, generally refers to a chemical compound that is a key biological messenger, playing a role in a variety of biological processes. Nitric oxide (NO) is produced by vascular endothelium and smooth muscle, cardiac muscle, and many other cell types. The substrate for NO is L-arginine that is transported into the cell. When acted upon by nitric oxide synthase (NOS), NO and citrulline are formed. There are two general forms of NOS: constitutive and inducible. NO is continuously produced by constitutive NO synthase (cNOS). The cNOS found in endothelial cells is also referred as eNOS, ecNOS, or Type III NOS. The activity of cNOS is modulated by calcium that is released from subsarcolemmal storage sites in response to the binding of certain ligands to their receptors. Substances such as acetylcholine, bradykinin, histamine, insulin, and substance P stimulate NO production by this mechanism. Another important mechanism regulating the release of NO is shearing forces acting on the luminal surface of vascular endothelium. By this mechanism, increased flow velocity stimulates calcium release and increased cNOS activity. The inducible form of NOS (iNOS, or Type II NOS) is not calcium-dependent, but instead is stimulated by the actions of cytokines (e.g., tumor necrosis factor, interleukins) and bacterial endotoxins (e.g., lipopolysaccharide). Induction of iNOS occurs over several hours and results in NO production that may be more than a 1,000-fold greater than that produced by cNOS. This is an important mechanism in the pathogenesis of inflammation.

Nitric oxide serves many important functions in the cardiovascular system, including but not limited to: vasodilation (ligand mediated and flow dependent); inhibition of vasoconstrictor influences (e.g., inhibits angiotensin II and sympathetic vasoconstriction); inhibition of platelet adhesion to the vascular endothelium (anti-thrombotic); inhibition of leukocyte adhesion to vascular endothelium (anti-inflammatory); antiproliferative (e.g., inhibits smooth muscle hyperplasia following vascular injury); and scavenging superoxide anion (anti-inflammatory).

The mechanism of many of these actions of NO involves the formation of cGMP. When NO is formed by an endothelial cell, for example, it readily diffuses out of the cell and into adjacent smooth muscle cells where it binds to and stimulates the enzyme guanylyl cyclase to cGMP. Increased cGMP activates a kinase that subsequently leads to the inhibition of calcium influx into the smooth muscle cell, and decreased calcium-calmodulin stimulation of myosin light chain kinase (MLCK). This in turn decreases the phosphorylation of myosin light chains, thereby decreasing smooth muscle tension development and causing vasodilation.

The anti-platelet aggregatory effects of NO are also related to the increase in cGMP. Drugs that inhibit the breakdown of cGMP (inhibitors of cGMP-dependent phosphodiesterase such as sildenafil) potentiate the effects of NO-mediated actions on the target cell.

When NO production is impaired as occurs when the vascular endothelium becomes damaged or dysfunctional, the following can result: vasoconstriction (e.g., coronary vasospasm, elevated systemic vascular resistance, hypertension); platelet aggregation and adhesion leading to thrombosis; upregulation of leukocyte and endothelial adhesion molecules leading to enhanced inflammation; vascular stenosis, or restenosis as occurs following balloon angioplasty and stent placement; increased inflammation and tissue damage mediated by reactive oxygen species such as superoxide anion and hydroxyl radical.

As used herein, the phrase "disorder associated with platelet aggregation" generally refers to medical disorders or complications characterized by unwanted or excessive platelet activation and or aggregation. Examples of such disorders or conditions include, though are not limited to, thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures. Additional medical or surgical procedures that may cause unwanted platelet aggregation include, for example, cardiac interventional procedures, tissue or organ transplantation and angioplastic procedures. These procedures include, without limitation, percutaneous transluminal coronary angioplasty with or without placement of an intracoronary stent, cardiac bypass surgery, hemodialysis, extra-corporeal circulation associated with a surgical procedure, intracranial angioplasty, and angioplasty on peripheral arteries. Additional medical conditions that are amendable to treatment in accordance with the presently described methods an compositions include, without limitation, sickle cell anemia crisis, heparin-induced thrombotic thrombocytopenia (HITT), idiopathic thrombotic thrombocytopenia (ITTP), stroke, atherosclerosis, angiogenesis, thrombosis, thromboembolic conditions such as deep venous thrombosis, pulmonary embolism or thrombophlebitis, disseminated intravascular coagulation or thromboembolic syndromes associated with cancer, sepsis, or obstetrical complications, peripheral arterial occlusive disease, acute coronary syndromes such as unstable angina and myocardial infarction, diabetes, or tissue damage caused by phospholipases $A_2$ ($PLA_2$).

The phrase "thrombolytic therapy" or "thrombolysis" refers to a medical treatment or intervention that is performed to promote the pharmacologic dissolution of a clot or a thrombus in a blood vessel. Thrombolytic therapy works by stimulating fibrinolysis by plasmin through infusion of analogs of tissue plasminogen activator, the protein that normally activates plasmin. Formation of blood clots lies at the basis of a number of serious diseases (see below). By breaking down the clot, the disease process can be arrested, or the complications reduced. While other anticoagulants (such as heparin) decrease the "growth" of a clot, thrombolytic agents actively reduce the size of the clot. Disorders for which thrombolytic therapy may be indicated include disorders involving venous thromboses such as, e.g., Deep venous thrombosis (with or without pulmonary embolism; together classified as venous thromboembolism/VTE), Portal vein thrombosis, Renal vein thrombosis, hepatic vein thrombosis (Budd-Chiari syndrome), Paget-Schroetter disease (upper extremity vein), Thoracic outlet syndrome, and disorders involving arterial thromboses such as, e.g., stroke (either thrombotic or embolic), myocardial infarction (usually coronary thrombosis due to rupture of an atherosclerotic plaque), and thoracic outlet syndrome (may precipitate arterial thrombosis as well as venous).

Thrombolytic agents work by activating the enzyme plasminogen, which clears the cross-linked fibrin mesh (the backbone of a clot). This makes the clot soluble and subject to further proteolysis by other enzymes, and restores blood flow over occluded blood vessels. Thrombolysis requires the use of thrombolytic drugs, which are either derived from *Streptomyces* spp. or (more recently) the effect of recombinant technology, where human activators of plasminogen (e.g. tissue plasminogen activator, tPA) are manufactured by bacteria. Some commonly used thrombolytics include streptokinase, urokinase, alteplase (recombinant tissue plasminogen activator or rtPA), reteplase, and tenecteplase.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Pharmaceutically acceptable acid addition salts of the compounds of the invention include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," J. of Pharmaceutical Science, 1977; 66:1 19. The acid addition salts of the basic compounds are prepared by contacting the free base form with a sufficient amount of the desired acid to produce the salt in the conventional manner. The free base form may be regenerated by contacting the salt form with a base, and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention. Lists of suitable salts are found in Remington's Pharmaceutical Sciences, 17th ed., Mack Publishing Company, Easton, Pa., 1985, p. 1418, the disclosure of which is hereby incorporated by reference.

The phrase "combination therapy" (or "co-therapy"), as used herein embraces the administration of one or more carotenoid analogs or derivatives, and of one or more additional agents suitable for the treatment of a disorder associated with platelet aggregation, as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). The term is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a pharmaceutical preparation having a fixed ratio of each therapeutic agent or in multiple preparations for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, additional pharmacologic agents) and non-drug therapies (such as, but not limited to, surgery or radiation treatment).

As used herein, the term "inhibitor," when used in the context of receptor inhibitor, such as in "receptor antagonist," generally refers to a molecule that binds to a specific receptor and decrease their the activity of that receptor by at least 5%, at least 15%, at least 30%, at least 50% or at least 75%. Many drug molecules are receptor antagonists so their discovery and improvement is an active area of research in biochemistry and pharmacology. A medicinal receptor antagonist is often judged by its specificity (its lack of binding to other proteins) and its potency (its dissociation constant, which indicates the concentration needed to inhibit the enzyme). A high specificity and potency ensure that a drug will have few side effects and thus low toxicity.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

As used herein the terms "subject" generally refers to a mammal, and in particular to a human.

The terms "in need of treatment," "in need thereof," "who would benefit from such treatment," or the like when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency. The amount of active ingredient that can be combined with the carrier materials to produce a single dosage form varies depending upon the mammalian host treated and the particular mode of administration.

By "prophylactically effective amount" is meant an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

The term "pharmacologically inert," as used herein, generally refers to a compound, additive, binder, vehicle, and the like, that is substantially free of any pharmacologic or "drug-like" activity.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

As used herein the term "antioxidant" may be generally defined as any of various substances (as beta-carotene, vitamin C, and α-tocopherol) that inhibit oxidation or reactions promoted by Reactive Oxygen Species (ROS) and other radical and non-radical species.

As used herein the term "co-antioxidant" may be generally defined as an antioxidant that is used and that acts in combination with another antioxidant (e.g., two antioxidants that are chemically and/or functionally coupled, or two antioxidants that are combined and function with each another in a pharmaceutical preparation). The effects of co-antioxidants may be additive (i.e., the anti-oxidative potential of one or more anti-oxidants acting additively is approximately the sum of the oxidative potential of each component anti-oxidant) or synergistic (i.e., the anti-oxidative potential of one or more anti-oxidants acting synergistically may be greater than the sum of the oxidative potential of each component anti-oxidant).

Compounds described herein embrace isomers mixtures, racemic, optically active, and optically inactive stereoisomers and compounds.

Platelet Aggregation:

Platelet activation occurs in three stages: (1) exposure to a platelet agonist; (2) generation of second messengers; and (3) initiation of a response cascade that includes cytoskeletal rearrangements, shape change, storage granule release, and ultimately, platelet aggregation. Many factors can initiate platelet activation including arachidonic acid (AA), collagen, plasma protein, thrombin, hormones and products of platelet metabolism, including adenosine diphosphate (ADP) and thromboxane A2. In normal (physiologic) platelets, the initial stimulus by platelet activators is followed by the release of nitric oxide (NO), an inhibitor of platelet aggregation. Dysfunctional platelets, by contrast, generate nitroxidative stress (increased levels of peroxynitrite instead of normal NO levels)—which is followed by platelet aggregation and adhesion to the endothelium of the vasculature. Therefore, the capability of platelets to maintain a normal balance between NO and oxidative stress is critical for the maintenance of normal vascular homeostasis. Such function is essential for preventing thrombotic events that are associated with stroke, heart attack, and peripheral arterial thrombosis.

In addition to platelets, the vascular endothelium modulates vascular tone and platelet function through the release of NO, a potent vasodilator that regulates regional blood flow. A reduction in NO bioavailability contributes to elevated vascular resistance and loss of sensitivity to stimuli of vasodilation, hallmark features of hypertension. Reversal of these pathological effects with antioxidants validates the mechanistic underpinnings of nitric oxide bioavailability in the vasculature. Beyond vasodilation, NO has well characterized vascular benefits, including inhibition of smooth muscle cell proliferation and migration, and reduction in the adhesion and transmigration of leukocytes. In patients at higher risk for cardiovascular disease and its clinical consequences, such as African Americans, there is evidence for reduced NO-mediated vasodilation associated with increased superoxide anion generation in vascular endothelial cells. Thus, agents that directly stimulate NO release may have important therapeutic advantages in the prevention and treatment of cardiovascular disease.

Astaxanthin, a naturally-occurring hydrophobic C40 carotenoid, is a potent physical quencher of singlet oxygen and chain-breaking antioxidant with favorable physicochemical properties. Applicant has recently demonstrated distinct benefits for homochiral (3S,3'S)-astaxanthin in the reduction of the pro-oxidant stress induced by the presence of rofecoxib (VIOXX™) in model cellular membranes (see U.S. patent application Ser. No. 11/417,30, which is commonly owned with the instant application and hereby fully incorporated by reference). Applicant has also recently provided evidence suggesting that non-esterified astaxanthin acts as a selective inhibitor of the cGMP-hydrolyzing enzyme PDE5A by binding to the active site of the enzyme.

When derivatized according to retrometabolic drug design principles, novel carotenoid esters retain the ability to form the carotenoid radical cation, nearly identical to the parent astaxanthin compound. The disodium disuccinate diesters and the tetrahydrochloride dilysinate esters retain and improve the potent superoxide anion scavenging ability of astaxanthin itself. The antioxidant properties carotenoids, including synthetic analogs and derivatives thereof, may be exploited in platelet activation, if levels of NO could be enhanced in the presence of therapeutic concentrations of these potent compounds. Moreover, this activity may be increased further still in the presence of other platelet inhibitors (e.g., antiplatelet agents).

Thienopyridines, such as clopidogrel, effectively interfere with platelet activation by selectively and irreversibly blocking a subunit of the adenosine diphosphate (ADP) receptor ($P2Y_{12}$ receptor). This provides a potent antiplatelet effect that is additive to the inhibition of the thromboxane A2 pathway by aspirin. Thus, the combination of clopidogrel with agents that have complementary benefits on platelet function is a standard, and clinically relevant, approach to reducing atherothrombotic risk.

In accordance with the above, and without being limited to any one particular theory or mechanism of action, it is Applicant's belief that carotenoids and synthetic analogs and derivatives thereof, such as, e.g., homochiral (3S,3'S)-astaxanthin, may increase NO bioavailability in vascular platelets by reducing sources of oxidative stress and peroxynitrite formation. It is also Applicant's belief that carotenoids and synthetic analogs and derivatives thereof may potentiate the bioactivity of NO in platelets, at least in part by inhibiting PDE5A and prolonging the amplitude and duration of cGMP signaling in platelets. It is Applicant's belief further still, that the effects of astaxanthin may be enhanced by the presence of antiplatelet agents such as clopidogrel, due to its complementary physicochemical and pharmacologic properties.

Homochiral astaxanthin and clopidogrel were tested alone, as well as in combination, to determine the main effects of each compound on NO bioavailability and the potential interaction of the 2 complementary agents. The combination of homochiral astaxanthin and clopidogrel enhanced the ability of vascular platelets to release NO in a highly synergistic fashion, with both the kinetics and magnitude of NO release improved by the combination of drugs. The current results indicate a novel approach to reducing atherothrombotic risk with clopidogrel that extends beyond ADP inhibition, and to Applicant's knowledge, represents the first demonstration of the utility of astaxanthin in favorable modulation of platelet activation.

It is an object of the present application to provide a method of preventing or treating disorders or conditions associated with platelet aggregation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms. The method is also directed to a method of preventing, treating or reducing the incidence of: thrombosis, thrombotic events, embolic events or pathological conditions associated with such events, where the thrombosis, thrombotic event or embolic event occurs during or after surgery.

Thus, it is an object of the present application to provide a method of preventing or treating disorders or conditions associated with platelet aggregation; such diseases include venous thrombosis, thrombophlebitis, arterial embolism, coronary and cerebral arterial thrombosis, unstable angina, myocardial infarction, stroke, cerebral embolism, kidney embolisms and pulmonary embolisms. The method is also directed to a method of preventing, treating or reducing the incidence of: thrombosis, thrombotic events, embolic events or pathological conditions associated with such events, where the thrombosis, thrombotic event or embolic event occurs during or after surgery. It is a further object of the present application to provide pharmaceutical compositions suitable for use in the treatment methods described herein. In some embodiments, specific disorders or conditions associated with platelet aggregation that are amenable to treatment in accordance with the present disclosure may include, though are not limited to, thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyperaggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures. Additional medical or surgical procedures that may cause unwanted platelet aggregation include, for example, cardiac interventional procedures, tissue or organ transplantation and angioplastic procedures. These procedures include, without limitation, percutaneous transluminal coronary angioplasty with or without placement of an intracoronary stent, cardiac bypass surgery, hemodialysis, extra-corporeal circulation associated with a surgical procedure, intracranial angioplasty, and angioplasty on peripheral arteries. Additional medical conditions that are amendable to treatment in accordance with the presently described methods and compositions include, without limitation, sickle cell anemia crisis, heparin-induced thrombotic thrombocytopenia (HITT), idiopathic thrombotic thrombocytopenia (ITTP), stroke, atherosclerosis, angiogenesis, thrombosis, thromboembolic conditions such as deep venous thrombosis, pulmonary embolism or thrombophlebitis, disseminated intravascular coagulation or thromboembolic syndromes associated with cancer, sepsis, or obstetrical complications, peripheral arterial occlusive disease, acute coronary syndromes such as unstable angina and myocardial infarction, diabetes, or tissue damage caused by phospholipases $A_2$ ($PLA_2$).

In one embodiment, uses of carotenoid analogs or derivatives, including pharmaceutically acceptable salts thereof, in applications directed to preventing or treating disorders or conditions associated with platelet aggregation may include the preparation of a pharmaceutical composition suitable for such treatment. The pharmaceutical compositions may typically include one or more carotenoid analogs or derivatives in an amount sufficient to increase the biological availability of nitric oxide in a subject administered such a composition.

In one embodiment, uses of carotenoid analogs or derivatives, including pharmaceutically acceptable salts thereof, in applications directed to preventing or treating disorders or conditions associated with platelet aggregation in a subject may include administering to a subject having need for such treatment a therapeutically effective amount of a pharmaceutically acceptable composition comprising a carotenoid analog or derivative.

In an embodiment, uses of carotenoid analogs or derivatives, including pharmaceutically acceptable salts thereof, in applications directed to preventing or treating disorders or conditions associated with platelet aggregation in a subject in a subject may include the preparation of pharmaceutical compositions for use with additional pharmaceutical compositions which, when co-administered, act synergistically to prevent or treat disorders or conditions associated with platelet aggregation in a subject.

In one embodiment, uses of carotenoid analogs or derivatives, including pharmaceutically acceptable salts thereof, in applications directed to preventing or treating disorders or conditions associated with platelet aggregation in a subject may include the preparation of pharmaceutical compositions having at least one carotenoid analog or derivative, in addition to at least one additional composition or medicament suitable for use as preventing or treating disorders or conditions associated with platelet aggregation in a subject, including but not limited to one or more antiplatelet agents. Exemplary though non-limiting antiplatelet agents suitable for use in the presently described embodiments include: anticoagulants; statins; ADP receptor inhibitors (e.g., thienopyridines);

thrombin inhibitors; factor Xa inhibitors; agonists of purinergic receptors; antagonists of CD40 or CD40 ligand (CD40L) or compounds that disrupt (e.g., reduce) the interaction of CD40 and CD40L; eicosanoid related targets (e.g., COX inhibitors, PGE1 agonists, PG synthase inhibitors, TX synthase inhibitors, and TXA2 antagonists); and glycoprotein IIb/IIIa antagonists. Exemplary anticoaglulants suitable for use in accordance with the presently disclosed treatment methods include, e.g., aspirin, warfarin, a combination of aspirin and warfarin. Exemplary non-fractionated or fractionated heparins may include low molecular weight heparins, such as ardeparin, certoparin, dalteparin, enoxaparin, nadroparin, reviparin, or tinazaparin, and those compounds described in WO 97/35592. Exemplary statins suitable for use in accordance with the presently disclosed treatment methods include, e.g., atorvastatin, fluvastatin, lovastatin, pravastatin, or simvastatin. Exemplary ADP receptor inhibitors suitable for use in accordance with the presently disclosed treatment methods include, e.g., clopidogrel, ditazole, pirozadil, sarpogrelate, and ticlopidine. Exemplary thrombin inhibitors suitable for use in accordance with the presently disclosed treatment methods include, e.g., argatroban, dennatan, desirudin, efegatran, inogatran, lepirudin, melagatran, mesoglycan, PEG-r-hirudin, and reviparin. Factor Xa inhibitors include, for example, danaparoid, fondaparinux, and tifacogin. Exemplary fractionated heparins include low molecular weight heparins, such as ardeparin, certoparin, dalteparin, enoxaparin, nadroparin, reviparin, or tinazaparin. Exemplary purinergic receptor agonists suitable for use in accordance with the presently disclosed treatment methods include, e.g., adenosine and adenosine analogs, e.g., 2-(N-pyrazolyl) derivatives of adenosine (e.g., CVT 3146), and 2-propynyl-cyclohexyl-5'-N-ethylcarboxamido derivatives of adenosine (e.g., ATL-146e (4-(3-[6-amino-9-(5-ethylcarbamoyl-3,4-dihydroxy-tetrahydro-furan-2-yl)-9H-purin-2-yl]-prop-2-ynyl)-cyclohexanecarboxylic acid methyl ester), and ATL-193. Exemplary antagonists of CD40 or CD40 ligand (CD40L) or compounds that disrupt (e.g., reduce) the interaction of CD40 and CD40L include monoclonal antibodies (e.g., Antora and IDEC 131 and see US 2002/0031512 and WO01/34649), free CD40, and antisense nucleic acids. Exemplary eicosanoid related targets include alprostadil, beraprost, carbasalate, cloricromene, epoprost, etersalate, iloprost, indobufin, indometacin farnesil, limaprost, ozagrel, pamicogrel, picotamide, ramatroban, terbogrel, and triflusal. Exemplary glycoprotein IIb/IIIa antagonists for use in the methods and compositions of the invention include xemilofiban, abciximab, cromafiban, elarofiban, orbofiban, roxifiban, sibrafiban, RPR 109891, eptifibatide, and tirofiban.

In an embodiment, carotenoids or synthetic derivatives or analogs thereof may be administered to a subject concurrently with at least one additional composition or medicament suitable for use as preventing or treating disorders or conditions associated with platelet aggregation. In an embodiment, carotenoids or synthetic derivatives or analogs thereof may be administered to a subject prior to the commencement of drug therapy with the one or more compositions or medicaments suitable for use as preventing or treating disorders or conditions associated with platelet aggregation. In an embodiment, carotenoids or synthetic derivatives or analogs thereof may be administered to a subject following the commencement of therapy with the one or more additional compositions or medicaments suitable for use as preventing or treating disorders or conditions associated with platelet aggregation.

The carotenoids or synthetic derivatives or analogs thereof may be provided in a single pharmaceutical preparation together with at least one additional composition or medicament suitable for use as preventing or treating disorders or conditions associated with platelet aggregation. Alternatively, the carotenoids or synthetic derivatives or analogs thereof may be provided to a subject in a pharmaceutical preparation that is distinct from that which includes the one or more additional compositions or medicaments suitable for use as preventing or treating disorders or conditions associated with platelet aggregation.

The suitability of any particular composition or medicament for use as treatment for a disorder associated with platelet aggregation can be readily determined by evaluation of its potency and selectivity using methods known to those skilled in the art, followed by evaluation of its toxicity, absorption, metabolism, pharmacokinetics; etc in accordance with standard pharmaceutical practice.

Combination Therapy and Treatments:

As described above, the presently contemplated treatment methods and compositions are not limited solely to the administration of a formulation containing synthetic carotenoid analogs and derivatives as the sole medically active component. On the contrary, equally contemplated are compositions and methods in which the subject carotenoid analogs or derivatives may be administered in conjunction with one or more additional compositions or medicaments suitable for use in preventing or treating disorders or conditions associated with platelet aggregation. Typically, such agents will include at least one antiplatelet agent.

To use the present invention in combination with the administration of a one or more additional compositions or medicaments suitable for use in preventing or treating disorders or conditions associated with platelet aggregation, one may simply administer to a subject a carotenoid analog or derivative composition in combination with the second composition (i.e., an antiplatelet agent) in a manner effective to result in their combined or synergistic actions within the subject. These agents would, therefore, be provided in an amount effective and for a period of time effective to result in their combined presence within the cardiovascular system of the subject. To achieve this goal, the carotenoid analog or derivative composition and one or more additional compositions or medicaments may be administered to the subject simultaneously, either in a single composition, or as two distinct compositions using different administration routes.

In embodiments where the one or more additional compositions or medicaments and carotenoid analog or derivative composition are administered separately to the subject, one would generally ensure that a significant period of time did not expire between the time of each delivery, such that the one or more additional compositions or medicaments and carotenoid analog or derivative composition would still be able to exert an advantageously combined effect on the cardiovascular system. In such instances, it is contemplated that one would contact platelets with both agents within about 5 minutes to about one week of each other and, more preferably, within about 12-72 hours of each other, with a delay time of only about 24-48 hours being most preferred. In some situations, it may be desirable to extend the time period for treatment significantly, where several days (2, 3, 4, 5, 6 or 7) or even several weeks (1, 2, 3, 4, 5, 6, 7 or 8) lapse between the respective administrations. It also is conceivable that more than one administration of either the carotenoid analog or derivative or the one or more additional compositions or medicaments will be desired. To achieve optimal inhibition of platelet aggregation, both agents may be delivered in a combined amount effective to inhibit platelet aggregation, irrespective of the times for administration.

Salts encompassed within the term "pharmaceutically acceptable salts" refer to non-toxic salts of the compounds which are generally prepared by reacting a free base with a suitable organic or inorganic acid or by reacting the acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric add, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric add, embonic add, stearic add, toluenesulfonic acid, methanesulfonic acid or 1-hydroxy-2-naphthoic add, the adds being employed in salt preparation—depending on whether it is a mono- or polybasic acid and depending on which salt is desired—in an equimolar quantitative ratio or one differing therefrom.

As examples of salts with bases are mentioned the lithium, sodium, potassium, calcium, aluminum, magnesium, titanium, ammonium; meglumine or guanidinium salts, here, too, the bases being employed in salt preparation in an equimolar quantitative ratio or one differing therefrom.

It is understood that the active compounds and their pharmaceutically acceptable salts mentioned can also be present, for example, in the form of their pharmaceutically acceptable solvates, in particular in the form of their hydrates.

The pharmaceutical preparation may be administered orally, in the form of a tablet, a capsule, an emulsion, a liquid, or the like. Alternatively, the pharmaceutical preparation may be administered via a parenteral route. A more detailed description of the types of pharmaceutical preparations that are suitable for some embodiments is described in detail below. Some embodiments may be particularly suited timed or sustained release pharmaceutical preparations, in which the preparation is adapted to deliver a known dosage of carotenoids or synthetic derivatives or analogs thereof at or over a predetermined time. In an embodiment, a pharmaceutical preparation may be a "soft drug", in that the compound is active in the derivatized state, and may yield a known carotenoid after metabolic conversion in vivo. In an embodiment, a pharmaceutical preparation may be adapted to one drug, or a portion thereof, before delivering the second drug. For example, a pharmaceutical preparation may be adapted in such a way that at least a portion of the xanthophyll carotenoid or structural analog or derivative thereof is released into the body of a subject before the additional compositions or medicaments are released.

One or more of the additional compositions or medicaments suitable for the treatment of a disorder associated with platelet aggregation for the uses presently contemplated may be formulated as a separate pharmaceutical composition to be administered in conjunction with the subject carotenoid analogs or derivatives as part of a therapeutic regimen, or may be formulated in a single preparation together with the one or more carotenoid analogs or derivatives. Such a composition may be administered orally, parenterally, by inhalation spray, rectally, or topically in dosage unit formulations containing conventional nontoxic pharmaceutically acceptable carriers, adjuvants, and vehicles as desired. Topical administration may involve the use of transdermal administration such as transdermal patches or iontophoresis devices. The term parenteral generally embraces non-oral routes of administration, including but not limited to, subcutaneous injections, intravenous, intramuscular, intrasternal injection, or infusion techniques. Formulation of drugs is discussed in, for example, Hoover, John E., Remington's Pharmaceutical Sciences, Mack Publishing Co., Easton, Pa. 1975. Another discussion of drug formulations can be found in Liberman, H. A. and Lachman, L., Eds., Pharmaceutical Dosage Forms, Marcel Decker, New York, N.Y., 1980.

Therapeutic Kits:

Therapeutic kits comprising the carotenoid analogs or derivatives, either alone or in combination with an additional composition suitable for the treatment of a disorder associated with platelet aggregation are also contemplated herein. Such kits will generally contain, in suitable container means, a pharmaceutically acceptable formulation of at least one carotenoid analog or derivative compound. The kits also may contain other pharmaceutically acceptable formulations, such as those containing components to target the carotenoid analog or derivative compounds to distinct regions of a patient where treatment is needed, or any one or more of a range of drugs which may work in concert with the carotenoid analog or derivative compounds, for example, antiplatelet agents as described above.

The kits may have a single container means that contains the carotenoid analog or derivative compounds, with or without any additional compositions or medicaments, or they may have distinct container means for each desired composition. When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which the medically active agent(s), and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a means by which to administer the pharmaceutical compositions to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

Carotenoids and the Preparation and Use Thereof

In some embodiments, a composition may include one or more carotenoid analogs or derivatives, optionally in combination with one or more additional compositions or medicaments suitable for the treatment of a disorder associated with platelet aggregation. Carotenoid analogs and derivative suitable for use in accordance with the may include carotenoids having the general structure:

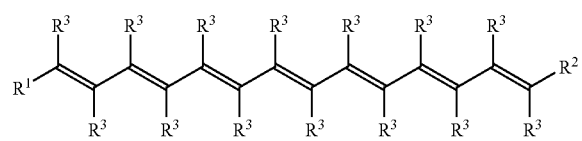

where each R³ is independently hydrogen or methyl, and where R¹ and R² are each independently:

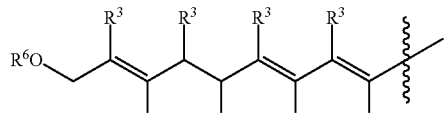

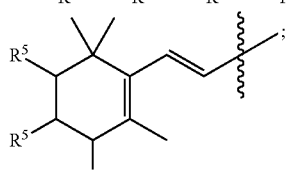

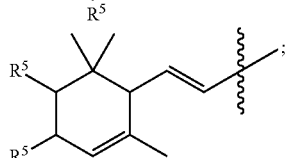

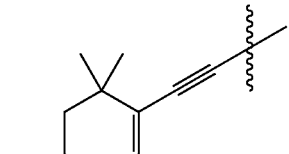

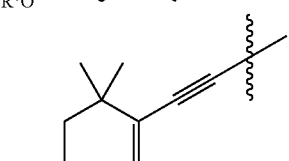

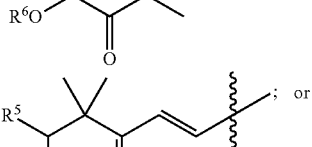

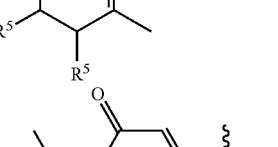

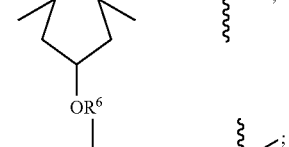

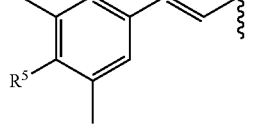

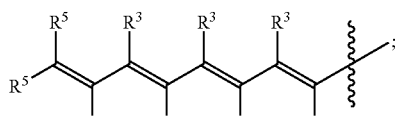

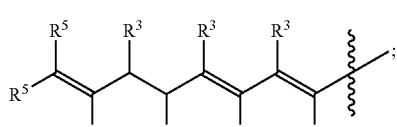

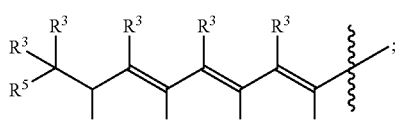

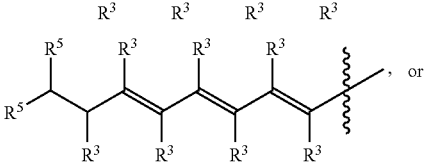, or

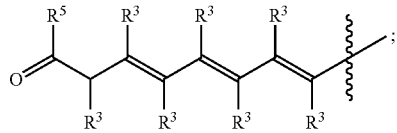

where each R⁵ is independently hydrogen, —CH₃, —OH, —CH₂OH or —OR⁶ wherein at least one R⁵ group in the carotenoid analog or derivative is —OR⁶; wherein each R⁶ is independently: H; alkyl; aryl; -alkyl-N(R⁷)₂; -aryl-N(R⁷)₂; -alkyl-N⁺(R⁷)₃; -aryl-N⁺(R⁷)₃; -alkyl-CO₂R⁹; -aryl-CO₂R⁹; -alkyl-CO₂⁻; -aryl-CO₂⁻; —C(O)-alkyl-N(R⁷)₂; —C(O)-aryl-N(R⁷)₂; —C(O)-alkyl-N⁺(R⁷)₃; —C(O)-aryl-N⁺(R⁷)₃; —C(O)-alkyl-CO₂R⁹; —C(O)-aryl-CO₂R⁹; —C(O)-alkyl-CO₂⁻; —C(O)-aryl-CO₂⁻; —C(O)—(NR⁷)-alkyl-N(R⁷)₂; —C(O)—(NR⁷)-aryl-N(R⁷)₂; —C(O)—(NR⁷)-alkyl-N⁺(R⁷)₃; —C(O)—(NR⁷)-aryl-N⁺(R⁷)₃; —C(O)—(NR⁷)-alkyl-CO₂R⁹; —C(O)—(NR⁷)-aryl-CO₂R⁹; —C(O)—(NR⁷)-alkyl-CO₂⁻; —C(O)—(NR⁷)-aryl-CO₂⁻; —C(O)—(NR⁷)-alkyl-N(R⁷)-alkyl-N(R⁷)₂; —C(O)—OR⁸; —P(O)(OR⁸)₂; —S(O)(OR⁸)₂; —C(O)—[C₆-C₂₄ saturated hydrocarbon]; —C(O)—[C₆-C₂₄ monounsaturated hydrocarbon]; —C(O)—[C₆-C₂₄ polyunsaturated hydrocarbon]; a peptide; a carbohydrate; a nucleoside reside; or a co-antioxidant; where R⁷ is hydrogen, alkyl, or aryl; where R⁸ is hydrogen, alkyl, aryl, benzyl or a co-antioxidant; and where R⁹ is hydrogen, alkyl, aryl, —P(O)(OR⁸)₂, —S(O)(OR⁸)₂, an amino acid, a peptide, a carbohydrate, a nucleoside, or a co-antioxidant.

In some embodiments, carotenoid analogs or derivatives suitable for use with the present compositions, methods and uses may have the structure

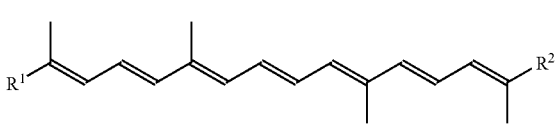

where each R¹ and R² are independently:

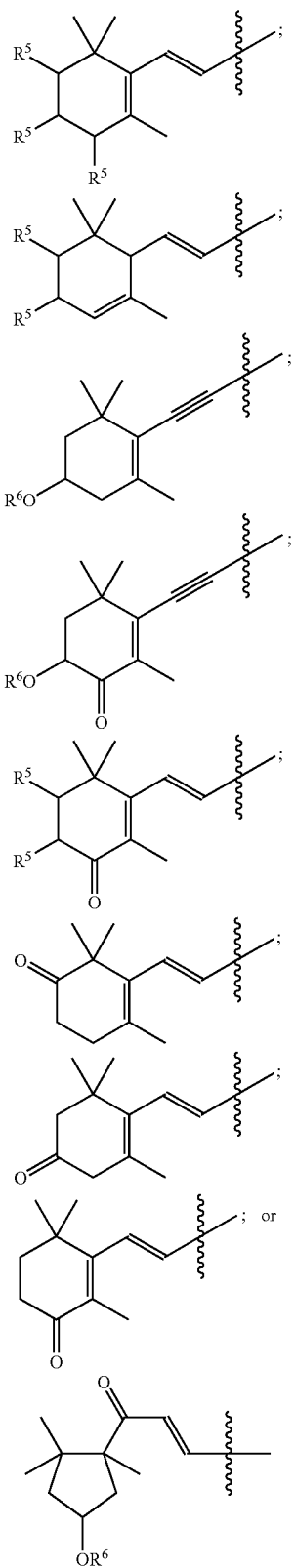

where each R⁵ is independently hydrogen, —CH₃, —OH, —CH₂OH or —OR⁶ wherein at least one R⁵ group in the carotenoid analog or derivative is —OR⁶; wherein each R⁶ is independently: H; alkyl; aryl; -alkyl-N(R⁷)₂; -aryl-N(R⁷)₂; -alkyl-N⁺(R⁷)₃; -aryl-N⁺(R⁷)₃; -alkyl-CO₂R⁹; -aryl-CO₂R⁹; -alkyl-CO₂⁻; -aryl-CO₂⁻; —C(O)-alkyl-N(R⁷)₂; —C(O)-aryl-N(R⁷)₂; —C(O)-alkyl-N⁺(R⁷)₃; —C(O)-aryl-N⁺(R⁷)₃; —C(O)-alkyl-CO₂R⁹; —C(O)-aryl-CO₂R⁹; —C(O)-alkyl-CO₂⁻; —C(O)-aryl-CO₂⁻; —C(O)—(NR⁷)-alkyl-N(R⁷)₂; —C(O)—(NR⁷)-aryl-N(R⁷)₂; —C(O)—(NR⁷)-alkyl-N⁺(R⁷)₃; —C(O)—(NR⁷)-aryl-N⁺(R⁷)₃; —C(O)—(NR⁷)-alkyl-CO₂R⁹; —C(O)—(NR⁷)-aryl-CO₂R⁹; —C(O)—(NR⁷)-alkyl-CO₂⁻; —C(O)—(NR⁷)-aryl-CO₂⁻; —C(O)—(NR⁷)-alkyl-N(R⁷)-alkyl-N(R⁷)₂; —C(O)—OR⁸; —P(O)(OR⁸)₂; —S(O)(OR⁸)₂; —C(O)—[C₆-C₂₄ saturated hydrocarbon]; —C(O)—[C₆-C₂₄ monounsaturated hydrocarbon]; —C(O)—[C₆-C₂₄ polyunsaturated hydrocarbon]; a peptide; a carbohydrate; a nucleoside reside; or a co-antioxidant; where R⁷ is hydrogen, alkyl, or aryl; where R⁸ is hydrogen, alkyl, aryl, benzyl or a co-antioxidant; and where R⁹ is hydrogen, alkyl, aryl, —P(O)(OR⁸)₂, —S(O)(OR⁸)₂, an amino acid, a peptide, a carbohydrate, a nucleoside, or a co-antioxidant.

In some embodiments, each —OR⁶ group may independently be

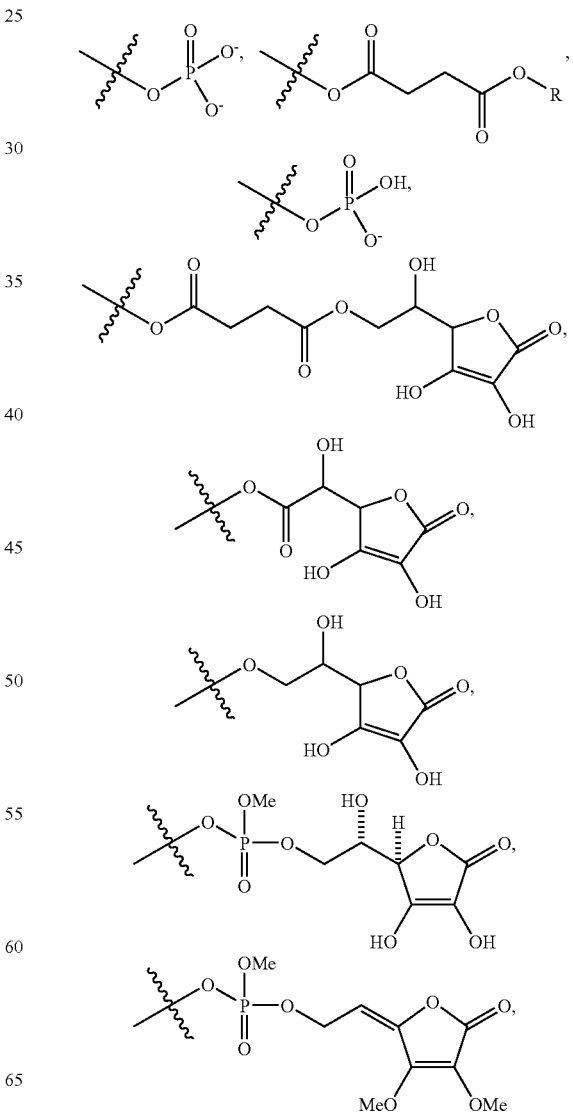

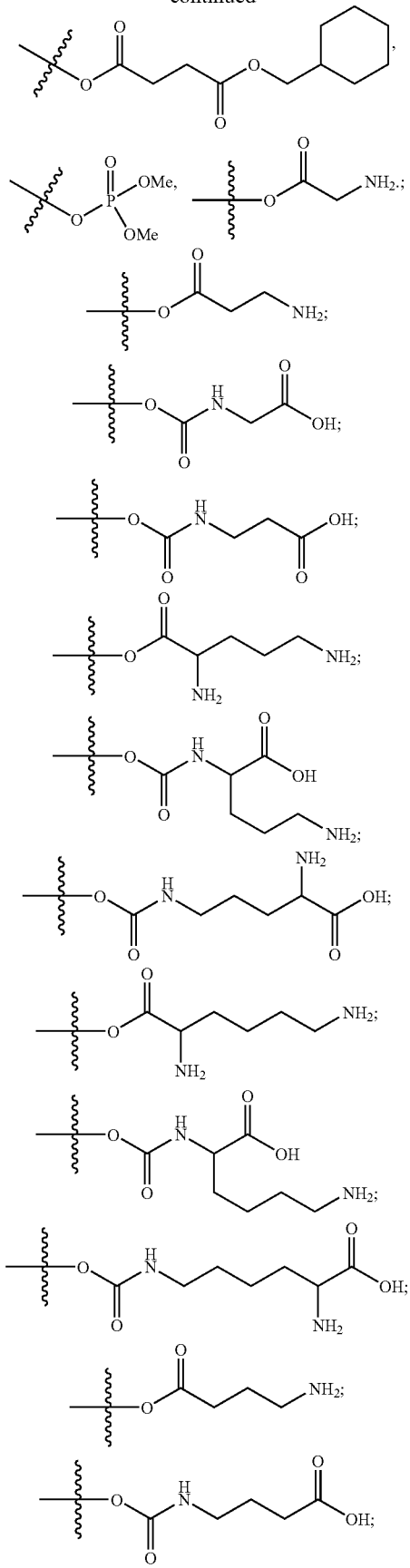

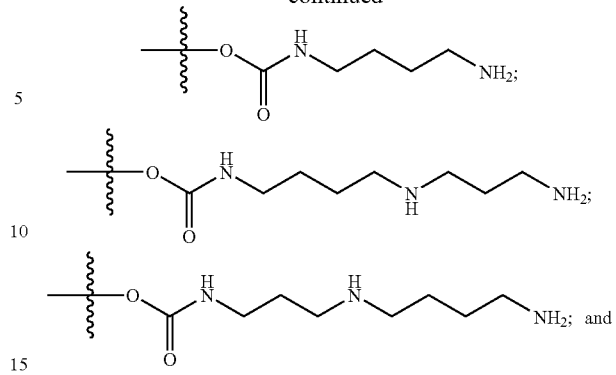

pharmaceutically acceptable salts of any of these compounds, where each R is independently H, alkyl, aryl, benzyl, Group IA metal, or co-antioxidant.

In some embodiments, carotenoid analogs or derivatives suitable for use with the present compositions, methods and uses may have the structure

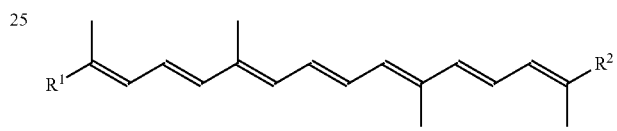

where each $R^3$ is independently hydrogen or methyl, and wherein each $R^1$ and $R^2$ are independently:

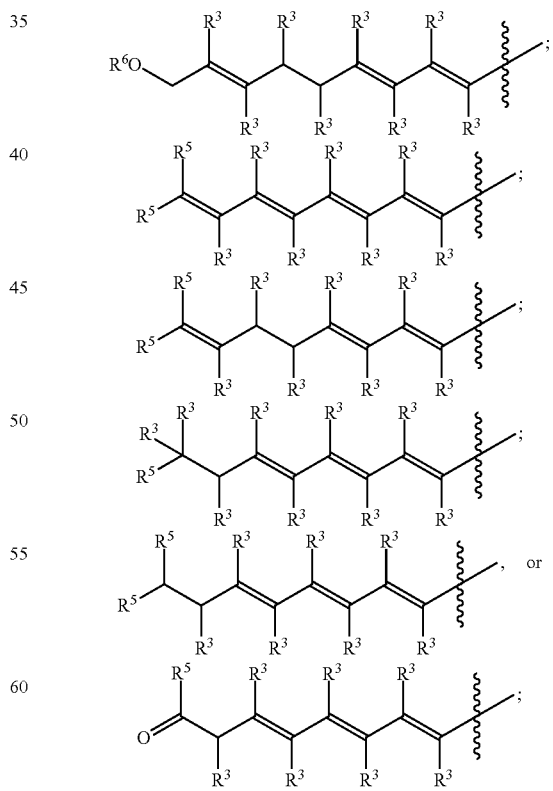

where each $R^5$ is independently hydrogen, —$CH_3$, —OH, —$CH_2OH$ or —$OR^6$ wherein at least one $R^5$ group in the carotenoid analog or derivative is —OR$^6$; wherein each R$^6$ is independently: H; alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where R$^7$ is hydrogen, alkyl, or aryl; where R$^8$ is hydrogen, alkyl, aryl, benzyl or a co-antioxidant; and where R$^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, carotenoid analogs or derivatives suitable for use with the present compositions, methods and uses may have the structure:

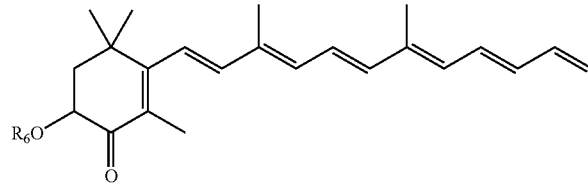

where each R$^5$ is independently hydrogen, —CH$_3$, —OH, —CH$_2$OH or —OR$^6$ wherein at least one R$^5$ group in the carotenoid analog or derivative is —OR$^6$; wherein each R$^6$ is independently: H; alkyl; aryl; -alkyl-N(R$^7$)$_2$; -aryl-N(R$^7$)$_2$; -alkyl-N$^+$(R$^7$)$_3$; -aryl-N$^+$(R$^7$)$_3$; -alkyl-CO$_2$R$^9$; -aryl-CO$_2$R$^9$; -alkyl-CO$_2^-$; -aryl-CO$_2^-$; —C(O)-alkyl-N(R$^7$)$_2$; —C(O)-aryl-N(R$^7$)$_2$; —C(O)-alkyl-N$^+$(R$^7$)$_3$; —C(O)-aryl-N$^+$(R$^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where R$^7$ is hydrogen, alkyl, or aryl; where R$^8$ is hydrogen, alkyl, aryl, benzyl or a co-antioxidant; and where R$^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations may be parenterally administered, upon which the spontaneous self-assembly is overcome by interactions with serum and/or tissue components in vivo.

Some specific embodiments may include phosphate derivatives, succinate derivatives, co-antioxidant derivatives (e.g., Vitamin C, Vitamin C analogs, Vitamin C derivatives, Vitamin E, Vitamin E analogs, Vitamin E derivatives, flavonoids, flavonoid analogs, or flavonoid derivatives), or combinations thereof derivatives or analogs of carotenoids. Flavonoids may include, for example, quercetin, xanthohumol, isoxanthohumol, or genistein. Vitamin E may generally be divided into two categories including tocopherols having a general structure

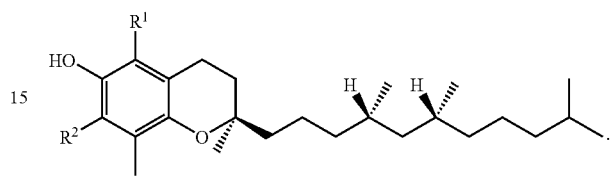

Alpha-tocopherol is used to designate when R$^1$=R$^2$=CH$_3$. Beta-tocopherol is used to designate when R$^1$=CH$_3$ and R$^2$=H. Gamma-tocopherol is used to designate when R$^1$=H and R$^2$=CH$_3$. Delta-tocopherol is used to designate when R$^1$=R$^2$=H.

The second category of Vitamin E may include tocotrienols having a general structure

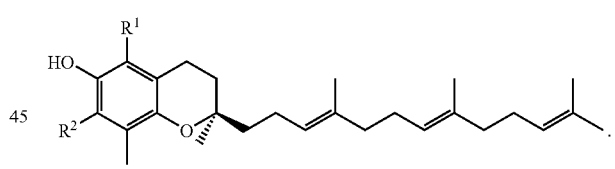

Alpha-tocotrienol is used to designate when R$^1$=R$^2$=CH$_3$. Beta-tocotrienol is used to designate when R$^1$=CH$_3$ and R$^2$=H. Gamma-tocotrienol is used to designate when R$^1$=H and R$^2$=CH$_3$. Delta-tocotrienol is used to designate when R$^1$=R$^2$=H.

Quercetin, a flavonoid, has the structure

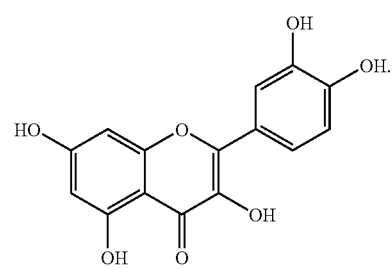

In some embodiments, one or more co-antioxidants may be coupled to a carotenoid or carotenoid derivative or analog. Derivatives of one or more carotenoid analogues may be formed by coupling one or more free hydroxy groups of the co-antioxidant to a portion of the carotenoid.

Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

In some embodiments, carotenoid analogs or derivatives may have increased water solubility and/or water dispersibility relative to some or all known naturally occurring carotenoids. Contradictory to previous research, improved results are obtained with derivatized carotenoids relative to the base carotenoid, wherein the base carotenoid is derivatized with substituents including hydrophilic substituents and/or co-antioxidants.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

In some embodiments, a chemical compound including a carotenoid derivative or analog may have the general structure:

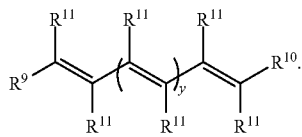

Each $R^{11}$ may be independently hydrogen or methyl. $R^9$ and $R^{10}$ may be independently H, an acyclic alkene with one or more substituents, or a cyclic ring including one or more substituents. y may be 5 to 12. In some embodiments, y may be 3 to 15. In certain embodiments, the maximum value of y may only be limited by the ultimate size of the chemical compound, particularly as it relates to the size of the chemical compound and the potential interference with the chemical compound's biological availability as discussed herein. In some embodiments, substituents may be at least partially hydrophilic. These carotenoid derivatives may be included in a pharmaceutical composition.

In some embodiments, a method for treating a disorder associated with platelet aggregation in a subject may include administering to a subject who would benefit from such treatment a therapeutically effective amount of a pharmaceutically acceptable composition comprising a carotenoid analog or derivative having the structure

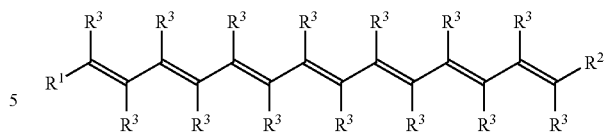

where each $R^3$ is independently hydrogen or methyl, and where $R^1$ and $R^2$ are each independently:

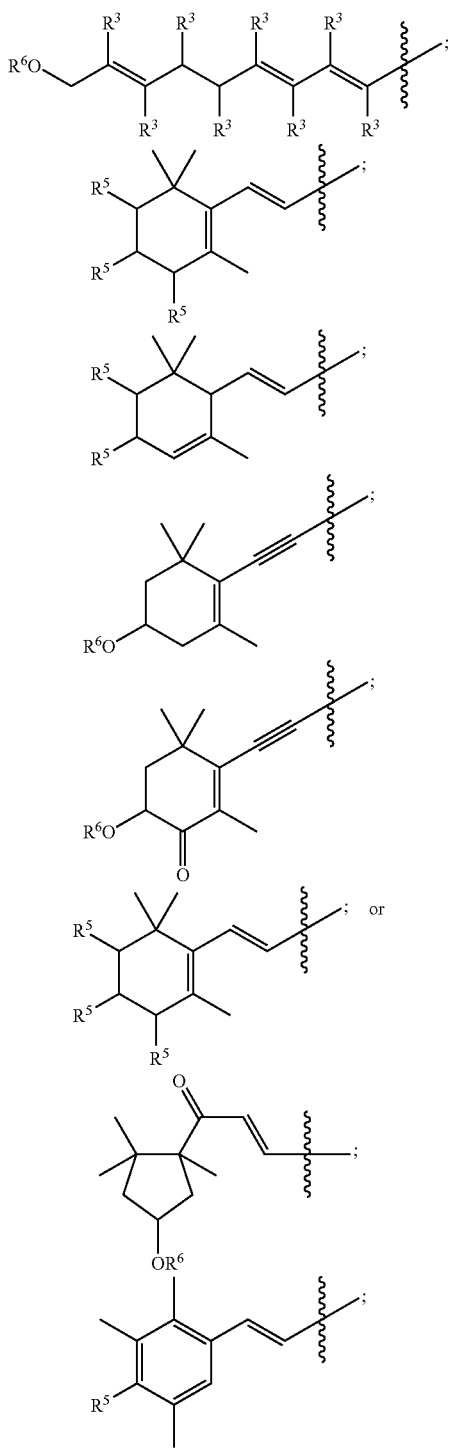

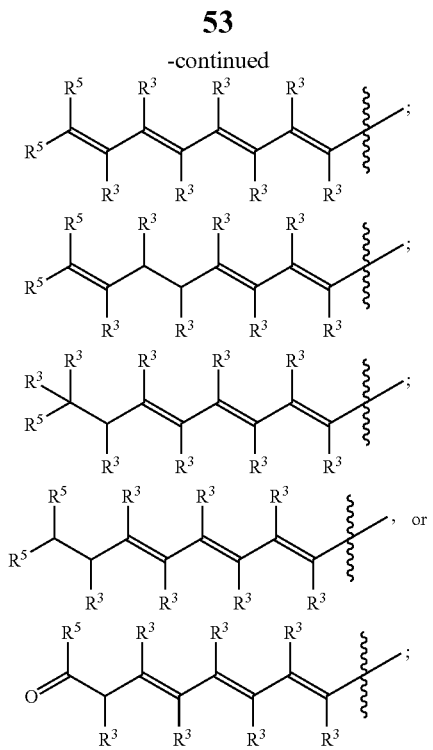

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-N($R^7$)$_2$; -aryl-N($R^7$)$_2$; -alkyl-N$^+$($R^7$)$_3$; -aryl-N$^+$($R^7$)$_3$; -alkyl-CO$_2$R$^9$; -aryl-CO$_2$R$^9$; -alkyl-CO$_2^-$; -aryl-CO$_2^-$; —C(O)-alkyl-N($R^7$)$_2$; —C(O)-aryl-N($R^7$)$_2$; —C(O)-alkyl-N$^+$($R^7$)$_3$; —C(O)-aryl-N$^+$($R^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N($R^7$)$_2$; —C(O)—(NR$^7$)-aryl-N($R^7$)$_2$; —C(O)—(NR$^7$)-alkyl-N$^+$($R^7$)$_3$; —C(O)—(NR$^7$)-aryl-N$^+$($R^7$)$_3$; —C(O)—(NR$^7$)-alkyl-CO$_2$R$^9$; —C(O)—(N-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N($R^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

In some embodiments, a method for treating a disorder associated with platelet aggregation in a subject may include administering to the subject an effective amount of a pharmaceutically acceptable formulation including a synthetic analog or derivative of a carotenoid where each —$OR^6$ group may independently be:

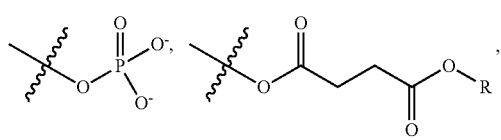

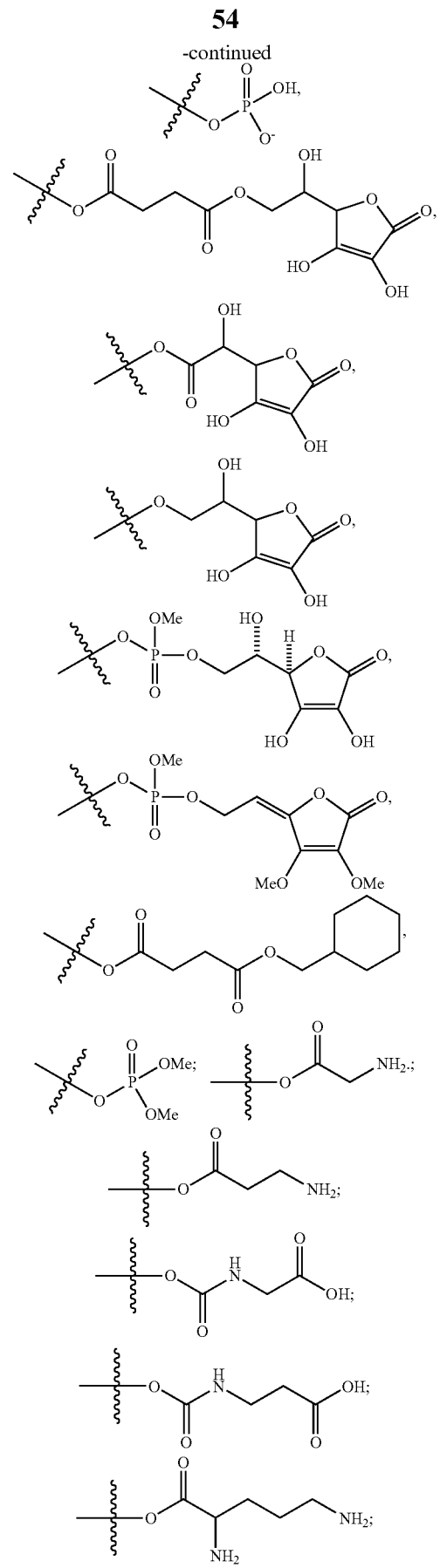

-continued

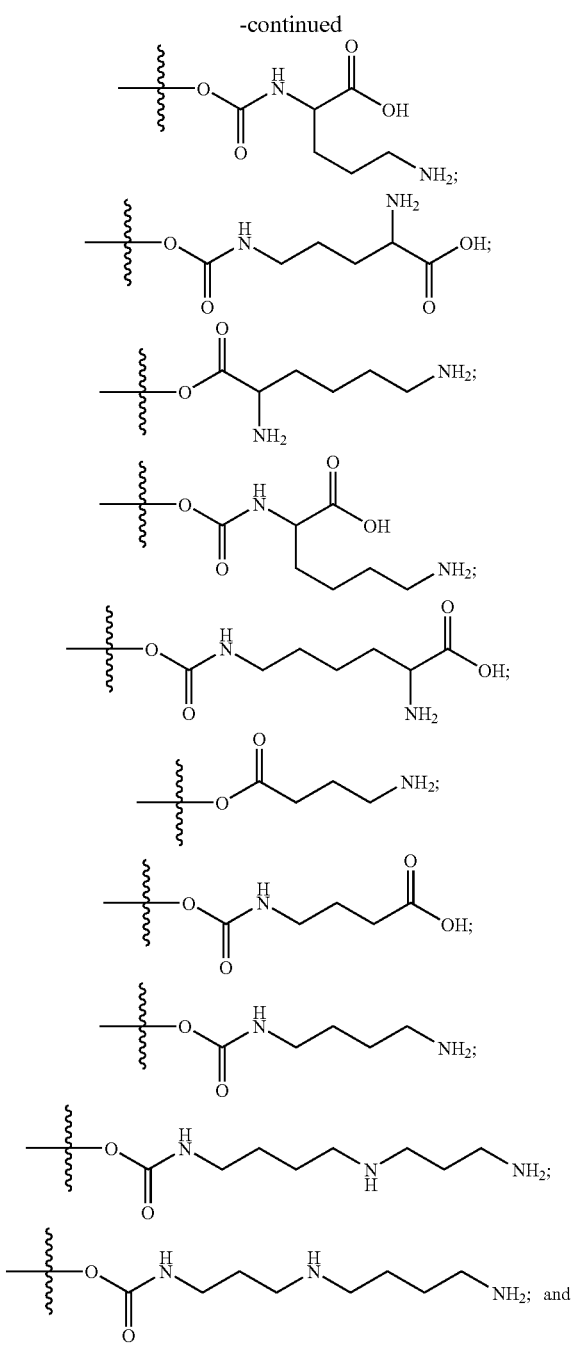

pharmaceutically acceptable salts of any of these compounds, where each R is independently H, alkyl, aryl, benzyl, Group IA metal, or co-antioxidant.

Each co-antioxidant may be independently Vitamin C, Vitamin C analogs, Vitamin C derivatives, Vitamin E, Vitamin E analogs, Vitamin E derivatives, flavonoids, flavonoid derivatives, or flavonoid analogs. Flavonoids include, but are not limited to, quercetin, xanthohumol, isoxanthohumol, or genistein. Selection of the co-antioxidant should not be seen as limiting for the therapeutic application of the current invention.

In some embodiments, a method for treating a disorder associated with platelet aggregation in a subject may include administering to a subject who would benefit from such treatment a therapeutically effective amount of a pharmaceutically acceptable composition comprising a carotenoid analog or derivative. The carotenoid analog or derivative of the carotenoid may have the structure

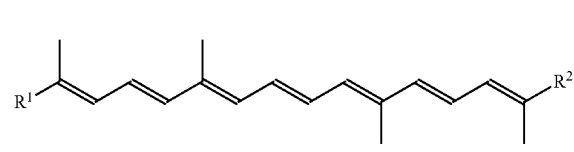

where each $R^1$ and $R^2$ are independently:

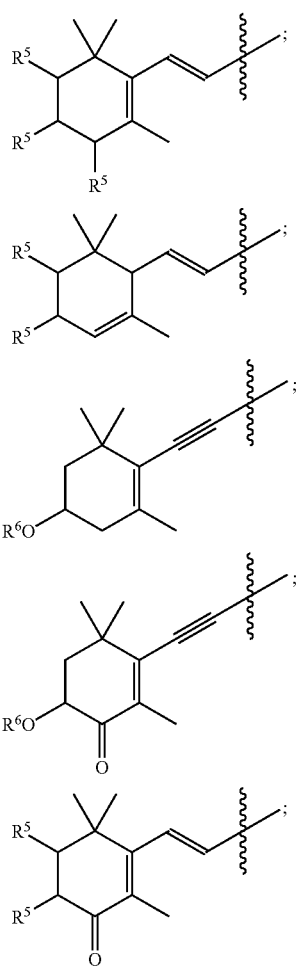

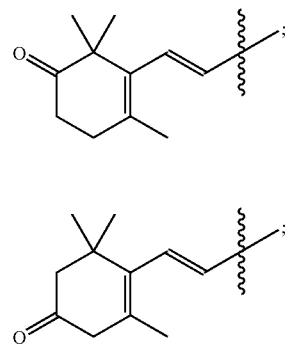

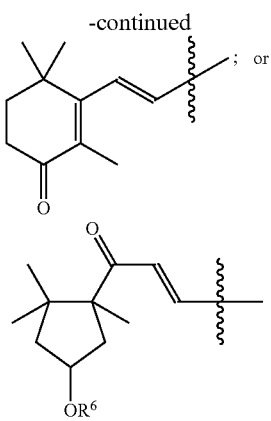

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-$N(R^7)_2$; -aryl-$N(R^7)_2$; -alkyl-$N^+(R^7)_3$; -aryl-$N^+(R^7)_3$; -alkyl-$CO_2R^9$; -aryl-$CO_2R^9$; -alkyl-$CO_2^-$; -aryl-$CO_2^-$; —C(O)-alkyl-$N(R^7)_2$; —C(O)-aryl-$N(R^7)_2$; —C(O)-alkyl-$N^+(R^7)_3$; —C(O)-aryl-$N^+(R^7)_3$; —C(O)-alkyl-$CO_2R^9$; —C(O)-aryl-$CO_2R^9$; —C(O)-alkyl-$CO_2^-$; —C(O)-aryl-$CO_2^-$; —C(O)—($NR^7$)-alkyl-$N(R^7)_2$; —C(O)—($NR^7$)-aryl-$N(R^7)_2$; —C(O)—($NR^7$)-alkyl-$N^+(R^7)_3$; —C(O)—($NR^7$)-aryl-$N^+(R^7)_3$; —C(O)—($NR^7$)-alkyl-$CO_2R^9$; —C(O)—($NR^7$)-aryl-$CO_2R^9$; —C(O)—($NR^7$)-alkyl-$CO_2^-$; —C(O)—(N7)-aryl-$CO_2^-$; —C(O)—($NR^7$)-alkyl-$N(R^7)$-alkyl-$N(R^7)_2$; —C(O)—$OR^8$; —P(O)$(OR^8)_2$; —S(O)$(OR^8)_2$; —C(O)—[$C_6$-$C_{24}$ saturated hydrocarbon]; —C(O)—[$C_6$-$C_{24}$ monounsaturated hydrocarbon]; —C(O)—[$C_6$-$C_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)$(OR^8)_2$, —S(O)$(OR^8)_2$, an amino acid, a peptide, a carbohydrate, a nucleoside, or a co-antioxidant.

In some embodiments, each —$OR^6$ group may independently be

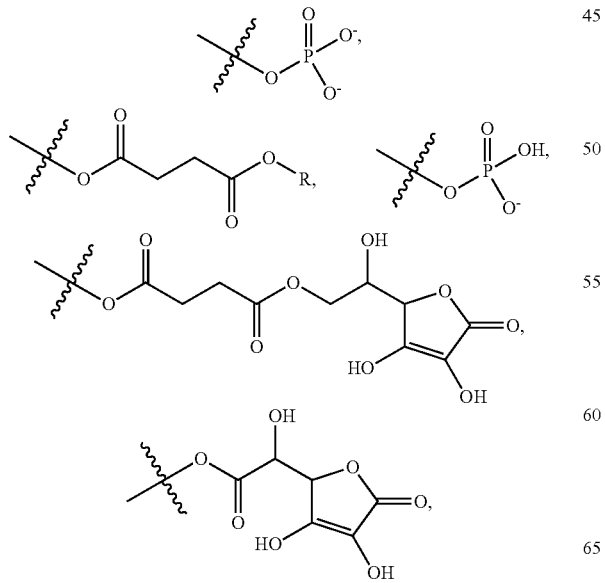

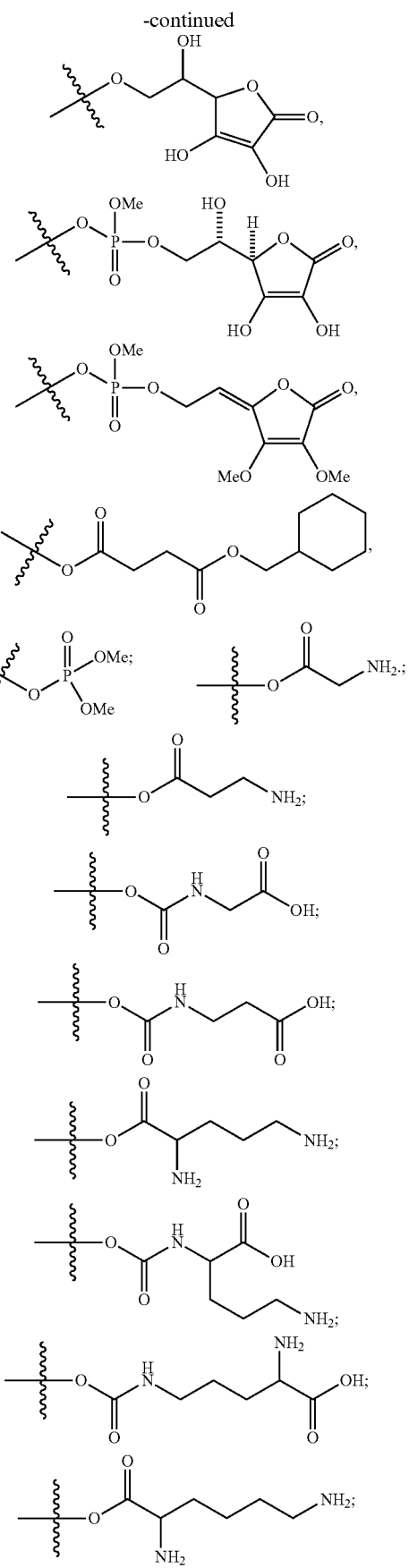

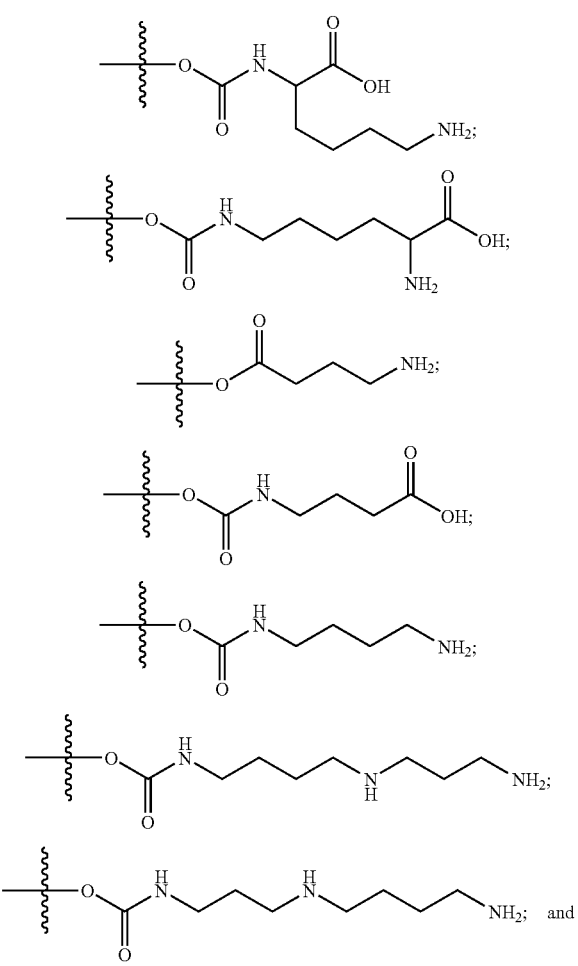

pharmaceutically acceptable salts of any of these compounds, where each R is independently H, alkyl, aryl, benzyl, Group IA metal, or co-antioxidant.

When $R^6$ is an amino acid derivative or a peptide, coupling of the amino acid or the peptide is accomplished through an ester linkage or a carbamate linkage. Specifically, an ester linked amino acid group —$OR^6$ has the general structures:

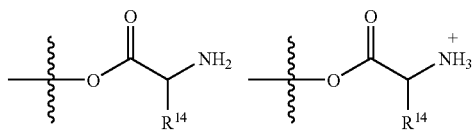

Depending on if the free form of the salt form is desired. A carbamate linked amino acid group —$OR^6$ will have the general structure:

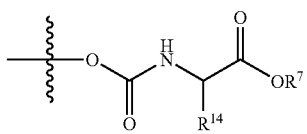

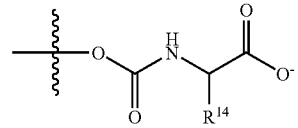

Depending on if the free form of the salt form is desired. For both ester linked and carbamate linked amino acids, the group $R^{14}$ represents an amino acid side chain.

Specifically, $R^{14}$ can be:

—H (glycine); —$CH_3$ (alanine); —$CH(CH_3)$—$CH_3$ (valine); —$CH_2$—$CH(CH_3)$—$CH_3$ (leucine); —$CH(CH_3)$—$CH_2$—$CH_3$ (isoleucine); —$CH_2$-Ph (phenylalanine); —$CH_2$—$CH_2$—S—$CH_3$ (methionine); —$CH_2$—OH (serine); —$CH(CH_3)$—OH (threonine); —$CH_2$—SH (cysteine); —$CH_2$-Ph-OH (tyrosine); —$CH_2$—C(O)—$NH_2$ (aspargine); —$CH_2$—$CH_2$—C(O)—$NH_2$ (glutamine); —$CH_2$—$CO_2H$ (aspartic acid); —$CH_2$—$CH_2$—$CO_2H$ (glutamic acid); —$CH_2$—$CH_2$—$CH_2$—$CH_2$—$NH_2$ (lysine); —$CH_2$—$CH_2$—$CH_2$—$NH_2$ (ornithine); —$CH_2$—$CH_2$—$CH_2$—NH—C(NH)—$NH_2$ (arginine);

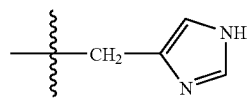

(histidine); and

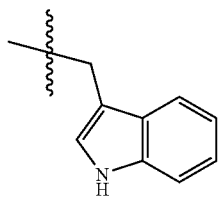

(tryptophan). Amino acid side chains can be in the neutral form (as depicted above) or in a salt form. When $R^{14}$ represents the side chain from the amino acid proline, the following compounds result:

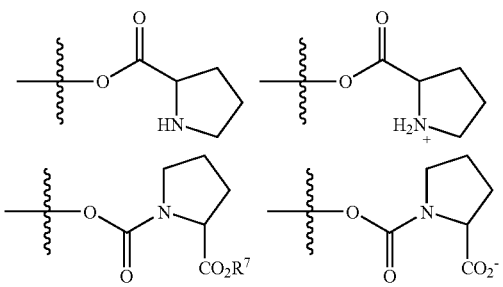

When $R^9$ is an amino acid derivative or a peptide, coupling of the amino acid or the peptide is accomplished through an amide linkage. The amide linkage may be formed between the terminal carboxylic acid group of the linker attached to the xanthophyll carotene and the amine of the amino acid or peptide.

When $R^6$ is a carbohydrate, $R^6$ includes, but is not limited to the following side chains:

—$CH_2$—$(CHOH)_n$—$CO_2H$; —$CH_2$—$(CHOH)_n$—CHO; —$CH_2$—$(CHOH)_n$—$CH_2OH$; —$CH_2$—$(CHOH)_n$—C(O)—$CH_2OH$;

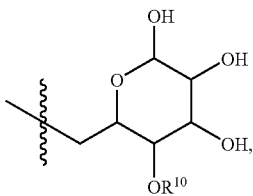

where $R^{10}$ is hydrogen or

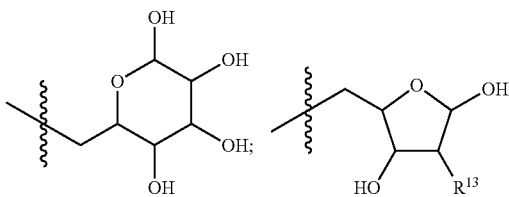

where $R^{13}$ is hydrogen or —OH.

When $R^6$ is a nucleoside, $R^6$ may have the structure:

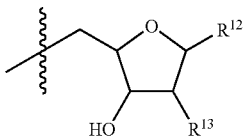

where $R^{12}$ is a purine or pyrimidine base, and $R^{13}$ is hydrogen or —OH.

When $R^6$ is —C(O)—[$C_6$-$C_{24}$ saturated hydrocarbon], the substituent, $R^6$, is derived from coupling of a saturated fatty acid with the carotenoid parent structure. Examples of saturated fatty acids include, but are not limited to: hexanoic acid (caproic acid); octanoic acid (caprylic acid); decanoic acid (capric acid); dodecanoic acid (lauric acid); tridecanoic acid; tetradecanoic acid (myristic acid); pentadecanoic acid; hexadecanoic acid (palmitic acid); heptadecanoic acid (margaric acid); octadecanoic acid (stearic acid); eicosanoic acid (arachidic acid); docosanoic acid (behenic acid); tricosanoic acid; and tetracosanoic acid (lignoceric acid).

When $R^6$ is —C(O)—[$C_6$-$C_{24}$ monounsaturated hydrocarbon], the substituent, $R^6$, is derived from coupling of a monounsaturated fatty acid with the carotenoid parent structure. Examples of monounsaturated fatty acids include, but are not limited to: 9-tetradecenoic acid (myristoleic acid); 9-hexadecenoic acid (palmitoleic acid); 11-octadecenoic acid (vaccenic acid); 9-octadenoic acid (oleic acid); 11-eicosenoic acid; 13-docosenoic acid (erucic acid); 15-tetracosanoic acid (nervonic acid); 9-trans-hexadecenoic acid (palmitelaidic acid); 9-trans-octadecenoic acid (elaidic acid); 8-eicosaenoic acid; and 5-eicosaenoic acid.

When $R^6$ is —C(O)—[$C_6$-$C_{24}$ polyunsaturated hydrocarbon], the substituent, $R^6$, is derived from coupling of a polyunsaturated fatty acid with the carotenoid parent structure. Examples of polyunsaturated fatty acids include, but are not limited to omega-3 polyunsaturated fatty acids, omega-6 polyunsaturated fatty acids; and conjugated polyunsaturated fatty acids. Examples of omega-3 polyunsaturated fatty acids include, but are not limited to: 9,12,15-octadecatrienoic acid (alpha-linolenic acid); 6,9,12,15-octadecatetraenoic acid (stearidonic acid); 11,14,17-eicosatrienoic acid (eicosatrienoic acid (ETA)); 8,11,14,17-eicsoatetraenoic acid (eicsoatetraenoic acid); 5,8,11,14,17-eicosapentaenoic acid (eicosapentaenoic acid (EPA)); 7,10,13,16,19-docosapentaenoic acid (docosapentaenoic acid (DPA)); 4,7,10,13,16,19-docosahexaenoic acid (docosahexaenoic acid (DHA)); 6,9,12,15,18,21-tetracosahexaenoic acid (nisinic acid); 9E,11Z,15E-octadeca-9,11,15-trienoic acid (rumelenic acid); 9E,11Z,13Z,15E-octadeca-9,11,13,15-trienoic acid α-parinaric acid); and all trans-octadeca-9,11,13,15-trienoic acid (β-parinaric acid). Examples of omega-6 polyunsaturated fatty acids include, but are not limited to: 9,12-octadecadienoic acid (linoleic acid); 6,9,12-octadecatrienoic acid (gamma-linolenic acid); 11,14-eicosadienoic acid (eicosadienoic acid); 8,11,14-eicosatrienoic acid (homo-gamma-linolenic acid); 5,8,11,14-eicosatetraenoic acid (arachidonic acid); 13,16-docosadienoic acid (docosadienoic acid); 7,10,13,16-docosatetraenoic acid (adrenic acid); 4,7,10,13,16-docosapentaenoic acid (docosapentaenoic acid); 8E,10E,12Z-octadecatrienoic acid (calendic acid); 10E,12Z-octadeca-9,11'-dienoic acid; 8E,10E,12Z-octadecatrienoic acid (α-calendic acid); 8E,10E,12E-octadecatrienoic acid (β-calendic acid); 8E,10Z,12E-octadecatrienoic acid (jacaric acid); and 5Z,8Z,10E,12E,14Z-eicosanoic acid (bosseopentaenoic acid). Examples of conjugated polyunsaturated fatty acids include, but are not limited to: 9Z, 11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-calendic acid); 8E,10Z,12E-octadecatrienoic acid (jacaric acid); 9E, 11E, 13Z-octadeca-9,11,13-trienoic acid (α-eleostearic acid); 9E, 11E, 13E-octadeca-9,11,13-trienoic acid (β-eleostearic acid); 9Z, 11Z, 13E-octadeca-9,11,13-trienoic acid (catalpic acid); 9E,11Z,13E-octadeca-9,11,13-trienoic acid (punicic acid); 9E, 11Z, 15E-octadeca-9,11,15-trienoic acid (rumelenic acid); 9E, 11Z, 13Z, 15E-octadeca-9,11,13,15-trienoic acid (α-parinaric acid); all trans-octadeca-9,11,13,15-trienoic acid (β-parinaric acid); and 5Z,8Z,10E,12E,14Z-eicosanoic acid (bosseopentaenoic acid).

Specific examples of carotenoid derivatives include, but are not limited to, the following compounds and pharmaceutically acceptable salts of these compounds:

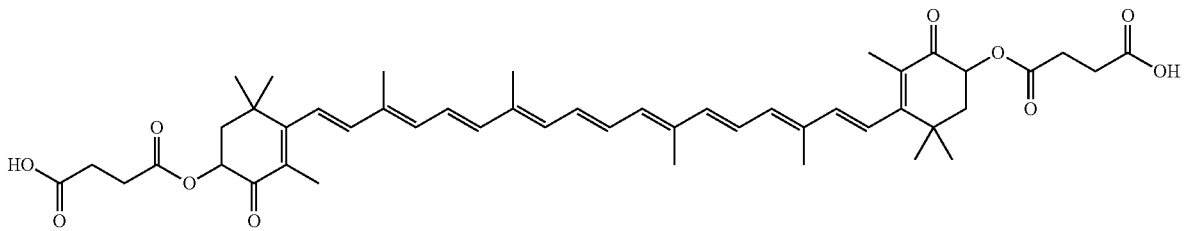

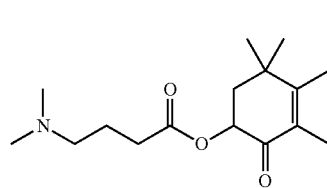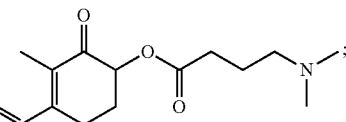
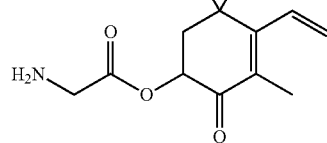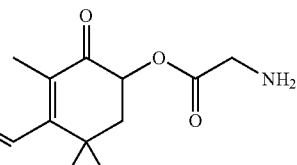
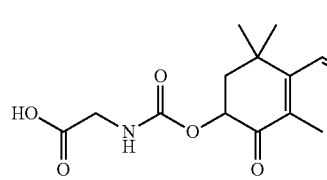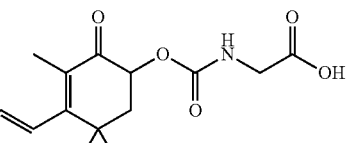
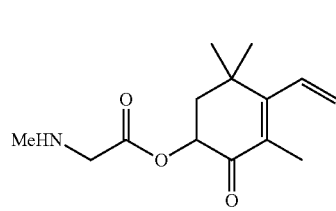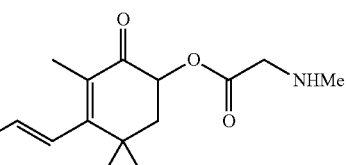
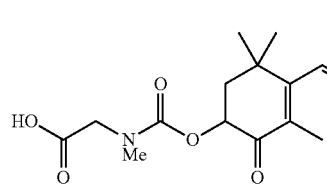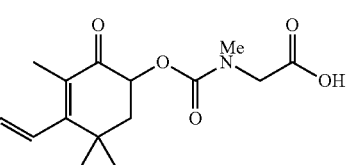
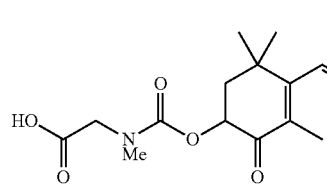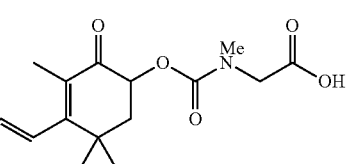
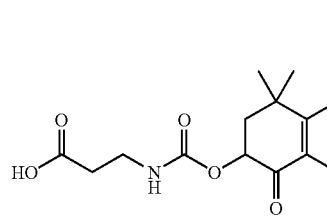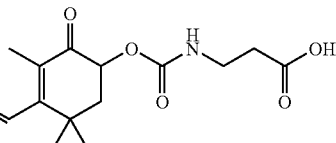

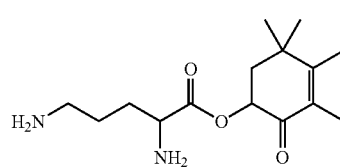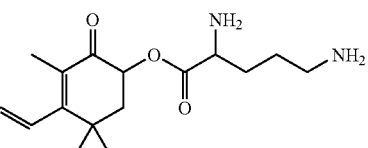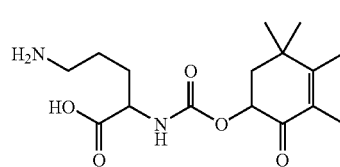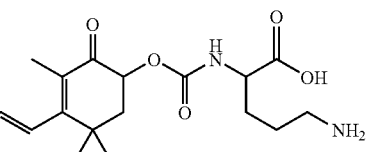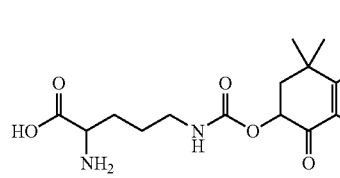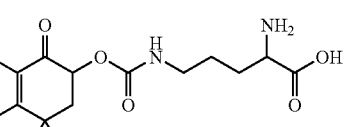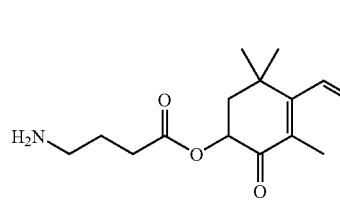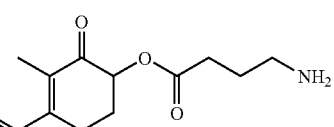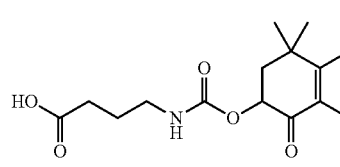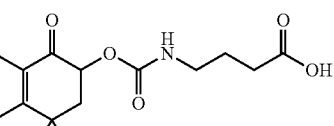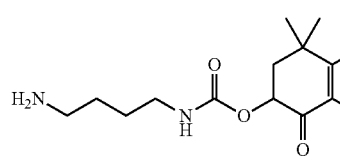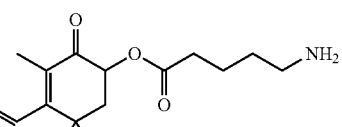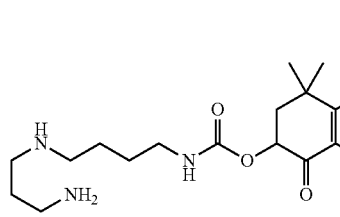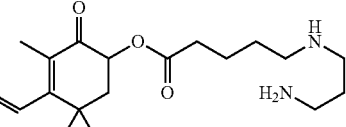

-continued

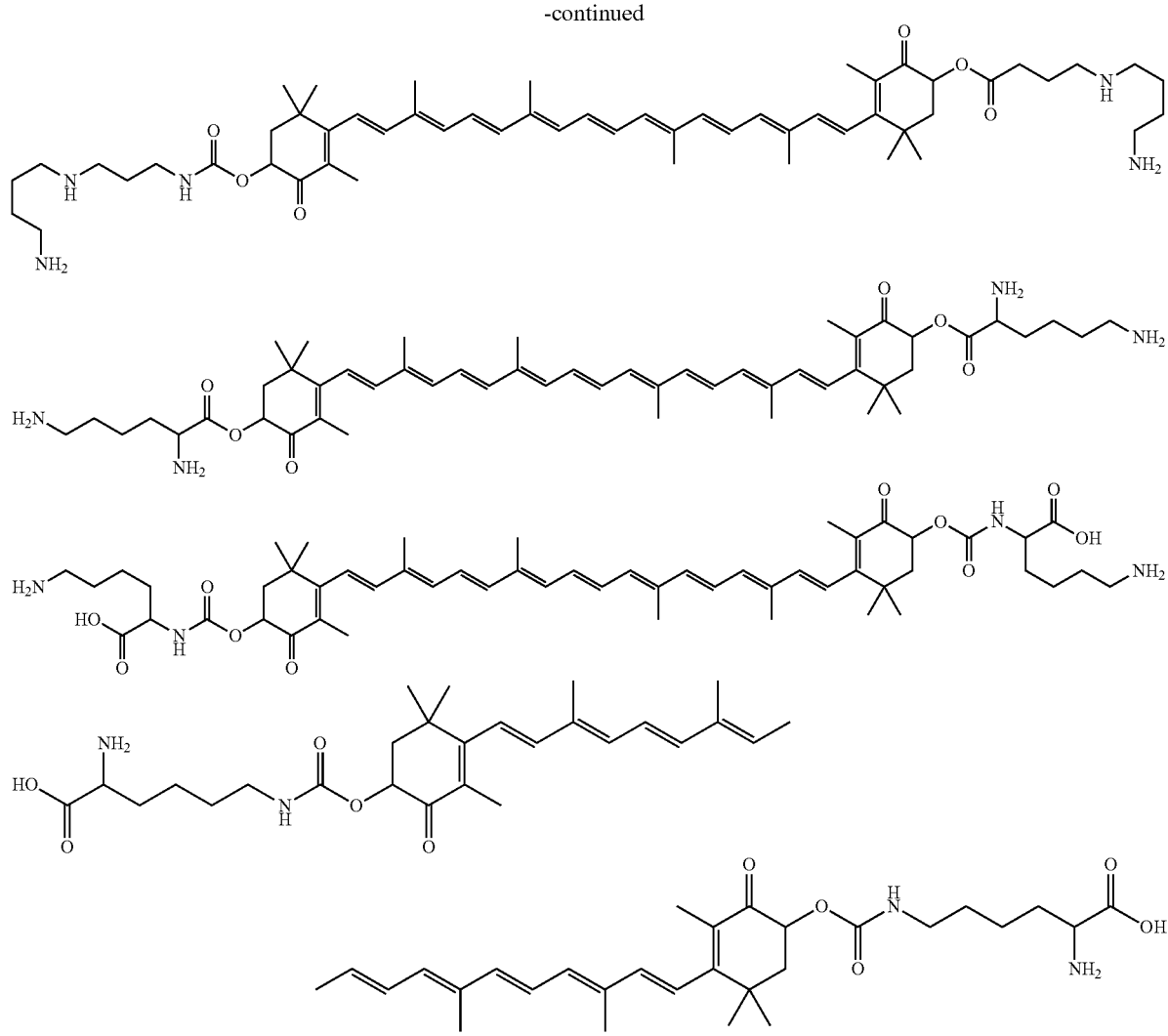

Further details regarding the use and synthesis of carotenoid derivatives and analogs suitable for use in the presently described embodiments may be found in the following U.S. patent documents: U.S. Pat. No. 7,145,025 entitled "STRUCTURAL CAROTENOID ANALOGS FOR THE INHIBITION AND AMELIORATION OF DISEASE" issued Dec. 5, 2006; U.S. Patent Application Publication No. 2005/0113372 entitled "CAROTENOID ANALOGS OR DERIVATIVES FOR THE INHIBITION AND AMELIORATION OF DISEASE"; U.S. Patent Application Publication No. 2005/0075337, entitled "PHARMACEUTICAL COMPOSITIONS INCLUDING CAROTENOID ANALOGS OR DERIVATIVES FOR THE INHIBITION AND AMELIORATION OF DISEASE"; U.S. Patent Application Publication No. 2005/0261254 entitled "CAROTENOID ANALOGS OR DERIVATIVES FOR THE INHIBITION AND AMELIORATION OF INFLAMMATION"; U.S. Patent Application Publication No. 2006/0058269 entitled "CAROTENOID ANALOGS OR DERIVATIVES FOR THE INHIBITION AND AMELIORATION OF INFLAMMATION"; U.S. Patent Application Publication No. 2006/0178538 entitled "METHODS FOR THE SYNTHESIS OF CHIRAL DIHYDROXY INTERMEDIATES USEFUL FOR THE CHIRAL SYNTHESIS OF CAROTENOIDS"; U.S. Patent Application Publication No. 2006/0183947 entitled "METHODS FOR THE SYNTHESIS OF ASTAXANTHIN"; U.S. Patent Application Publication No. 2006/0155150 entitled "METHODS FOR THE SYNTHESIS OF LUTEIN"; U.S. Patent Application Publication No. 2006/0088905 entitled "METHODS FOR THE SYNTHESIS OF ZEAXANTHIN"; U.S. Patent Application Publication No. 2006/0167319 entitled "METHODS FOR THE SYNTHESIS OF UNSATURATED KETONE INTERMEDIATES USEFUL FOR THE SYNTHESIS OF CAROTENOIDS"; U.S. Patent Application Publication No. 2006/0183185 entitled "METHODS FOR THE SYNTHESIS OF ASTAXANTHIN"; U.S. Patent Application Publication No. 2006/0111580 entitled "METHODS FOR THE SYNTHESIS OF CHIRAL DIHYDROXY KETONE INTERMEDIATES USEFUL FOR THE CHIRAL SYNTHESIS OF CAROTENOIDS"; U.S. Patent Application Publication No. 2006/0088904 entitled "METHODS FOR THE SYNTHESIS OF ASTAXANTHIN"; U.S. Patent Application Publication No. 2006/0270590 entitled "REDUCTION IN COMPLEMENT ACTIVATION AND INFLAMMATION DURING TISSUE INJURY BY CAROTENOIDS, CAROTENOID ANALOGS, OR DERIVATIVES THEREOF"; U.S. Patent Application Publication No. 2006/0270589 entitled "CAROTENOIDS, CAROTENOID ANALOGS, OR CAROTENOID DERIVATIVES FOR THE STABILIZATION OR IMPROVEMENT OF VISUAL ACUITY"; U.S. Patent Application Publication No. 2007/0015735 entitled "WATER-DISPERSIBLE CAROTENOIDS, INCLUDING ANALOGS AND DERIVATIVES"; U.S. Patent Application Publication No. 2006/0276372 entitled "CAROTENOIDS, CAROTENOID ANALOGS, OR CAROTENOID DERIVATIVES FOR THE TREATMENT OF PROLIFERATIVE DISORDERS"; U.S. application Ser. No. 11/417,307 entitled "USE OF CAROTENOIDS AND/OR CAROTENOID DERIVATIVES/ANALOGS FOR REDUCTION/INHIBITION OF CERTAIN NEGATIVE EFFECTS OF COX INHIBITORS"; U.S. Ser. No. 60/691,518 entitled "METHODS FOR SYNTHESIS OF CAROTENOIDS, INCLUDING ANALOGS, DERIVATIVES, AND SYNTHETIC AND BIOLOGICAL INTERMEDIATES"; U.S. Patent Application Publication No. 2006/0293545 entitled "METHODS FOR SYNTHESIS OF CAROTENOIDS, INCLUDING ANALOGS, DERIVATIVES, AND SYNTHETIC AND BIOLOGICAL INTERMEDIATES"; U.S. application Ser. No. 11/636,401 entitled "STRUCTURAL CAROTENOID ANALOGS OR DERIVATIVES FOR THE MODULATION OF SYSTEMIC AND/OR TARGET ORGAN REDOX STATUS"; and U.S. Ser. No. 11/699,924 entitled "SYNTHESIS OF CAROTENOID ANALOGS OR DERIVATIVES WITH IMPROVED ANTIOXIDANT CHARACTERISTICS", all of which are commonly owned with the present application and which are hereby expressly incorporated by reference in their entirety as though fully set forth herein.

Water-soluble carotenoid analogs or derivatives may have a water solubility of greater than about 1 mg/mL in some embodiments. In certain embodiments, water-soluble carotenoid analogs or derivatives may have a water solubility of greater than about 5 mg/mL. In certain embodiments, water-soluble carotenoid analogs or derivatives may have a water solubility of greater than about 10 mg/mL. In certain embodiments, water-soluble carotenoid analogs or derivatives may have a water solubility of greater than about 20 mg/mL. In some embodiments, water-soluble carotenoid analogs or derivatives may have a water solubility of greater than about 50 mg/mL.

Naturally occurring carotenoids such as xanthophyll carotenoids of the C40 series, which includes commercially important compounds such as lutein, zeaxanthin, and astaxanthin, have poor aqueous solubility in the native state. Varying the chemical structure(s) of the esterified moieties may vastly increase the aqueous solubility and/or dispersibility of derivatized carotenoids.

In some embodiments, highly water-dispersible $C_{40}$ carotenoid derivatives may include natural source RRR-lutein (β,ε-carotene-3,3'-diol) derivatives. Derivatives may be synthesized by esterification with inorganic phosphate and succinic acid, respectively, and subsequently converted to the sodium salts. Deep orange, evenly colored aqueous suspensions were obtained after addition of these derivatives to USP-purified water. Aqueous dispersibility of the disuccinate sodium salt of natural lutein was 2.85 mg/mL; the diphosphate salt demonstrated a >10-fold increase in dispersibility at 29.27 mg/mL. Aqueous suspensions may be obtained without the addition of heat, detergents, co-solvents, or other additives.

The direct aqueous superoxide scavenging abilities of these derivatives were subsequently evaluated by electron paramagnetic resonance (EPR) spectroscopy in a well-characterized in vitro isolated human neutrophil assay. The derivatives may be potent (millimolar concentration) and nearly identical aqueous-phase scavengers, demonstrating dose-dependent suppression of the superoxide anion signal (as detected by spin-trap adducts of DEPMPO) in the millimolar range. Evidence of card-pack aggregation was obtained for the diphosphate derivative with UV-Vis spectroscopy (discussed herein), whereas limited card-pack and/or head-to-tail aggregation was noted for the disuccinate derivative. These lutein-based soft drugs may find utility in those commercial and clinical applications for which aqueous-phase singlet oxygen quenching and direct radical scavenging may be required.

The absolute size of a carotenoid derivative (in 3 dimensions) is important when considering its use in biological and/or medicinal applications. Some of the largest naturally occurring carotenoids are no greater than about $C_{50}$. This is probably due to size limits imposed on molecules requiring incorporation into and/or interaction with cellular membranes. Cellular membranes may be particularly co-evolved with molecules of a length of approximately 30 nm. In some embodiments, carotenoid derivatives may be greater than or less than about 30 nm in size. In certain embodiments, carotenoid derivatives may be able to change conformation and/or otherwise assume an appropriate shape, which effectively enables the carotenoid derivative to efficiently interact with a cellular membrane.

Although the above structure, and subsequent structures, depict alkenes in the E configuration this should not be seen as limiting. Compounds discussed herein may include embodiments where alkenes are in the Z configuration or include alkenes in a combination of Z and E configurations within the same molecule. The compounds depicted herein may naturally convert between the Z and E configuration and/or exist in equilibrium between the two configurations.

Compounds described herein embrace isomers mixtures, racemic, optically active, and optically inactive stereoisomers and compounds. Carotenoid analogs or derivatives may have increased water solubility and/or water dispersibility relative to some or all known naturally occurring carotenoids. In some embodiments, one or more co-antioxidants may be coupled to a carotenoid or carotenoid derivative or analog.

In some embodiments, carotenoid analogs or derivatives may be employed in "self-formulating" aqueous solutions, in which the compounds spontaneously self-assemble into macromolecular complexes. These complexes may provide stable formulations in terms of shelf life. The same formulations may be parenterally administered, upon which the spontaneous self-assembly is overcome by interactions with serum and/or tissue components in vivo.

Some specific embodiments may include phosphate, succinate, co-antioxidant (e.g., Vitamin C, Vitamin C analogs, Vitamin C derivatives, Vitamin E, Vitamin E analogs, Vitamin E derivatives, or flavonoids), or combinations thereof derivatives or analogs of carotenoids. Flavonoids may include, for example, quercetin, xanthohumol, isoxanthohumol, or genistein. Derivatives or analogs may be derived from any known carotenoid (naturally or synthetically derived). Specific examples of naturally occurring carotenoids which compounds described herein may be derived from include for example zeaxanthin, lutein, lycophyll, astaxanthin, and lycopene.

The synthesis of water-soluble and/or water-dispersible carotenoids (e.g., $C_{40}$) analogs or derivatives—as potential parenteral agents for clinical applications may improve the injectability of these compounds as therapeutic agents, a result perhaps not achievable through other formulation methods. The methodology may be extended to carotenoids with fewer than 40 carbon atoms in the molecular skeleton and differing ionic character. The methodology may be extended to carotenoids with greater than 40 carbon atoms in the molecular skeleton. The methodology may be extended to non-symmetric carotenoids. The aqueous dispersibility of these compounds allows proof-of-concept studies in model systems (e.g., cell culture), where the high lipophilicity of these compounds previously limited their bioavailability and hence proper evaluation of efficacy. Esterification or etherification may be useful to increase oral bioavailability, a fortuitous side effect of the esterification process, which can increase solubility in gastric mixed micelles. These compounds, upon introduction to the mammalian GI tract, are rapidly and effectively cleaved to the parent, non-esterified compounds, and enter the systemic circulation in that manner and form (see, e.g., FIG. 2). The effect of the intact ester and/or ether compound on the therapeutic endpoint of interest can be obtained with parenteral administration of the compound(s). The net overall effect is an improvement in potential clinical utility for the lipophilic carotenoid compounds as therapeutic agents.

In one embodiment, a subject may be administered a pharmaceutical composition comprising a carotenoid analog or derivative. The analog or derivative may be broken down according to the following reaction:

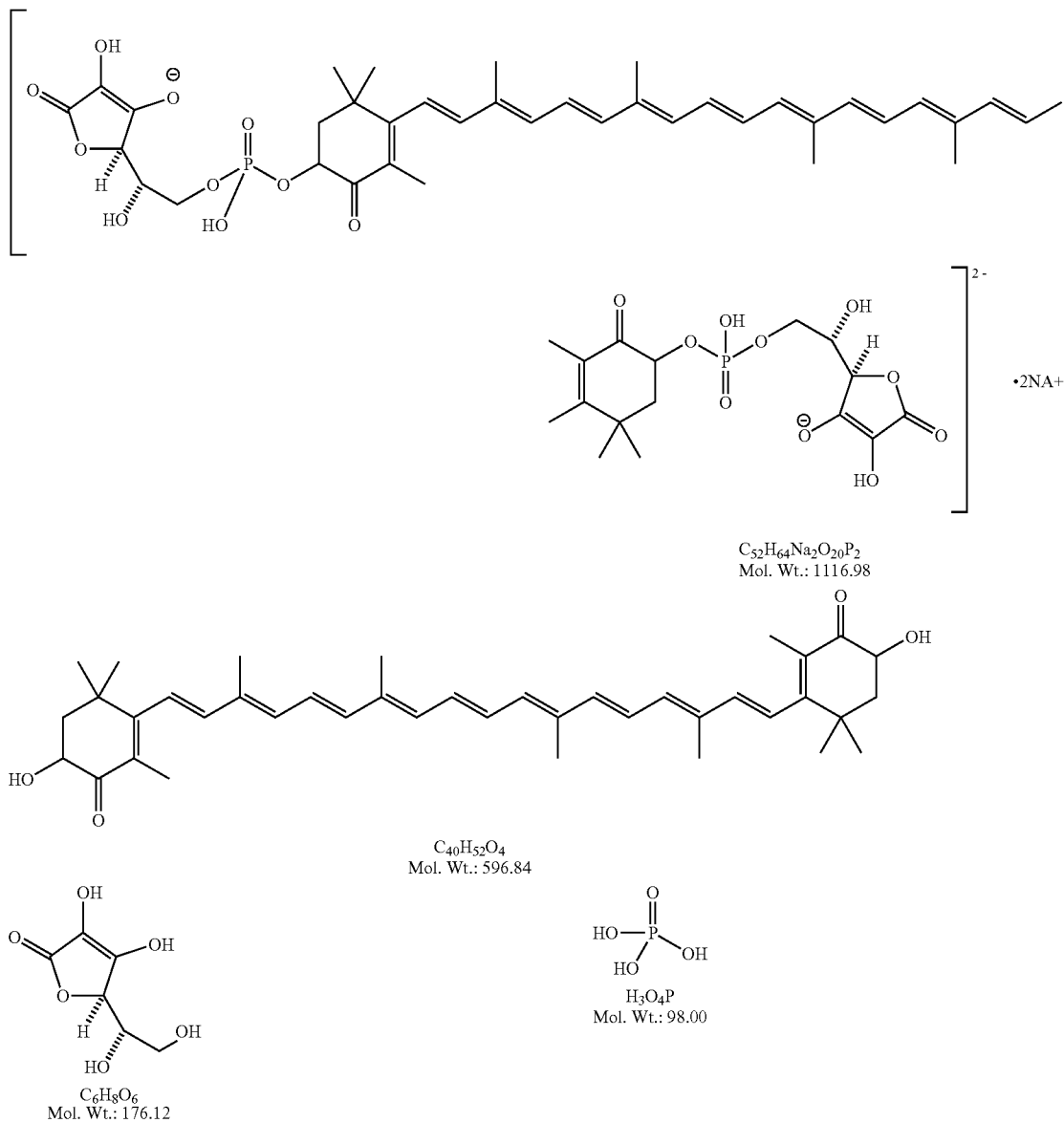

In some embodiments, the principles of retrometabolic drug design may be utilized to produce novel soft drugs from the asymmetric parent carotenoid scaffold (e.g., RRR-lutein (β,ε-carotene-3,3'-diol)). For example, lutein scaffold for derivatization was obtained commercially as purified natural plant source material, and was primarily the RRR-stereoisomer (one of 8 potential stereoisomers). Lutein (Scheme 1) possesses key characteristics—similar to starting material astaxanthin—which make it an ideal starting platform for retrometabolic syntheses: (1) synthetic handles (hydroxyl groups) for conjugation, and (2) an excellent safety profile for the parent compound. As stated above, lutein is available commercially from multiple sources in bulk as primarily the RRR-stereoisomer, the primary isomer in the human diet and human retinal tissue.

In some embodiments, carotenoid analogs or derivatives may have increased water solubility and/or water dispersibility relative to some or all known naturally occurring carotenoids.

In some embodiments, the carotenoid derivatives may include compounds having a structure including a polyene chain (i.e., backbone of the molecule). The polyene chain may include between about 5 and about 15 unsaturated bonds. In certain embodiments, the polyene chain may include between about 7 and about 12 unsaturated bonds. In some embodiments a carotenoid derivative may include 7 or more conjugated double bonds to achieve acceptable antioxidant properties.

In some embodiments, decreased antioxidant properties associated with shorter polyene chains may be overcome by increasing the dosage administered to a subject or patient.

Some embodiments may include solutions or pharmaceutical preparations of carotenoids and/or carotenoid derivatives combined with co-antioxidants, in particular vitamin C and/or vitamin C analogs or derivatives. Pharmaceutical preparations may include about a 2:1 ratio of vitamin C to carotenoid respectively.

In some embodiments, co-antioxidants (e.g., vitamin C) may increase solubility of the chemical compound. In certain embodiments, co-antioxidants (e.g., vitamin C) may decrease toxicity associated with at least some carotenoid analogs or derivatives. In certain embodiments, co-antioxidants (e.g., vitamin C) may increase the potency of the chemical compound synergistically. Co-antioxidants may be coupled (e.g., a covalent bond) to the carotenoid derivative. Co-antioxidants may be included as a part of a pharmaceutically acceptable formulation.

As used herein terms such as "structural carotenoid analogs or derivatives" may be generally defined as carotenoids and the biologically active structural analogs or derivatives thereof. "Derivative" in the context of this application is generally defined as a chemical substance derived from another substance either directly or by modification or partial substitution. "Analog" in the context of this application is generally defined as a compound that resembles another in structure but is not necessarily an isomer. Typical analogs or derivatives include molecules which demonstrate equivalent or improved biologically useful and relevant function, but which differ structurally from the parent compounds. Parent carotenoids are selected from the more than 700 naturally occurring carotenoids described in the literature, and their stereo- and geometric isomers. Such analogs or derivatives may include, but are not limited to, esters, ethers, carbonates, amides, carbamates, phosphate esters and ethers, sulfates, glycoside ethers, with or without spacers (linkers).

As used herein the terms "the synergistic combination of more than one carotenoid or structural analog or derivative or synthetic intermediate of carotenoids" may be generally defined as any composition including one xanthophyll carotenoid or a structural carotenoid analog or derivative or synthetic intermediate combined with one or more different xanthophyll carotenoids or structural carotenoid analogs or derivatives or synthetic intermediates or co-antioxidants, either as derivatives or in solutions and/or formulations.

Certain embodiments may include administering a carotenoid or a structural carotenoid analogs or derivatives or synthetic intermediates alone or in combination to a subject such that disease severity and/or complications associated with a disorder associated with platelet aggregation are thereby at least partially reduced, inhibited and/or ameliorated. The xanthophyll carotenoid or a structural carotenoid analogs or derivatives or synthetic intermediates may be water-soluble and/or water dispersible derivatives. The carotenoid derivatives may include any substituent that substantially increases the water solubility of the naturally occurring carotenoid. The carotenoid derivatives may retain and/or improve the antioxidant properties of the parent carotenoid. The carotenoid derivatives may retain the non-toxic properties of the parent carotenoid. The carotenoid derivatives may have increased bioavailability, relative to the parent carotenoid, upon administration to a subject. The parent carotenoid may be naturally occurring.

Other embodiments may include the administering a composition comprised of the synergistic combination of more than one xanthophyll carotenoid or structural carotenoid analog or derivative or synthetic intermediate to a subject such that disease severity and/or complications associated with a disorder associated with platelet aggregation are thereby at least partially reduced, inhibited and/or ameliorated. The composition may be a "racemic" (i.e. mixture of the potential stereoisomeric forms) mixture of carotenoid derivatives. Included as well are pharmaceutical compositions comprised of structural analogs or derivatives or synthetic intermediates of carotenoids in combination with a pharmaceutically acceptable carrier. In one embodiment, a pharmaceutically acceptable carrier may be serum albumin. In one embodiment, structural analogs or derivatives or synthetic intermediates of carotenoids may be complexed with human serum protein such as, for example, human serum albumin (i.e., HSA) in a solvent. In an embodiment, HSA may act as a pharmaceutically acceptable carrier.

In some embodiments, a single stereoisomer of a structural analog or derivative or synthetic intermediate of carotenoids may be administered to a human subject in order to ameliorate a pathological condition. Administering a single stereoisomer of a particular compound (e.g., as part of a pharmaceutical composition) to a human subject may be advantageous (e.g., increasing the potency of the pharmaceutical composition). Administering a single stereoisomer may be advantageous due to the fact that only one isomer of potentially many may be biologically active enough to have the desired effect.

In some embodiments, compounds described herein may be administered in the form of nutraceuticals. "Nutraceuticals" as used herein, generally refers to dietary supplements, foods, or medical foods that: 1. possess health benefits generally defined as reducing the risk of a disease or health condition, including the management of a disease or health condition or the improvement of health; and 2. are safe for human consumption in such quantity, and with such frequency, as required to realize such properties. Generally a nutraceutical is any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It is important to note that this definition applies to all categories of food and parts of food, ranging from dietary supplements such as folic acid, used for the prevention of spina bifida, to chicken soup, taken to lessen the discomfort of the common cold. This definition also includes a bio-engineered designer vegetable food, rich in antioxidant ingredients, and a stimulant functional food or pharmafood. Within the context of the description herein where the composition, use and/or delivery of pharmaceuticals are described nutraceuticals may also be composed, used, and/or delivered in a similar manner where appropriate.

Dosage and Administration

The carotenoids, carotenoid derivative or analog may be administered at a dosage level up to conventional dosage levels for such derivatives or analogs, but will typically be less than about 2 gm per day. Suitable dosage levels may depend upon the overall systemic effect of the chosen xanthophyll carotenoids, carotenoid derivatives or analogs, but typically suitable levels will be about 0.001 to 50 mg/kg body weight of the patient per day, from about 0.005 to 30 mg/kg per day, or from about 0.05 to 10 mg/kg per day. The compound may be administered on a regimen of up to 6 times per day, between about 1 to 4 times per day, or once per day.

In the case where an oral composition is employed, a suitable dosage range is, e.g. from about 0.01 mg to about 100 mg of a xanthophyll carotenoid, carotenoid derivative or analog per kg of body weight per day, preferably from about 0.1 mg to about 10 mg per kg and for cytoprotective use from 0.1 mg to about 100 mg of a xanthophyll carotenoid, carotenoid derivative or analog per kg of body weight per day.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

In some embodiments, compositions may include all compositions of 1.0 gram or less of a particular structural carotenoid analog, in combination with 1.0 gram or less of one or more other structural carotenoid analogs or derivatives or synthetic intermediates and/or co-antioxidants, in an amount which is effective to achieve its intended purpose. While individual subject needs vary, determination of optimal ranges of effective amounts of each component is with the skill of the art. Typically, a structural carotenoid analog or derivative or synthetic intermediates may be administered to mammals, in particular humans, orally at a dose of 5 to 100 mg per day referenced to the body weight of the mammal or human being treated for a particular disease. Typically, a structural carotenoid analog or derivative or synthetic intermediate may be administered to mammals, in particular humans, parenterally at a dose of between 5 to 1000 mg per day referenced to the body weight of the mammal or human being treated for a particular disease. In other embodiments, about 100 mg of a structural carotenoid analog or derivative or synthetic intermediate is either orally or parenterally administered to treat or prevent disease.

The unit oral dose may comprise from about 0.25 mg to about 1.0 gram, or about 5 to 25 mg, of a structural carotenoid analog. The unit parenteral dose may include from about 25 mg to 1.0 gram, or between 25 mg and 500 mg, of a structural carotenoid analog. The unit intracoronary dose may include from about 25 mg to 1.0 gram, or between 25 mg and 100 mg, of a structural carotenoid analog. The unit doses may be administered one or more times daily, on alternate days, in loading dose or bolus form, or titrated in a parenteral solution to commonly accepted or novel biochemical surrogate marker(s) or clinical endpoints as is with the skill of the art.

In addition to administering a structural carotenoid analog or derivative or synthetic intermediate as a raw chemical, the compounds may be administered as part of a pharmaceutical preparation containing suitable pharmaceutically acceptable carriers, preservatives, excipients and auxiliaries which facilitate processing of the structural carotenoid analog or derivative or synthetic intermediates which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

In some embodiments in which one or more additional medicaments or compositions suitable for the treatment of a disorder associated with platelet aggregation in a subject are administered in conjunction with a carotenoid, a carotenoid derivative or a carotenoid analog, the carotenoid, carotenoid derivative or analog may be administered separately in separate dosage forms or together in a single unit dosage form. Where separate dosage formulations are used, the xanthophylls carotenoid, carotenoid derivative or analog and one or more additional medicaments or compositions may be administered at substantially the same time, i.e., concurrently, or at separately staggered times, i.e., sequentially, and in any order. In certain embodiments the xanthophyll carotenoid, carotenoid derivative or analog the one or more additional medicaments or compositions may be co-administered concurrently on a once-a-day (QD) dosing schedule; however, varying dosing schedules, such as the xanthophyll carotenoid, carotenoid derivative or analog once per day and the one or more additional medicaments or compositions once, twice or more times per day, or the one or more additional medicaments or compositions once per day and the carotenoid derivative or analog once, twice or more times per day, is also encompassed herein. According to certain application(s) of the present embodiments, a single oral dosage formulation comprising the carotenoid derivative or analog and the one or more additional medicaments or compositions may be preferred. In other embodiments, it may be desirable to administer the carotenoid derivative or analog separately from the one or more additional medicaments or compositions. A single dosage formulation will provide convenience for the patient.

The one or more additional medicaments or compositions suitable for the treatment of a disorder associated with platelet aggregation in a subject may be administered at a dosage level up to conventional dosage levels for such compounds. Suitable dosage levels will depend upon the effect and the pharmacological porterties of the chosen additional medicaments or compositions, but typically suitable levels will be between about 0.001 to 50 mg/kg body weight of the patient per day, between about 0.005 to 30 mg/kg per day, or between about 0.05 to 10 mg/kg per day. In some embodiments, the compound may be administered on a regimen of up to 6 times per day, from 1 to 4 times per day, or once per day.

In the case where an oral composition is employed, an exemplary dosage range is, e.g. from about 0.01 mg to about 100 mg of each additional medicament or composition per kg of body weight per day, or from about 0.1 mg to about 10 mg per kg of each additional medicament or composition per kg of body weight per day.

Dosage levels of additional compositions or medicaments suitable for the treatment of disorders associated with platelet aggregation may be on the order of about 0.1 mg to about 10,000 mg of the active ingredient compound are useful in the treatment of the above conditions, with preferred levels of about 1.0 mg to about 1,000 mg. The amount of active ingredient that may be combined with other anticancer agents to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

Treatment dosages generally may be titrated to optimize safety and efficacy. Typically, dosage-effect relationships from in vitro initially can provide useful guidance on the proper doses for patient administration. Studies in animal models also generally may be used for guidance regarding effective dosages for treatment of cancers in accordance with the present invention. In terms of treatment protocols, it should be appreciated that the dosage to be administered will depend on several factors, including the particular agent that is administered, the route administered, the condition of the particular patient, etc. Generally speaking, one will desire to administer an amount of the compound that is effective to achieve a serum level commensurate with the concentrations found to be effective in vitro. Thus, where a compound is found to demonstrate in vitro activity at, e.g., 10 µM, one will desire to administer an amount of the drug that is effective to provide about a 10 µM concentration in vivo. Determination of these parameters is well within the skill of the art.

These considerations, as well as effective formulations and administration procedures are well known in the art and are described in standard textbooks. The following dosages, which are provided by way of illustrative example, may serve as general guidance in the determination of suitable dosage ranges for certain of the additional antiplatelet agent contemplated for use herein. It will of course be readily appreciated by the skilled practitioner that alternative dosages may be employed without departing from the spirit and scope of the presently described embodiments.

Antiplatelet agents suitable for use in the present invention may include glycoprotein (GP) IIb/IIIa receptor antagonists, clopidogrel, ticlopidine, dipyridamole, cilostazol and ASA.

Herein, with respect to all aspects of the invention, the term "antiplatelet agent" is intended to encompass all pharmaceutically acceptable salts, esters and solvate forms, including hydrates, of compounds which have platelet aggregation inhibitory activity as well as pro-drug forms. Those compounds having one or more chiral centers may occur as racemates, racemic mixtures and as individual diastereomers or enantiomers with all such isomeric forms and mixtures thereof being included within the scope of the present disclosure. Any crystalline form of antiplatelet agent forming polymorphs are also intended to be included.

GP IIb/IIIa receptor antagonists inhibit the binding of fibrinogen to the IIb/IIIa platelet receptor site, thereby inhibiting platelet aggregation. Suitable GP IIb/IIIa receptor antagonists are disclosed in WO 99/45913, being herewith incorporated by reference. Suitable GP IIb/IIIa receptor antagonists may be selected from xemilofiban, abciximab, cromafiban, elarofiban, orbofiban, roxifiban, sibrafiban, RPR 109891, eptifibatide, tirofiban, DMP 754, and fradafiban.

Oral dosages of GP IIb/IIIa receptor antagonists when used for the indicated effects may typically range between about 0.001 mg per kg of body weight per day (mg/kg/day) to about 50 mg/kg/day and preferably 0.005 mg/kg/day -20 mg/kg/day, most preferably 0.01 mg/kg/day-10 mg/kg/day. Suitable oral tablets and capsules contain between 0.01 mg and 5 g, preferably between 0.1 mg and 2 g, most preferably between 0.5 mg and 1 mg, for example, 0.5 mg, 1 mg, 5 mg, 10 mg, 150 mg, 250 mg or 500 mg of GP IIb/IIIa receptor antagonists. Oral administration may be in one or divided doses of two, three or four times daily. In an embodiment, a single daily dose may be preferred.

Intravenously, the most preferred doses for GP IIb/IIIa receptor antagonists will range from about 0.5 µg to about 5 mg/kg/minute during a constant rate infusion, to achieve a plasma level concentration during the period of time of administration of between 0.1 ng/ml and 1 µg/ml.

Clopidogrel may be administered orally in a daily dosage of about 25 mg to 500 mg, preferably from 75 mg to 375 mg, and most preferably from 75 mg to 150 mg. For example, a formulation or dosage unit may contain 25 mg, 50 mg, 75 mg, 150 mg, 250 mg or 500 mg of clopidogrel. Oral administration may be in one or divided doses of two, three or four times daily. In an embodiment, a single daily dose may be preferred.

Ticlopidine can be administered orally in a daily dosage of about 50 mg to 1000 mg, preferably from 100 mg to 750 mg, and most preferably from 200 mg to 500 mg. For example, a formulation or dosage unit may contain 50 mg, 100 mg, 200 mg, 250 mg or 500 mg of ticlopidine. Oral administration may be in one or divided doses of two, three or four times daily. In an embodiment, a single daily dose may be preferred.

Cilostazol can be administered orally in a daily dosage of about 50 mg to 500 mg, preferably from 100 mg to 300 mg, and most preferably from 150 mg to 250 mg. For example, a formulation or dosage unit may contain 50 mg, 100 mg, 200 mg, 250 mg or 500 mg of cilostazol. Oral administration may be in one or divided doses of two, three or four times daily. In an embodiment, a single daily dose may be preferred.

Dipyridamole can be administered orally in a daily dosage of about 25 mg to 500 mg, preferably 75 mg to 375 mg, most preferred 75 mg to 150 mg. For long-term treatment it is of advantage to administer repeated doses such as a dose of 25 mg dipyridamole retard or any other instant release formulation three or four times a day. For example, a formulation or dosage unit may contain 25 mg, 50 mg, 75 mg, 150 mg, 250 mg or 500 mg of dipyridamole. Oral administration may be in one or divided doses of two, three or four times daily. In an embodiment, a single daily dose may be preferred.

For parenteral administration dipyridamole could be given in a dosage of 0.5 to 5 mg/kg body weight, preferably 1 to 3.5 mg/kg body weight, during 24 hours as slow i.v. infusion.

Oral dosage amounts of ASA for the indicated effects generally range from about 10 mg to about 325 mg per day. For example, a formulation or dosage unit may contain 10 mg, 20 mg, 50 mg, 75 mg, 80 mg, 100 mg, 150 mg, 250 mg or 325 mg of ASA.

Standard heparin therapy which may be combined with the method of treatment according to the invention comprises the administration of low-molecular-weight heparin (LMWH), unfractionated heparin (UFH), hirudin, hirulog, argatroban, melagatran, lepirudin or bivalirudin, for instance subcutaneous LMWH (e.g. nadroparin 87 IU/kg BID or enoxaparin 1 mg/kg BID) or iv UFH given as an initial bonus of 5000 IU followed by continuous infusion at 1000 IU per hour for 7 days. The activated partial-thromboplastin time (APTT) can be used to assess the degree of anticoagulation in patients receiving iv UFH. Patients can be tested every 12 hours on the first day and every 24 hours subsequently. The APTT should be maintained in the range of 45 to 87 seconds (normal value, 30+/−5 seconds).

Viewed from a second aspect the present invention provides a pharmaceutical composition comprising a therapeutically or prophylactically effective amount of a carotenoid analog or derivative and a therapeutically or prophylactically effective amount of an antiplatelet agent for use in treating a disorder associated with platelet aggregation. The instant pharmaceutical combinations may include a single pharmaceutical dosage formulation containing both a carotenoid analog or derivative and the antiplatelet agent in a pharmaceutical dosage formulation for simultaneous use, as well as a combined preparation or a kit of parts comprising a carotenoid analog or derivative in a pharmaceutical dosage formulation and the antiplatelet agent in a separate pharmaceutical dosage formulation for simultaneous, separate or sequential use.

For instance, the kit of parts embodiment may be an oral dosage formulation of a carotenoid analog or derivative and an oral dosage formulation of ASA. The packaging for the kit may be designed and manufactured in a variety of ways. A preferred example is a blister package containing rows of a carotenoid analog or derivative tablet and an ASA tablet side by side on the same blister card, each of the two tablets in its own blister bubble, with calendar or similar type markings on the card that convey to the user that one "pair" of tablets is to be ingested per day.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, $8^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, New York, 2001).

Pharmaceutical Compositions

Any suitable route of administration may be employed for providing a patient with an effective dosage of drugs of the present invention. For example, oral, rectal, topical, parenteral, ocular, intracranial, pulmonary, nasal, and the like may be employed. Dosage forms may include tablets, troches, dispersions, suspensions, solutions, capsules, creams, ointments, aerosols, and the like. In certain embodiments, it may be advantageous that the compositions described herein be administered orally. In other embodiments, it may be advantageous that the compositions described herein be administered parenterally. In yet other embodiments, it may be advantageous that the compositions described herein be administered locally, at the site of tissue injury.

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well known in the art of pharmacy.

For administration by inhalation, the drugs used in the present invention are conveniently delivered in the form of an aerosol spray presentation from pressurized packs or nebulizers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, and the like.

In practical use, drugs used can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives, and/or co-antioxidants. Optionally, the resulting mixture may be ground and processed. The resulting mixture of granules may be used, after adding suitable auxiliaries, if desired or necessary, to obtain tablets, softgels, lozenges, capsules, or dragee cores.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethyl-cellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") are provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dye stuffs or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas.

Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration include, but are not limited to, aqueous solutions of the active compounds in water-soluble and/or water dispersible form, for example, water-soluble salts, esters, carbonates, phosphate esters or ethers, sulfates, glycoside ethers, together with spacers and/or linkers. Suspensions of the active compounds as appropriate oily injection suspensions may be administered, particularly suitable for intramuscular injection. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Aqueous injection suspensions may contain substances that increase the viscosity of the suspension including, for example, sodium carboxymethyl cellulose, sorbitol, dextran, and/or cyclodextrins. Cyclodextrins (e.g., β-cyclodextrin) may be used specifically to increase the water solubility for parenteral injection of the structural carotenoid analog. Liposomal formulations, in which mixtures of the structural carotenoid analog or derivative with, for example, egg yolk phosphotidylcholine (E-PC), may be made for injection. Optionally, the suspension may contain stabilizers, for example, antioxidants such as BHT, and/or preservatives, such as benzyl alcohol.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian may determine and prescribe the effective amount of the drug required to prevent, counter, or arrest the progress or the development prostate cancer in a subject.

By way of general guidance, the daily oral dosage of each active ingredient, when used for the indicated effects, will range between about 0.001 to 1000 mg/kg of body weight, between about 0.01 to 100 mg/kg of body weight per day, or between about 1.0 to 20 mg/kg/day. Intravenously administered doses may range from about 1 to about 10 mg/kg/minute during a constant rate infusion. Compounds of this invention may be administered in a single daily dose, or the total daily dosage may be administered in divided doses of two, three, or four or more times daily.

The pharmaceutical compositions described herein may further be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

For instance, for oral administration in the form of a tablet or capsule, the pharmacologically active component may be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams or more of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

In an embodiment, the pharmaceutical compositions can be administered locally to the site of neural injury such as by local injection, a minimally invasive drug delivery system, or during a surgical procedure. Alternatively, in some embodiments it may be preferable to administer the composition(s) systemically (such as e.g., by oral or parenteral delivery) such that the concentration of the pharmacologically active agents is sufficient to increase the bioavailability of NO to platelets in the vasculature of the subject.

In an embodiment, the active compounds may be administered to the patient systemically. The term systemic as used herein includes subcutaneous injection; intravenous, intramuscular, intraesternal injection; infusion; inhalation, transdermal administration, oral administration; and intra-operative instillation.

One systemic method involves an aerosol suspension of respirable particles comprising the active compound, which the subject inhales. The active compound would be absorbed into the bloodstream via the lungs, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

The active compounds may also be systemically administered through absorption by the skin using transdermal patches or pads. The active compounds are absorbed into the bloodstream through the skin. Plasma concentration of the active compounds can be controlled by using patches containing different concentrations of active compounds.

Other methods of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs. Additional means of systemic administration of the active compound to the subject may involve a suppository form of the active compound, such that a therapeutically effective amount of the compound reaches the eyes via systemic absorption and circulation.

Further means of systemic administration of the active compound involve direct intra-operative instillation of a gel, cream, or liquid suspension form of a therapeutically effective amount of the active compound.

For topical application, the solution containing the active compound may contain a physiologically compatible vehicle, as those skilled in the art can select, using conventional criteria. The vehicles may be selected from the known pharmaceutical vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

For systemic administration such as injection and infusion, the pharmaceutical formulation is prepared in a sterile medium. The active ingredient, depending on the vehicle and concentration used, can either be suspended or dissolved in the vehicle. Adjuvants such as local anaesthetics, preservatives and buffering agents can also be dissolved in the vehicle. The sterile injectable preparation may be a sterile injectable solution or suspension in a non-toxic acceptable diluent or solvent. Among the acceptable vehicles and solvents that may be employed are sterile water, saline solution, or Ringer's solution.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use may also be presented as chewable gums by embedding the active ingredient in gums so that the active ingredient is slowly released upon chewing.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The pharmaceutical activity of carotenoid analogs and derivatives as well as antiplatelet agents in accordance with the objects of this invention may be assessed using, for example, any of the methods shown below. Other methods for assessing the pharmacological activity of the present formulations are well within the skill level of the ordinary practitioner of the pharmaceutical arts.

The present invention provides that platelet aggregation be inhibited or reduced in vivo by administration of various pharmacologically active agents, or combinations thereof. The present invention describes the utility of various carotenoid analogs and derivatives, various antiplatelet agent, and various combinations of carotenoid analogs and derivative with antiplatelet agents, by addressing a plurality of diseases under which a therapeutic modality is clinically beneficial.

The invention is illustrated further by the following examples which are not to be construed as limiting the invention in scope or spirit to the specific procedures described in them.

Having now described the invention, the same will be more readily understood through reference to the following example(s), which are provided by way of illustration, and are not intended to be limiting of the present invention.

Materials and Methods

Figure 1B:
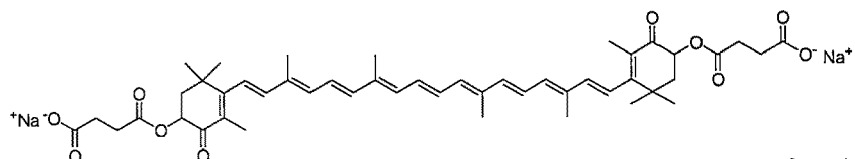
Figure 1C:
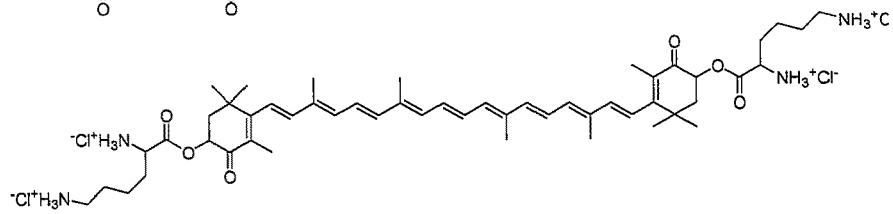
Figures 1, 2:
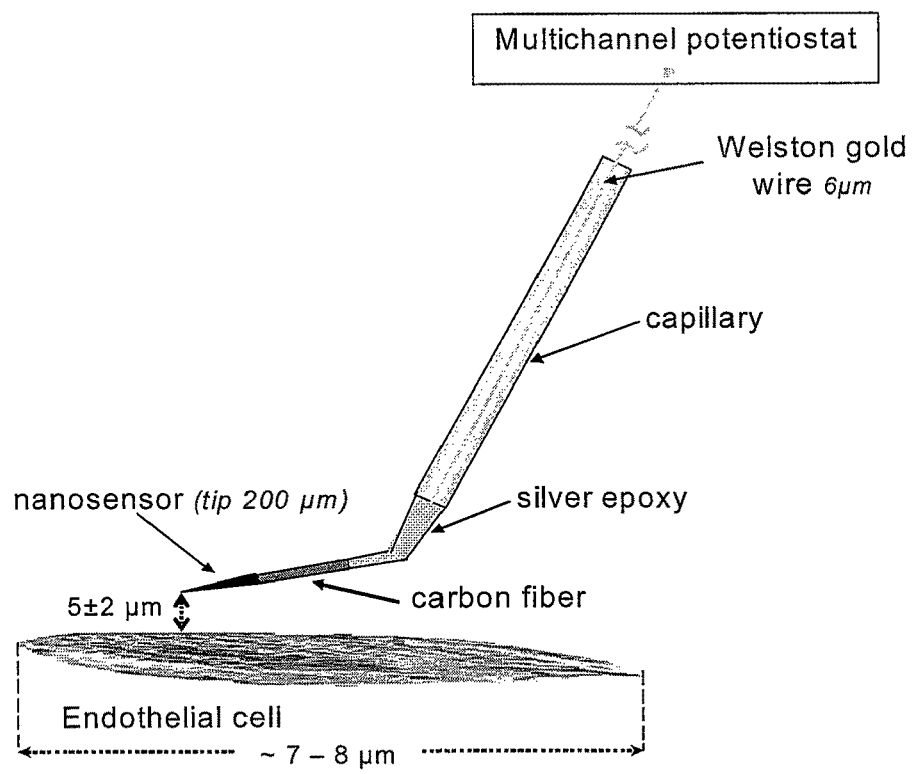
FIG. 2 is a schematic diagram of a nitric oxide nanosensor placed in close proximity to the surface of a single vascular platelet.

Materials:

Non-esterified, all-E astaxanthin (3S,3'S-AST) was synthesized by Synchem, Inc. (Des Plaines, Ill.) and used without further modification (>97% chiral purity by HPLC; FIG. 1). Clopidogrel (2-(2-chlorphenyl)-2-(2,4,5,6,7,7a hexahydrothieno[3,2c]pyridine-5-yl-acetic acid methylester hydrogen sulfate, 7S) was obtained and used without further modification. Both compounds were introduced into the model system using Tyrode-HEPES buffer.

Donors and Endothelial Cell Preparation:

Human umbilical vein endothelial cells (HUVECs) were isolated into primary cultures from white female donors by Clonetics (San Diego, Calif.), essentially as described (Mason et al. 2005). All donors were reported to be healthy and none had pregnancy or prenatal complications. All measurements were recorded in vitro using a sensitive porphyrinic probe, also as previously described. HUVEC cells were grown in Ham's F12K medium with 2 mM L-glutamine adjusted to contain 1.5 g/L sodium bicarbonate and supplemented with 0.1 mg/mL heparin and 0.03-0.05 mg/mL endothelial cell growth supplement (ECGS) plus 10% fetal bovine serum. The HUVEC cells were kept in an atmosphere of elevated $CO_2$ concentration (5%).

Animals and Platelet Isolation:

Wistar-Kyoto (WKY) rats were anaesthetized and blood was collected directly from the heart using a 10 mL syringe that contained 3.8% sodium citrate (9:1, v v$^{-1}$). The blood was centrifuged at 200×g for 15 min at room temperature. The platelet rich plasma (PRP) was then removed by aspiration. The washed platelets were finally suspended in calcium ($Ca^{2+}$)-free Tyrode-HEPES buffer to ascertain that NO was not generated by activation of the aggregating process in the presence of extracellular $Ca^{2+}$. The number of platelets was counted and adjusted to 3.5×10$^8$ per mL with Tyrode-HEPES buffer. The platelets were incubated in an aggregometer with a NO nanosensor (working electrode) placed in the platelet suspension.

Measurement of NO:

As shown in FIG. 2, measurement of NO was conducted using an electrochemical nanosensor. All measurements of NO release were conducted in Hank's balanced salt solution (HBSS) at 37° C. The sensor operated with a three-electrode system: nanosensor (working electrode), saturated calomel electrode (reference electrode), and platinum wire (counter electrode, 0.5 mm diameter). The three electrodes were connected to a potentiostat/galvanostat PAR273. The baseline was stabilized after ~20 s. With a nanoinjector, the test compounds were injected onto the surface of the cells following solubilization in buffer. In experiments with multiple compounds, the compounds were injected simultaneously. The current (amps) proportional to the NO concentration was measured with the sensor, which operated in amperometric mode at a constant potential of 0.63 V. Data were acquired with the use of custom software. Amperograms (current vs. time curves) were recorded with a Guniry FAS1 Femtostat (Warminster, Pa.).

The nanosensor for NO was calibrated using saturated solution (concentration 1.82 mM verified with the coulometric method). Linear calibration curves were constructed for each sensor from 5×10$^{-9}$ to 3×10$^{-6}$ M NO before and after measurements of cell activity. The data were presented as mean±S.D. for each of the triplicate measurements. The data (calculation and plotting) were transferred to Microcal Origin Software (OriginLab Corp., Northampton, Mass.).

The nanosensors (diameter 200-300 nm) were placed in the suspension of 3.5×10$^8$ platelets in 250 μL of buffer A solution of inositol triphosphate (IP3), or a solution of 3S,3'S-AST, clopidogrel, or a combination of 3S,3'S-AST & clopidogrel was added to the platelet suspension with help of a computer controlled nanoinjector. The final concentrations measured were 5 μM and 1 μM, respectively, for 3S,3'S-AST and clopidogrel in each experiment. These suspensions were allowed to incubate with the platelets for 30 min prior to the NO measurement readings being obtained. Current proportional to NO concentration was continuously recorded in time intervals of 40 s. The NO concentration was calculated using current responses obtained from standard NO solution (prepared from 0.176 mM stock solution, saturated aqueous NO solution). Nanosensor approaches allowed us to sample a small volume of solution with suspended platelets and precisely measure the NO concentration (with a detection limit of about $10^{-9}$ M, a response time better than 100 µs, and precision better than ±7%).

Statistical Analysis:

Statistical analyses were performed with the NCSS statistical software package (NCSS 2001 and PASS 2002, Kaysville, Utah). One-way analysis of variance (one-way ANOVA) was followed by Student-Newman-Keuls multiple comparisons post-hoc test. All statistical tests were performed at an $\alpha=0.05$. A sample size of six (6) was evaluated for each treatment group. Data is reported as mean±standard deviation (mean±S.D.).

EXAMPLES

Example 1

Separate versus Combined Effects of Homochiral Astaxanthin and Clopidogrel on Platelet-Dependent Nitric Oxide (NO) Release The effects of inositol triphosphate ($IP_3$) stimulation on total NO release from vascular platelets following incubation with either 5.0 µM homochiral astaxanthin and/or 1.0 µM clopidogrel are shown in FIG. 3 (panels A and B). The separate versus combined effects of these agents on NO release is reported in absolute terms FIG. 3A, as well as the percentage (%) increase over mean control levels in FIG. 3B.

Pre-treatment of vascular platelets with homochiral astaxanthin alone induced a pronounced mean increase in their capacity to generate bioavailable NO by almost two-fold vs. controls (6.6±0.3 to 12.9±0.3 molecules NO×$10^6$/platelet). Albeit to a lesser extent, clopidogrel also caused a marked mean increase in platelet-derived NO release by more than 50% vs. controls (6.6±0.3 to 10.2±0.4 molecules NO×$10^6$/platelet). Significant main effects of monotherapy, then, were seen for each agent.

Figure 4:
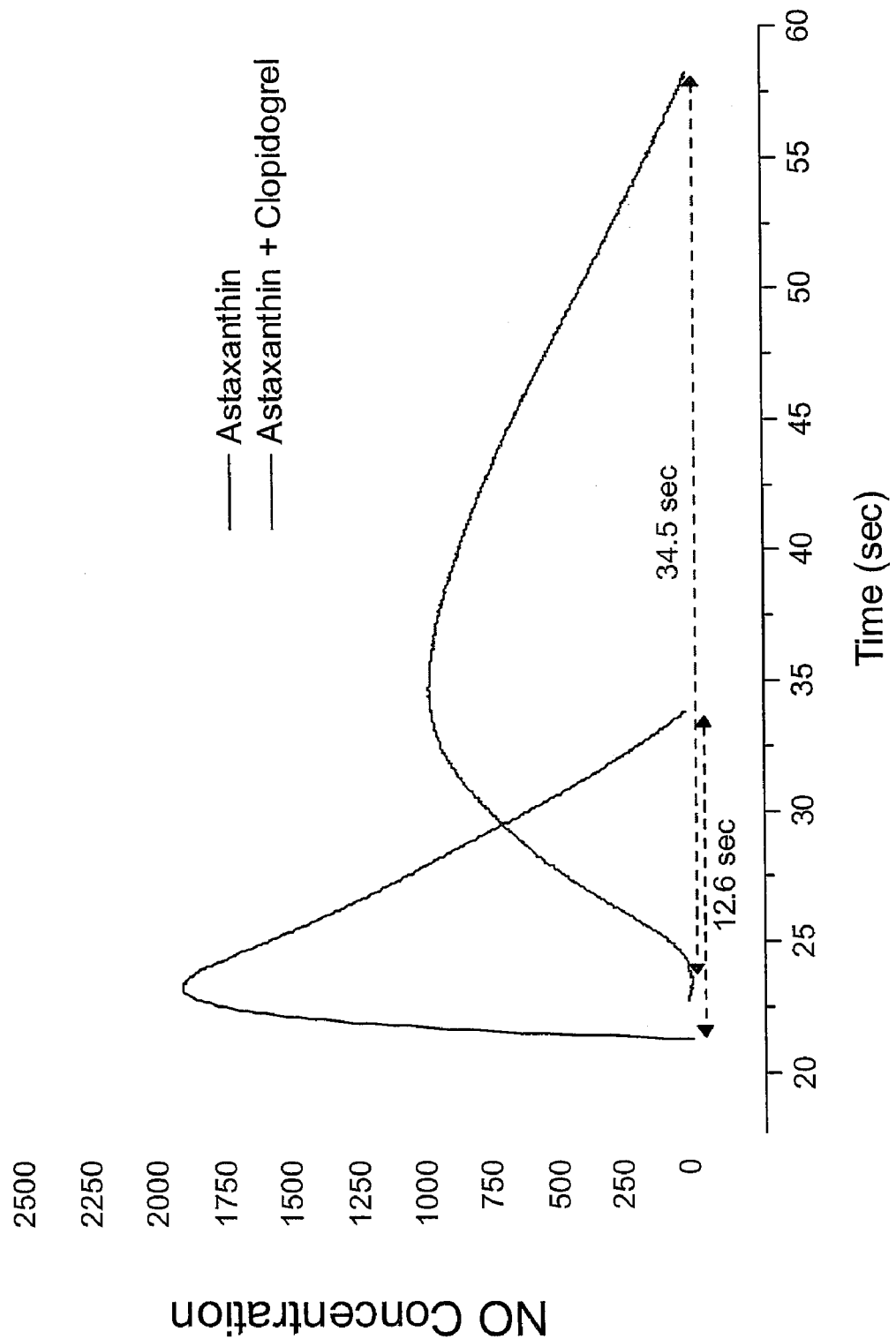
FIG. 4 shows representative amperograms of platelet-derived nitric oxide release following incubation with 3S,3'S-Astaxanthin alone and in combination with clopidogrel.

Synergy is observed with after the administration of both compounds; the relative increase in NO produced by the combination exceeded that of astaxanthin alone and clopidogrel alone, supporting a co-formulation strategy for the two compounds. The absolute mean amounts of NO produced by the combination exceeded that of homochiral astaxanthin alone by more than 75%, and clopidogrel alone by more than two-fold (panel 3A). When standardized as a mean % increase, the relative increase in NO produced by the combination exceeded that of homochiral astaxanthin alone by more than 2-fold, and exceeded that of clopidogrel alone by more than 4-fold (panel 3B). The amperogram that describes the relationship for NO release with time was also distinct for the combination, as evidenced by more sustained production with time (34 s), as compared to only astaxanthin (13 s; FIG. 4). This resulted in a greater net production of NO. These findings indicate an important and statistically significant synergistic benefit for homochiral astaxanthin and clopidogrel with respect to platelet-derived NO production that may indicate complementary mechanisms of action on this cellular process.

Example 2

Turning to FIG. 4, representative inositol triphosphate ($IP_3$)-stimulated amperograms of platelet-derived nitric oxide (NO) release following 15 min incubation with 3S,3'S-AST (5.0 µM) alone (black line) and in combination with clopidogrel (1.0 µM; blue line) are shown. More sustained production over time (34 s) is observed with the combination when compared to the amperogram of 3S,3'S-AST alone (13 s), resulting in greater overall net production of NO with the combination.

Example 3

Figure 5:
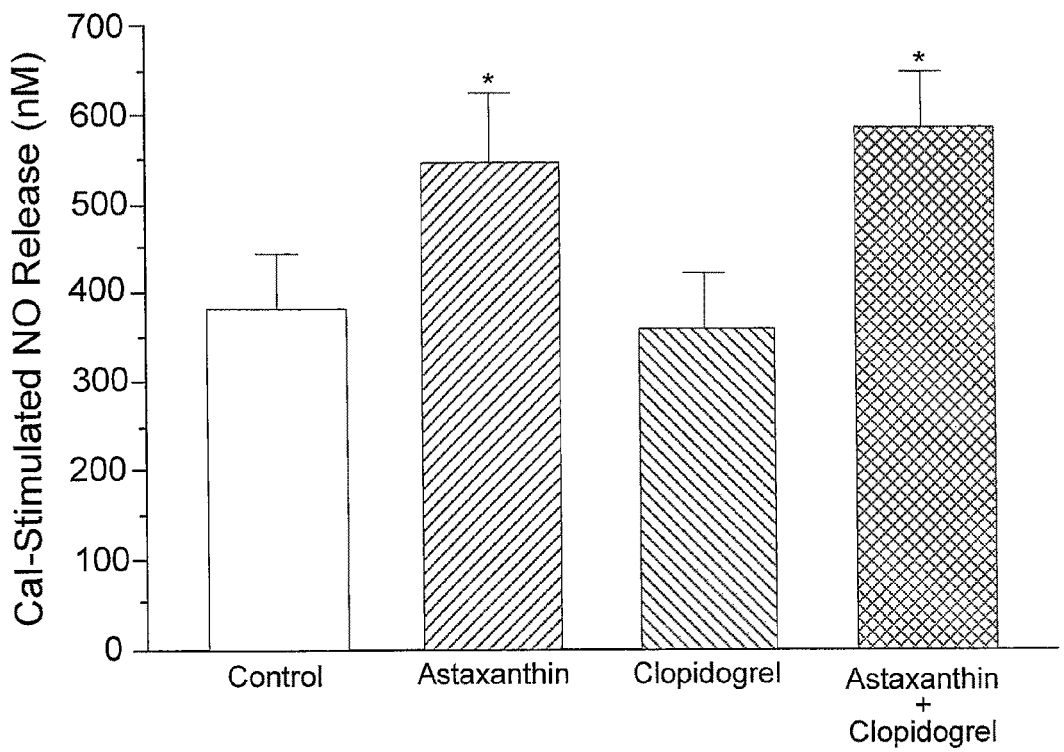
FIG. 5. shows the effects on calcium ionophore (CaI)-stimulated total nitric oxide release from human umbilical vein endothelial cells following incubation with homochiral astaxanthin and clopidogrel, either alone or in combination.

FIG. 5 shows the effects on calcium ionophore (CaI)-stimulated total nitric oxide release (nM) from human umbilical vein endothelial cells (HUVEC) following incubation with homochiral astaxanthin (3S,3'S-AST; 5.0 µM) and clopidogrel (1.0 µM), either alone or in combination. Statistically significant increases in NO release were seen after treatment with homochiral astaxanthin alone or in combination with clopidogrel (*$p<0.001$ versus controls and clopidogrel-treated cells). Treatment with clopidogrel alone did not significantly change NO release from HUVEC, and no additional significant increase was seen after combination with homochiral astaxanthin.

Example 4

Figure 6:
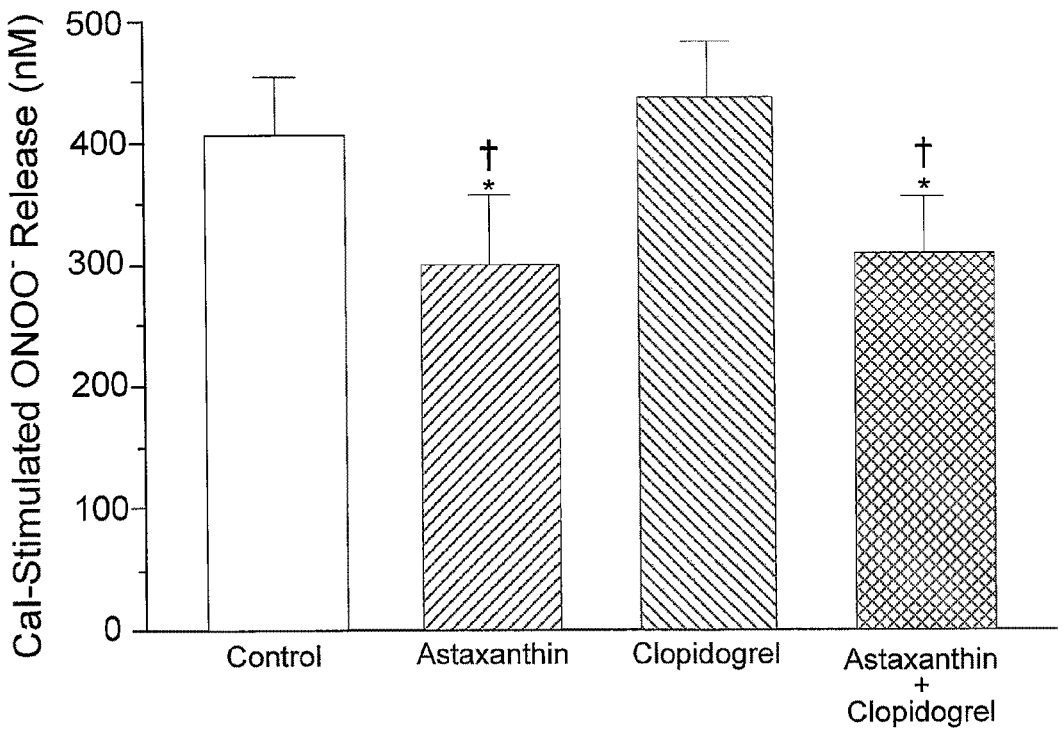
FIG. 6 shows the effects on calcium ionophore (CaI)-stimulated total peroxynitrite release from human umbilical vein endothelial cells following incubation with homochiral astaxanthin and clopidogrel, either alone or in combination.

FIG. 6 shows the effects on calcium ionophore (CaI)-stimulated total peroxynitrite ($OONO^-$) release (nM) from human umbilical vein endothelial cells (HUVEC) following incubation with homochiral astaxanthin (3S,3'S-AST; 5.0 µM) and clopidogrel (1.0 µM), either alone or in combination. Statistically significant decreases in peroxynitrite release were seen after treatment with homochiral astaxanthin (*$p<0.01$ versus controls and †$p<0.001$ versus clopidogrel-treated cells). Treatment with clopidogrel alone did not significantly change peroxynitrite release from HUVEC, and no additional significant decrease was observed after combination with homochiral astaxanthin.

Example 5

Figure 7:
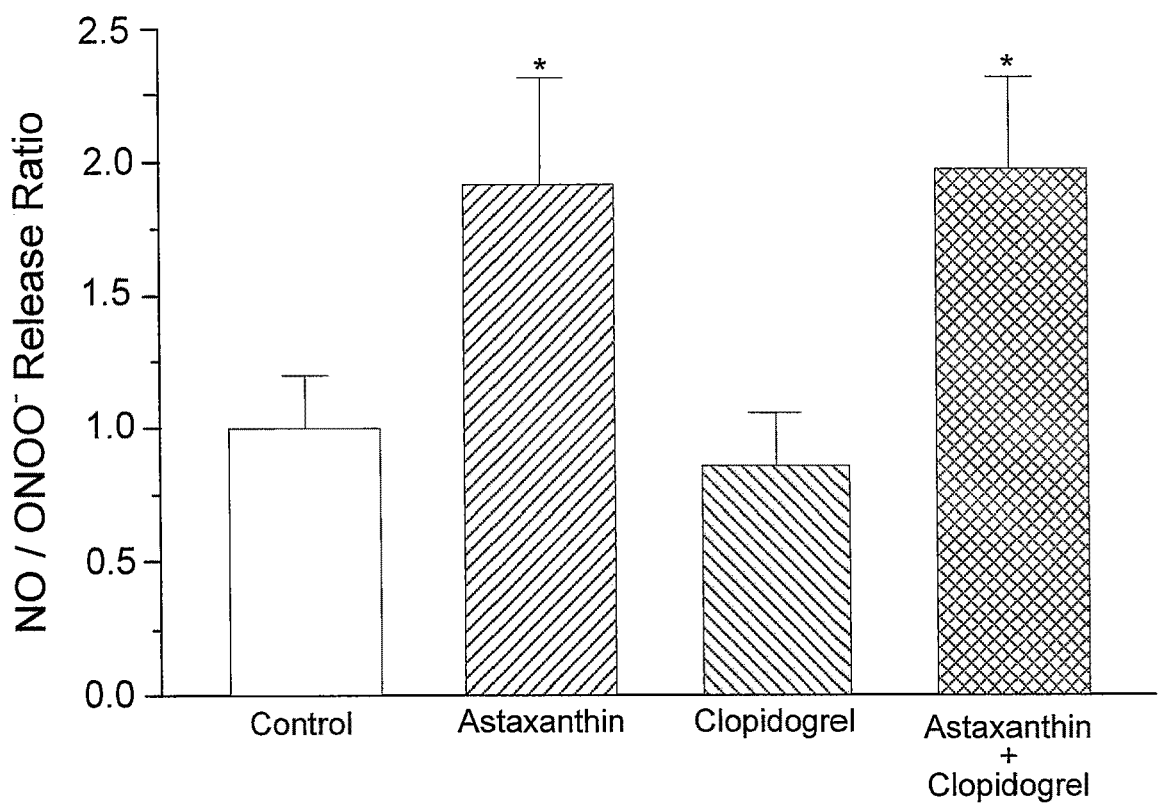
FIG. 7 shows the effects on calcium ionophore (CaI)-stimulated total nitric oxide and peroxynitrite release (expressed as a ratio) from human umbilical vein endothelial cells following incubation with homochiral astaxanthin and clopidogrel, either alone or in combination.

Shown in FIG. 7 are the effects on calcium ionophore (CaI)-stimulated total nitric oxide (NO) and peroxynitrite ($OONO^-$) release (expressed as a ratio) from human umbilical vein endothelial cells (HUVEC) following incubation with homochiral astaxanthin (3S,3'S-AST; 5.0 µM) and clopidogrel (1.0 µM), either alone or in combination. Statistically significant increases in the NO/$OONO^-$ release ratio were seen after treatment with homochiral astaxanthin (*$p<0.001$ versus controls and clopidogrel-treated cells). Treatment with clopidogrel alone did not significantly change the NO/$OONO^-$ release from HUVEC, and no additional significant increase in the release ratio was observed after combination with homochiral astaxanthin.

Example 6

Figure 11:
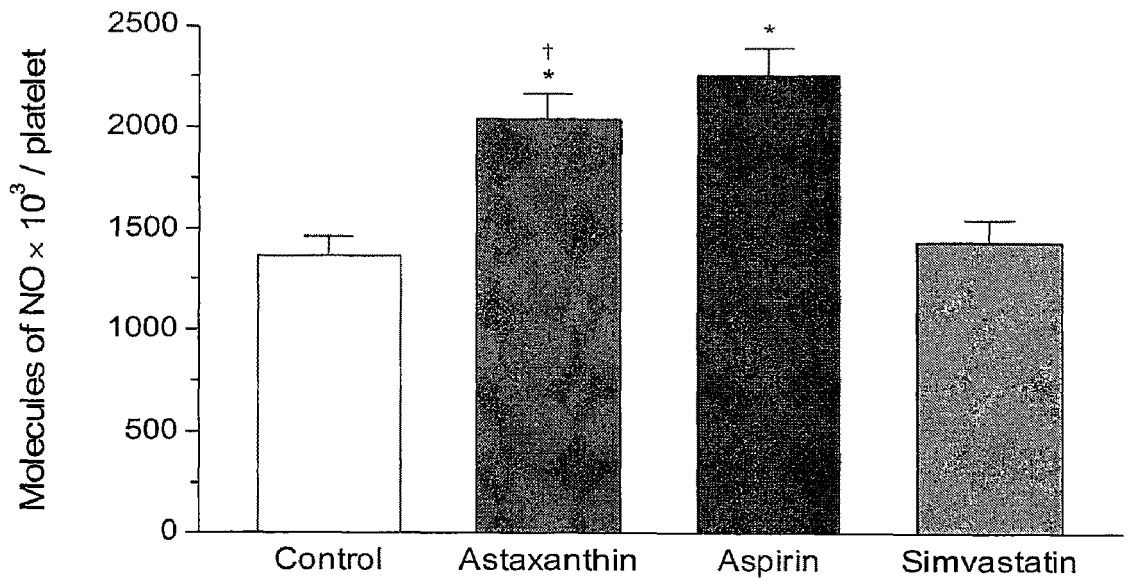
FIG. 11 shows the comparative effects of astaxanthin, aspirin and simvastatin (all at 1.0 µM) on platelet-derived nitric oxide release following stimulation with IP3 (1.0 µM)

Shown in FIG. 11 are the comparative effects of astaxanthin, aspirin and simvastatin (all at 1.0 µM) on platelet-derived nitric oxide release following stimulation with IP3 (1.0 µM). Values are reported as mean±S.D. (N=5). *$p<0.001$ versus control or simvastatin; †$p<0.01$ versus aspirin treatment (ANOVA Student-Newman-Keuls multiple comparisons test; overall ANOVA: $p<0.0001$; F=70.756).

Example 7

Figure 12:
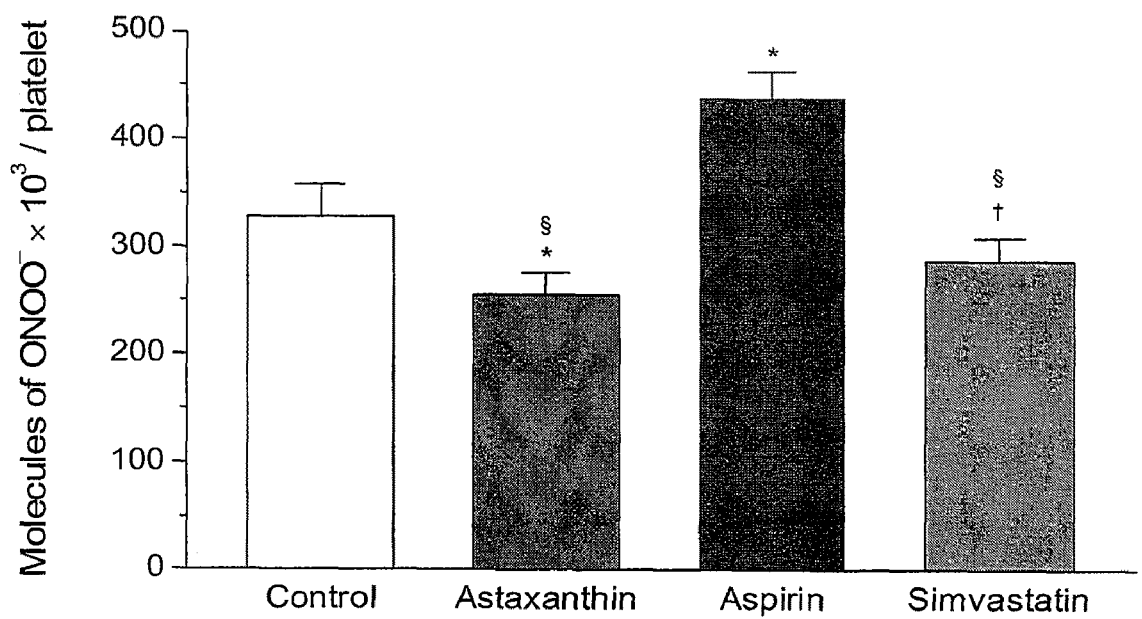
FIG. 12 shows the comparative effects of astaxanthin, aspirin and simvastatin (all at 1.0 µM) on platelet-derived peroxynitrite release following stimulation with IP3 (1.0 µM)

Shown in FIG. 12 are the comparative effects of astaxanthin, aspirin and simvastatin (all at 1.0 µM) on platelet-derived peroxynitrite release following stimulation with IP3 (1.0 μM). Values are reported as mean±S.D. (N=5). *p<0.001 and †p<0.05 versus control; §p<0.001 versus aspirin treatment (ANOVA Student-Newman-Keuls multiple comparisons test; overall ANOVA: p<0.0001; F=52.475).

Example 8

Figure 13:
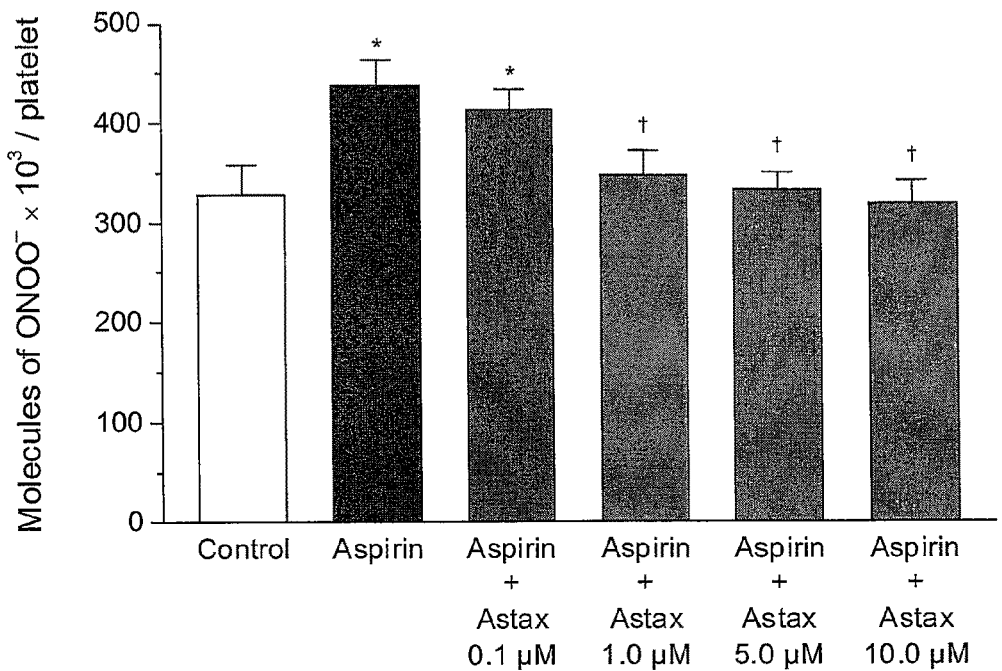
FIG. 13 shows the effects of aspirin (1.0 µM) on platelet peroxynitrite release in the absence and presence of increasing levels of astaxanthin following stimulation with IP3 (1.0 µM)

Shown in FIG. 13 are the effects of aspirin (1.0 μM) on platelet peroxynitrite release in the absence and presence of increasing levels of astaxanthin following stimulation with IP3 (1.0 μM). Values are reported as mean±S.D. (N=5). *p<0.001 versus control and †p<0.001 versus aspirin alone (ANOVA Student-Newman-Keuls multiple comparisons test; overall ANOVA: p<0.0001; F=21.905). Abbreviations: Astax=Astaxanthin.

Example 9

Figure 14:
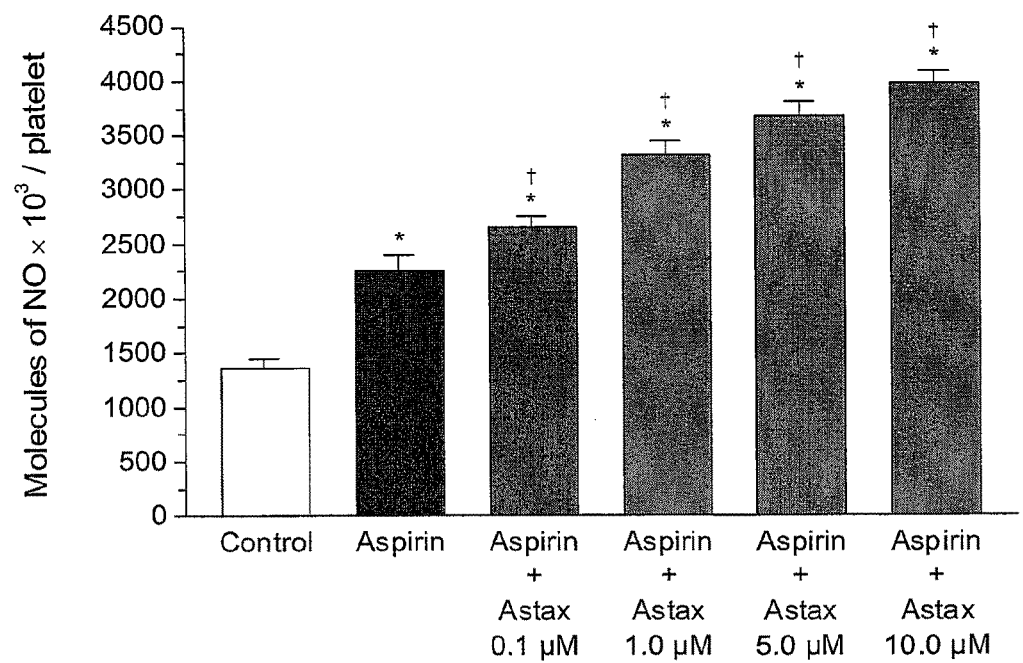
FIG. 14 shows the effects of aspirin (1.0 µM) on platelet nitric oxide release in the absence and presence of increasing levels of astaxanthin following stimulation with IP3 (1.0 µM)

Shown in FIG. 14 are the effects of aspirin (1.0 μM) on platelet nitric oxide release in the absence and presence of increasing levels of astaxanthin following stimulation with IP3 (1.0 μM). Values are reported as mean±S.D. (N=5). *p<0.001 versus control and †p<0.001 versus aspirin alone (ANOVA Student-Newman-Keuls multiple comparisons test; overall ANOVA: p<0.0001; F=358.23). Abbreviations: Astax=Astaxanthin.

Example 10

Figure 15:
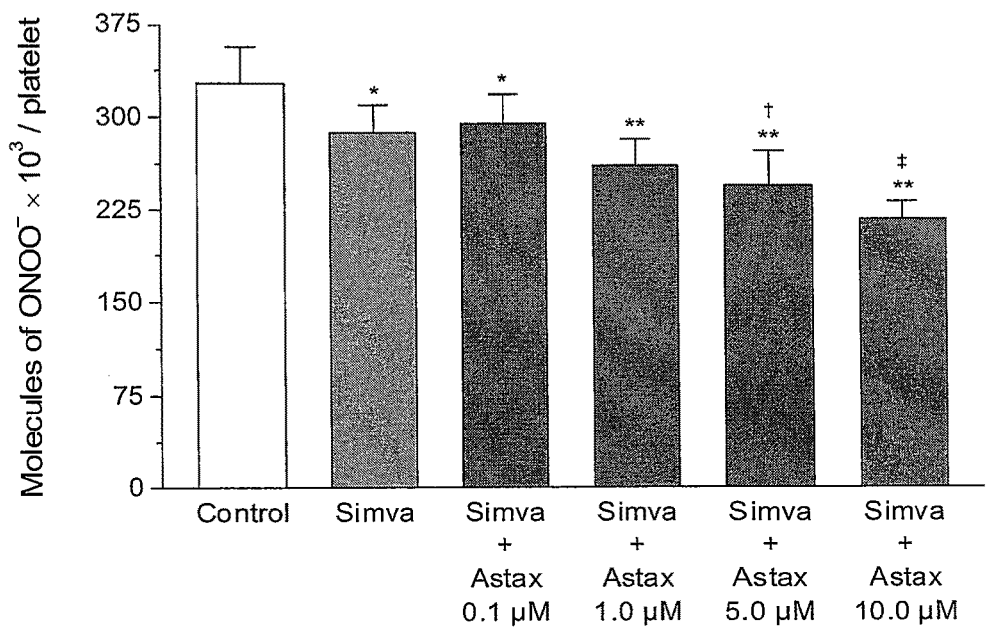
FIG. 15 shows the effects of simvastatin (1.0 µM) on platelet peroxynitrite release in the absence and presence of increasing levels of astaxanthin following stimulation with IP3 (1.0 µM)

Shown in FIG. 15 are the effects of simvastatin (1.0 μM) on platelet peroxynitrite release in the absence and presence of increasing levels of astaxanthin following stimulation with IP3 (1.0 μM). Values are reported as mean±S.D. (N=5). *p<0.05 and **p<0.001 versus control; †p<0.05 and ‡p<0.001 versus simvastatin alone (ANOVA Student-Newman-Keuls multiple comparisons test; overall ANOVA: p<0.0001; F=13.716). Abbreviations: Astax=Astaxanthin; Simva=Simvastatin.

Example 11

Figure 16:
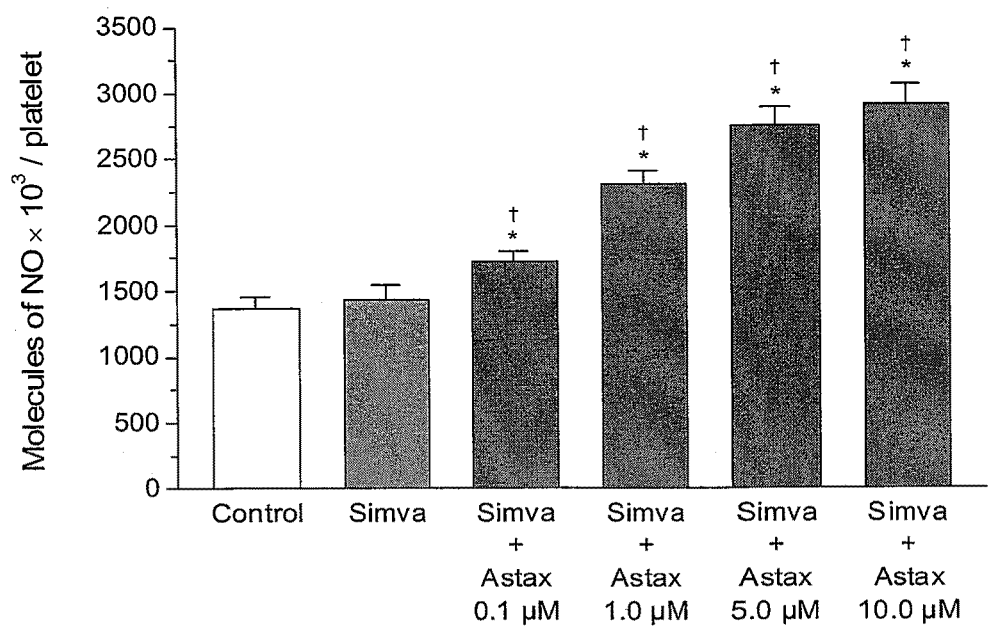
FIG. 16 shows the effects of simvastatin (1.0 µM) on platelet nitric oxide release in the absence and presence of increasing levels of astaxanthin following stimulation with IP3 (1.0 µM)

Shown in FIG. 16 are the effects of simvastatin (1.0 μM) on platelet nitric oxide release in the absence and presence of increasing levels of astaxanthin following stimulation with IP3 (1.0 μM). Values are reported as mean±S.D. (N=5). *p<0.001 versus control and †p<0.001 versus simvastatin alone (ANOVA Student-Newman-Keuls multiple comparisons test; overall ANOVA: p<0.0001; F=158.53). Abbreviations: Astax=Astaxanthin; Simva=Simvastatin.

Example 12

Figure 17:
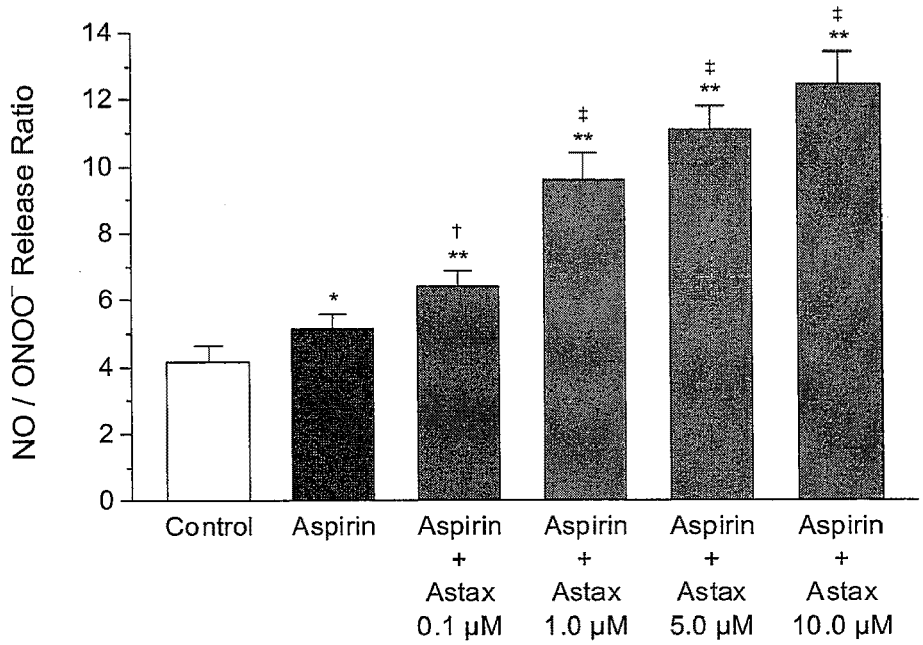
FIG. 17 shows the effects of aspirin (1.0 µM) on platelet nitric oxide/peroxynitrite release ratio in the absence and presence of increasing levels of astaxanthin following stimulation with IP3 (1.0 µM)

Shown in FIG. 17 are the effects of aspirin (1.0 μM) on platelet nitric oxide/peroxynitrite release ratio in the absence and presence of increasing levels of astaxanthin following stimulation with IP3 (1.0 μM). Values are reported as mean±S.D. (N=5). *p<0.05 and **p<0.001 versus control; †p<0.01 and ‡p<0.001 versus aspirin alone (ANOVA Student-Newman-Keuls multiple comparisons test; overall ANOVA: p<0.0001; F=129.98). Abbreviations: Astax=Astaxanthin.

Example 13

Figure 18:
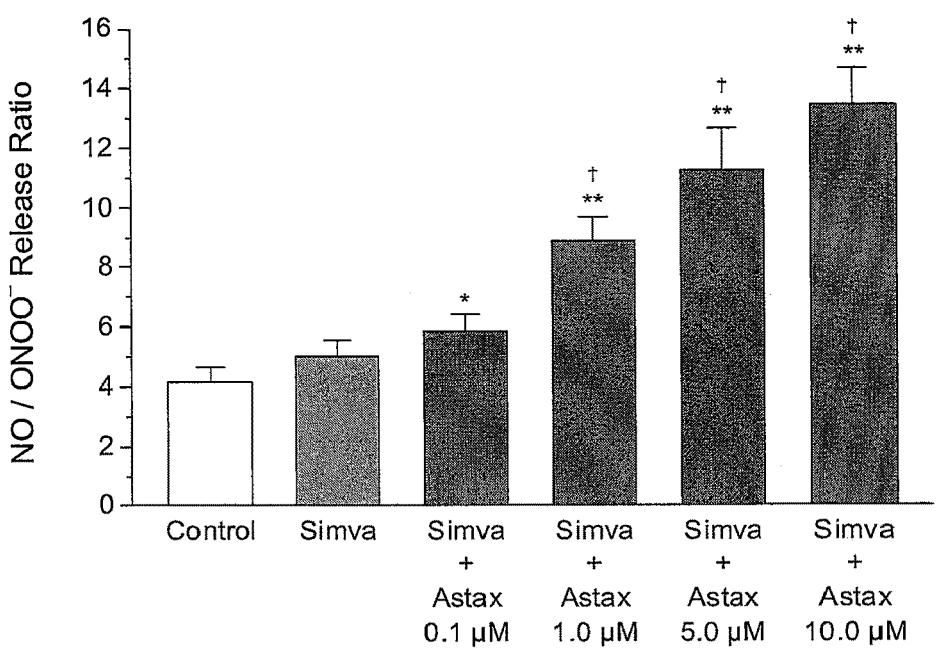
FIG. 18 shows the effects of simvastatin (1.0 µM) on platelet nitric oxide/peroxynitrite release ratio in the absence and presence of increasing levels of astaxanthin following stimulation with IP3 (1.0 µM)

Shown in FIG. 18 are the effects of simvastatin (1.0 μM) on platelet nitric oxide/peroxynitrite release ratio in the absence and presence of increasing levels of astaxanthin following stimulation with IP3 (1.0 μM). Values are reported as mean±S.D. (N=5). *p<0.05 and **p<0.001 versus control; †p<0.001 versus simvastatin alone (ANOVA Student-Newman-Keuls multiple comparisons test; overall ANOVA: p<0.0001; F=84.477). Abbreviations: Astax=Astaxanthin; Simva=Simvastatin.

Example 14

Figure 19:
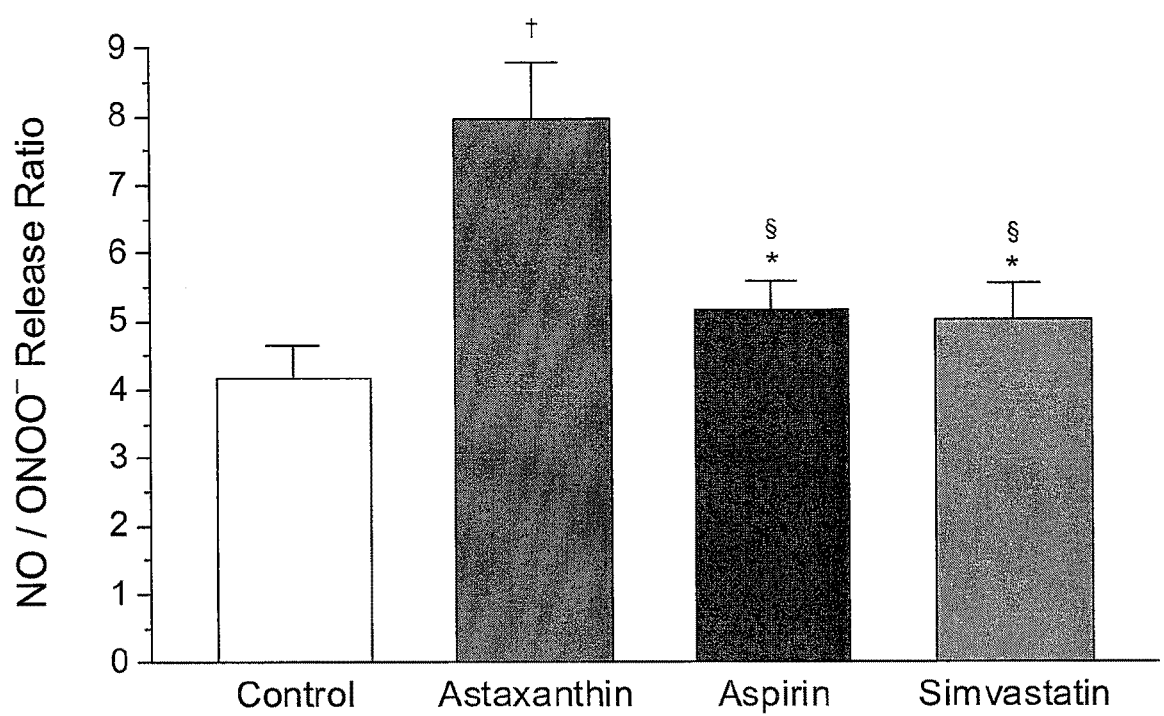
FIG. 19 shows the effects of astaxanthin, simvastatin, and aspirin on platelet nitric oxide/peroxynitrite release ratio following stimulation with IP3 (1.0 µM)

Shown in FIG. 19 are the comparative effects of astaxanthin, aspirin and simvastatin (all at 1.0 μM) on platelet-derived nitric oxide/peroxynitrite release ratio following stimulation with IP3 (1.0 μM). Values are reported as mean±S.D. (N=5). *p<0.05 and †p<0.001 versus control; §p<0.001 versus astaxanthin treatment (ANOVA Student-Newman-Keuls multiple comparisons test; overall ANOVA: p<0.0001; F=40.020).

Interpretation of Results

The beneficial cardiovascular effects of clopidogrel in vivo have been well documented, particularly as they relate to platelet inhibition through blockade of one of the two adenosine diphosphate (ADP) receptors. ADP is released from platelet dense granules upon platelet activation by numerous agonists, and subsequently amplifies platelet thrombotic response regardless of the inciting stimulus. The $P2Y_{12}$ receptor on which clopidogrel is active is linked to $G_i$; it plays a special role in the amplification of platelet activation initiated by numerous other pathways. Such activation can result in multiple responses that are critical to arterial thrombosis and the inflammatory responses associated with it: (1) platelet aggregation; (2) dense and alpha granule secretion; and (3) procoagulant activity. Current therapeutic regimens using clopidogrel can sometimes yield variable and incomplete $P2Y_{12}$ receptor blockade; more effective strategies to block $P2Y_{12}$ receptor activation, as well as combination therapies with aspirin to improve overall anti-platelet efficacy offer the potential of improved clinical efficacy. Additional strategies to improve the overall cardiovascular effects of this thienopyridine agent would include identification and exploitation of novel mechanisms of action on the vascular platelet for clopidogrel—as well as to identify novel combination therapies based on compounds with complementary, and perhaps synergistic, action(s) on platelet activation.

In the present application, the main effects of homochiral (3S,3'S)-astaxanthin and clopidogrel were tested on NO generation from isolated mammalian platelets using previously-described nanosensor technology. The absolute generation of NO after treatment with each agent was compared to baseline levels of NO generation in control (untreated) vascular platelets. Significant mean main effects on platelet NO generation were observed for both agents. When normalized to mean control levels in untreated platelets, clopidogrel at 1 μM increased the generation of NO by almost 50%—thereby identifying a secondary, and important, in vitro potential function of this cardiovascular agent on the platelet. The mechanism of action of clopidogrel on NO generation is not completely understood at the present time, although beneficial antioxidant and anti-inflammatory effects of this agent have been recently suggested. Although in vivo metabolic activation of clopidogrel is believed to be necessary for effective anti-aggregating properties, in the current study, we found activity of the parent compound on NO bioavailability that appears to be separate from the ADP-receptor binding function. This seminal report will require additional follow-up to document the mechanism of action described herein.

Similarly, homochiral astaxanthin at 5 µM increased the generation of NO by almost 100% when used as monotherapy, thereby documenting for the first time a favorable effect on nitric oxide bioavailability and a potential reduction in oxidative stress in vascular platelets for astaxanthin. Physiologic levels of astaxanthin in serum could likely be achieved with a 200 to 250 mg dose of this agent in appropriate lipophilic vehicle, if dose-proportionality is achieved upon stepped dosing of the non-esterified compound. Significantly higher doses of astaxanthin and its derivatives are well tolerated in animals after both I.V. and oral administration.

Astaxanthin may intersect the nitric oxide-peroxynitrite axis to platelets through modulation of superoxide anion bioavailability. Astaxanthin is a well-documented scavenger of biologically-produced superoxide. As well, soft drugs based on the astaxanthin scaffold are capable of potent superoxide anion scavenging, even in the aqueous phase. The additional anti-inflammatory effects of the parent compound, and its bioactive synthetic diesters, are the subject of recent reviews. Additional favorable anti-inflammatory effects of astaxanthin-based soft drugs cannot be ruled out in the setting of platelet activation; direct scavenging of peroxynitrite, as described for chemically similar C40 carotenoids (albeit not astaxanthin), is also possible. Lycopene is the only other C40 carotenoid with apparent activity on platelet aggregation, through mechanisms separate from the current mechanism identified in the current study.

Strikingly, the combination of homochiral astaxanthin (at 5 µM) with clopidogrel (at 1 µM) exhibited synergistic improvement on NO bioavailability in the combination-treated platelets. The combination resulted in a mean % increase in NO release (normalized to levels in control, untreated platelets) of approximately 4-fold. This was a significant, non-additive improvement over the favorable increases seen with each agent as monotherapy. The kinetics of NO release were altered by the combination, resulting in an increased length of NO production by the platelets (from 13 s with homochiral astaxanthin alone, to 34 s with the combination). The agents therefore appear to be operating on at least partially independent mechanisms of action which are complementary in nature. Further investigations of these complementary mechanism(s) of action—alone and in combination—are therefore suggested by this seminal work.

In conclusion, the studies presented herein demonstrate a potent and synergistic effect of carotenoids or carotenoid derivatives (e.g., astaxanthin) and clopidogrel on platelet-derived NO release. The novel platelet effects observed with this combination may offer additional protection against atherothrombotic events, already documented in humans for clopidogrel. As astaxanthin appears to be safe for human consumption at recommended doses in humans, additional studies of the anti-platelet effects of this agent in humans may be warranted.

In Vivo Model of Reocclusion Following Fibrinolytic Therapy:

Drug Preparation:

Disodium disuccinate astaxanthin (DDA; see FIG. 1B) was synthesized from commercially available crystalline astaxanthin (Buckton Scott, India) as previously described in Frey, et al. ("The efficient synthesis of disodium disuccinate astaxanthin (Cardax)." *Org Process Res Dev* 8: 796-801, 2004.). The final product purity was 97% (as area under the curve) by HPLC analysis. DDA was dissolved directly in sterile-filtered deionized water. The maximum aqueous dispersibility of DDA is approximately 10 mM, or 8.64 mg/ml. Vehicle consisted of isotonic sterile 0.9% NaCl solution.

Canine Thrombosis Model:

The experimental model used is a modification of that described by Hong, et al., (*Thromb Res* 117: 333-342, 2006), Rebello, et al., (*Arterioscler Thromb Vasc Biol* 18: 954-960, 1998), and Rote, et al. (*Cardiovasc Res* 27: 500-507, 1993). Healthy male or female purpose-bred beagle dogs (9-13 kg) were anesthetized with sodium pentobarbital (30 mg/kg, i.v.), intubated and ventilated with room air at a tidal volume of 30 ml/kg and a rate of 12 breaths per minute. The left carotid artery (LCA) was exposed by blunt dissection using care not to injure the vessel. An external adjustable stainless steel constrictor was shaped to fit each vessel and adjusted with a nylon screw (2 mm in diameter) to reduce the pulsatile flow pattern by 50% without altering the mean carotid artery blood flow rate. Vascular injury was accomplished with the application of a low anodal current to the intimal surface of the vessel via an intravascular electrode composed of a Teflon® insulated, silver-coated, copper wire. The intravascular electrode was connected to the positive pole (anode) of a dual-channel square wave generator (Grass S88 stimulator) and a Grass Constant Current Unit; model CCUIA (Grass Instrument Division, Astro-Med, Inc. West Warwick, R.I.). The cathode was attached at a remote subcutaneous site. The current (300 µA) applied to the intimal surface of the vessel was monitored continuously. The intravascular electrode and mechanical constrictor were upstream with respect to the flow probe. Blood flow in the carotid artery was quantified using a graded patency scoring system of 0-3 as described previously (16), in which a score of 0 represents no flow (total occlusion), 1-2 represents varying degrees of reduced and cyclic patterns of flow and 3 represents non-oscillatory or uninterrupted blood flow.

Experimental Design:

FIG. 8 illustrates the experimental protocol. Twenty-eight dogs were randomized between four treatment groups receiving either DDA (10, 30 or 50 mg/kg i.v. n=7 per group) or 0.9% NaCl (n=7). Experimental thrombosis of the left carotid artery (LCA) was induced to achieve total occlusion of blood flow. Thirty minutes later, the animals received an intravenous infusion of DDA or an equivalent volume of 0.9% NaCl solution for thirty minutes (flow rate depended on dose of DDA). The drug treatment was followed by intra-carotid administration of rtPA (0.54 µg/kg bolus+3.26 µg/kg/h infusion) delivered immediately proximal to the occlusive thrombus. The infusion of rtPA was discontinued 10 min after establishing 20% of the original flow. The end-point determinations consisted of: (1) time to thrombolysis, (2) incidence of LCA reocclusion (secondary thrombosis), (3) vessel patency scores assessed by dynamic flow recordings, and (4) thrombus weight.

Ex Vivo Platelet Aggregation:

Whole blood (10 ml) was drawn from a right femoral vein cannula into a plastic syringe containing 3.7% sodium citrate as the anticoagulant (1:100 volume ratio of citrate to blood). A whole blood cell count was determined with an H-2000 cell counter (Texas International Laboratories, Inc., Culver City, Calif.). Platelet-rich plasma (PRP), the supernatant present after centrifugation of whole blood at 100×g for 10 min, was diluted with Platelet-poor plasma (PPP) to achieve a platelet count of approximately 200,000/ml. PPP was prepared by centrifuging the remaining blood at 1,500×g for 10 min and discarding the bottom cellular layer. Ex vivo platelet aggregation was assessed by established spectrophotometric methods with the use of a four-channel aggregometer (BioData PAP-4; BioData Corp., Horsham, Pa.) by recording the increase in light transmission through a stirred suspension of PRP maintained at 37° C. Aggregation was induced with ADP (20 μM) or AA (0.65 mM). A subaggregatory concentration of epinephrine (550 nM) was used to prime the platelets before addition of the agonists to induce platelet aggregation. Values for platelet aggregation are expressed as percentage of light transmission standardized to PRP and PPP samples yielding 0 and 100% light transmission, respectively.

Bleeding Time Determinations:

Tongue bleeding time (BT) was determined with the use of a SurgiCut™ (International Technidyne Corp, Edison, N.J.) device that makes a uniform incision 5 mm long and 1 mm deep on the upper surface of the tongue. The tongue lesion was blotted with filter paper every 20 sec until the transfer of blood to the filter paper was no longer apparent. The interval, from the time of the tongue incision until the time that blood was no longer transferred to the filter paper, was recorded as the tongue bleeding time.

Statistical Analysis:

The data are expressed as mean±SEM and were analyzed by one-way analysis of variance for group comparisons followed by a Dunnett's post hoc t-test to determine the level of significance. The incidence of carotid artery reocclusion was compared between the groups by chi-square test. The change over time in the vessel blood flow patency score was compared between two groups by two-way analysis of variance followed by Bonferroni post-tests to determine the level of significance. Values are considered statistically different at $p < 0.05$.

Example 15

The hemodynamic variables of mean arterial blood pressure and heart rate did not differ significantly throughout the experimental protocol in any of the groups (Table 1). However, a small (<15%) transient decrease in arterial blood pressure was seen in 5 dogs receiving the highest dose of DDA (50 mg/kg). The blood pressure returned to original values within 30 min and did not affect the outcome of the study (data not shown).

TABLE 1

Thrombotic effects of the combined administration of DDA and rt-PA.

| | Platelet Count (Baseline) | Platelet Count (Post rt-PA) | Time to occlusion (min) | Time to thrombolysis (min) | Incidence of Reocclusion |
|---|---|---|---|---|---|
| 0 mg/kg DDA (0.9% NaCl) | 364 ± 38 | 338 ± 36 | 86.1 ± 6.7 | 16.4 ± 5.5 | 5/7 |
| 10 mg/kg DDA | 392 ± 36 | 352 ± 37 | 84.3 ± 10.2 | 20.3 ± 6.7 | 6/7 |
| 30 mg/kg DDA | 349 ± 36 | 316 ± 32 | 74.9 ± 14.2 | 20.6 ± 7.9 | 3/7 |
| 50 mg/kg DDA | 431 ± 31 | 363 ± 66 | 95.6 ± 19.8 | 24.0 ± 6.0 | 1/7* |

Example 16

Incidence of Left Carotid Artery Reocclusion

The LCA was subjected to electrolytic injury leading to the development of an occlusive thrombus as indicated by the cessation of blood flow in the injured vessel. Thirty minutes later, either DDA (10, 30 or 50 mg/kg) or 0.9% NaCl solution was administered followed by the intra-carotid infusion of rt-PA that was delivered immediately proximal to the obstructive thrombus. The time to clot lysis was similar between the DDA and 0.9% NaCl-treated animals (Table 1). However, the incidence of reocclusion of the LCA after successful thrombolysis was dose dependently reduced by DDA (6/7, 3/7, 1/7 for 10, 30 and 50 mg/kg doses, respectively) compared to the 0.9% NaCl-treated group (5/7)(Table 1).

Example 17

Vessel Patency Score

Successful thrombolysis of the LCA was achieved with the local administration of rt-PA in both the 0.9% NaCl and DDA treated animals. In the absence of an adjunctive anticoagulant, however, most recanalized vessels exhibit poor quality of blood flow and progress toward reocclusion. Table 2 summarizes the patency scores of the left carotid arteries assessed at 30-min intervals after the administration of rt-PA. In animals receiving the intermediate and highest doses of DDA (30 and 50 mg/kg), there was a progressive improvement in the vessel patency score during the protocol. The benefit of DDA was more apparent when compared to the 0.9% NaCl-treated group. Although the time to thrombolysis in the LCA was not significantly different between the groups, the vessel patency scores of and the incidence of reocclusion were improved significantly in the DDA-treated animals.

TABLE 2

Effect of DDA on arterial patency score, a determinant of the quality of blood flow.

| Time period (min) | 0-30 | 30-60 | 60-90 | 90-120 | 120-150 | 150-180 |
|---|---|---|---|---|---|---|
| 0 mg/kg DDA (0.9% NaCl) | 1.3 ± 0.2 | 1.7 ± 0.3 | 1.0 ± 0.4 | 0.7 ± 0.5 | 0.7 ± 0.5 | 0.9 ± 0.6 |
| 10 mg/kg DDA | 1.4 ± 0.2 | 1.3 ± 0.4 | 1.1 ± 0.3 | 1.1 ± 0.4 | 0.4 ± 0.4 | 0.4 ± 0.4 |
| 30 mg/kg DDA | 1.3 ± 0.2 | 1.3 ± 0.4 | 1.0 ± 0.4 | 1.6 ± 0.5 | 1.1 ± 0.5 | 1.4 ± 0.5 |
| 50 mg/kg DDA | 1.9 ± 0.3 | 2.4 ± 0.3 | 2.3 ± 0.4 | 2.3 ± 0.5* | 2.3 ± 0.4* | 2.3 ± 0.5* |

Example 18

Effects of DDA on Ex Vivo Platelet Aggregation

As illustrated in Table 1, whole blood platelet counts were unaffected by the administration of any dose of DDA. Ex vivo platelet aggregation responses to AA and ADP, however, were dose dependently attenuated by administration of DDA. Significant reductions in platelet aggregation were observed at 30 and 50 mg/kg doses. FIG. 8 shows the percent platelet aggregation responses to ADP (A) and AA (B) before and after occlusive thrombus formation in the LCA and subsequent treatment with DDA (10, 30 or 50 mg/kg) or 0.9% NaCl solution (0 mg/kg DDA) followed immediately by rt-PA. The data represent the mean of 7 experiments±SEM. (*) Indicates $p<0.05$ when compared with respective baseline values within each group by one-way ANOVA followed by Dunnets' post test. (†) Indicates $p<0.05$ when the same time point values are compared between DDA and 0.9% NaCl (0 mg/kg DDA) treatment by unpaired t-test. Baseline (pretreatment), black bars; Post drug treatment, white bars.

Example 19

Effect of DDA on Thrombus Weight

Figure 9:
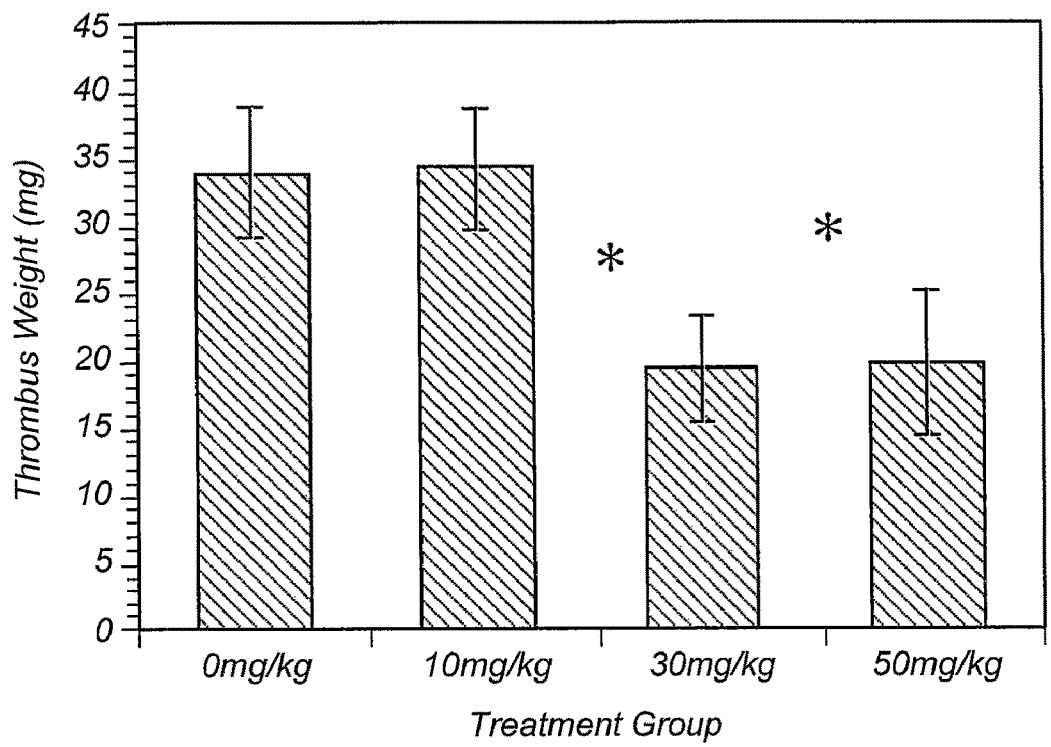
FIG. 9 shows thrombus weights after occlusive thrombus formation in the LCA and subsequent treatment with DDA (10, 30 or 50 mg/kg) or 0.9% NaCl solution followed immediately by rt-PA.

Intravenous administration of DDA dose dependently reduced thrombus weight measured at the end of the experimental protocol. DDA treatment resulted in a 43±4% and 42±5% (30 and 50 mg/kg doses, respectively) reduction in thrombus weights compared to those dogs treated with 0.9% NaCl solution. Turning to FIG. 9, thrombus weights after occlusive thrombus formation in the LCA and subsequent treatment with DDA (10, 30 or 50 mg/kg) or 0.9% NaCl solution followed immediately by rt-PA are shown. The data represent the mean of 7 experiments±SEM. * indicates $p<0.05$ when compared with 0.9% NaCl solution (0 mg/kg DDA, control) by unpaired t-test.

Example 20

Effects of DDA on Bleeding Time

Figure 10:
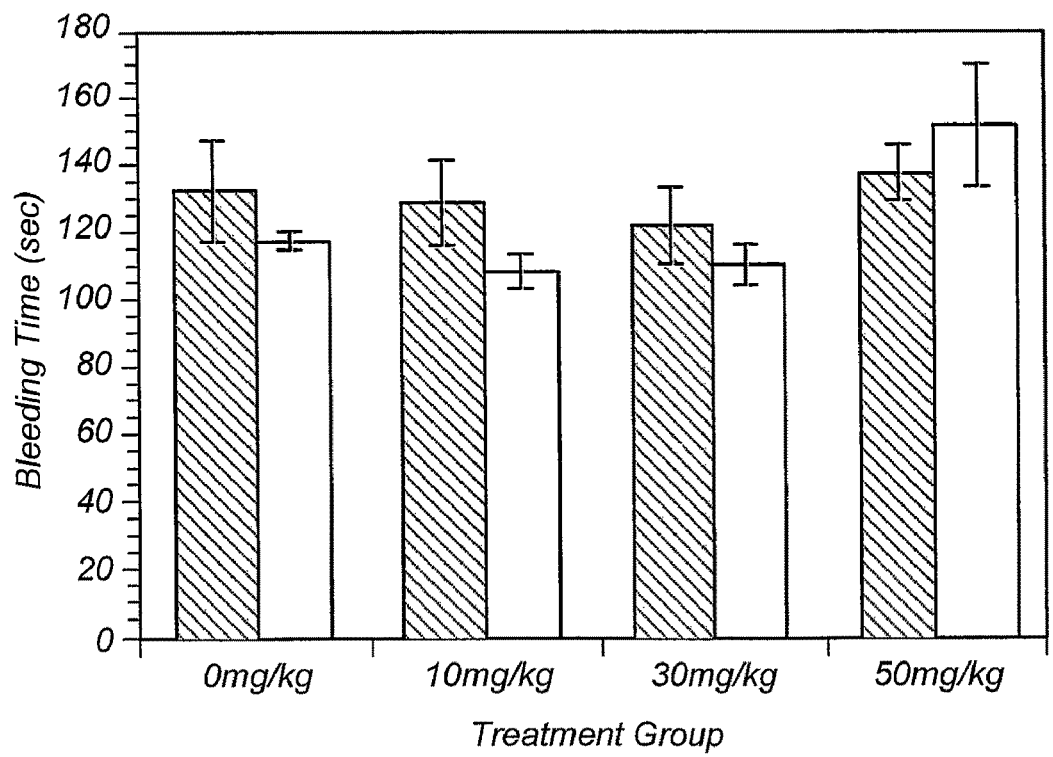
FIG. 10 shows the tongue bleeding time (sec) before and after occlusive thrombus formation in the LCA and subsequent treatment with DDA (10, 30 or 50 mg/kg) or 0.9% NaCl solution (0 mg/kg DDA) followed immediately by rt-PA.

Tongue template bleeding time was assessed using a SurgiCut™ device. Bleeding times were similar at baseline and after drug treatment in all of the treatment groups. Additionally there were no differences in bleeding times observed between groups at baseline of after drug treatment. FIG. 10 shows the Tongue bleeding time (sec) before and after occlusive thrombus formation in the LCA and subsequent treatment with DDA (10, 30 or 50 mg/kg) or 0.9% NaCl solution (0 mg/kg DDA) followed immediately by rt-PA. The data represent the mean of 7 experiments±SEM. Baseline (pretreatment), black bars; Post DDA treatment, white bars.

As shown in FIG. 11, treatment of platelets with astaxanthin or aspirin alone (1.0 µM) caused a pronounced increase in the capacity of platelets to generate NO by more than 30%. The rapid and potent effects of astaxanthin indicate a favorable effect on NOS coupling efficiency. The mechanism for enhanced NOS activity with astaxanthin may be through preservation of NOS and its co-factors in a non-oxidized and fully functional state.

Enhanced oxidative stress mechanisms cause the NOS enzymes to produce superoxide, the precursor of peroxynitrite (ONOO—). With NOS uncoupling, the enzyme acts like peroxynitrite synthase, a stimulant of NF-kB activity. Peroxynitrite is also known to oxidize NOS co-factors such as BH4 that leads to further NOS uncoupling. The combination of NOS uncoupling and co-factor depletion will ultimately lead to a disruption in the NO/ONOO— cycle, thus contributing to the pathogenesis of chronic diseases. Agents that block or reverse NOS uncoupling processes would have a potential role in the treatment of chronic diseases.

In contrast to astaxanthin and aspirin, simvastatin had no effect on platelet-derived NO release. The absence of activity with simvastatin may be due to the limited incubation period or a lack of an effect on platelet NOS expression. With a longer exposure, simvastatin may be able to influence genomic expression or stability of NOS RNA transcripts.

In FIG. 12, we observed that astaxanthin and simvastatin decreased ONOO— release while aspirin actually increased nitroxidative stress in a highly significant fashion. The beneficial effect of astaxanthin is support for its potent and rapid scavenging activity that maintains NOS function. Remarkably, astaxanthin was able to reverse the effect of aspirin on ONOO— release in a dose-dependent manner (FIG. 13). The effect of simvastatin was unexpected but may indicate an antioxidant effect associated with its chemical composition, including conjugated ring structures that may stabilize the unpaired electrons in various resonance structures.

In the combination study, astaxanthin potentiated (by 80%) the effect of NO release observed by aspirin alone (1.0 µM) and a 3-fold increase over untreated samples (FIG. 14). Astaxanthin also increased NOS coupling efficiency (ratio of NO/ONOO—) by approximately three-fold over control levels as well as aspirin alone (FIG. 16). In fact, aspirin separately failed to produce a favorable effect on NO/ONOO— ratio. The favorable effect of astaxanthin on NO release with aspirin was dose-dependent and attributed, in part, to its ability to attenuate or reverse aspirin-induced nitroxidative stress. Astaxanthin also enhanced the effect of simvastatin on platelet-derived NO release in a dose-dependent fashion. The separate effects of these compounds on the NO/ONOO— ratio are reviewed in FIG. 17 and highlight the benefits of astaxanthin.

Astaxanthin enhanced platelet-derived NO release while reducing nitroxidative stress by maintaining NOS in a functional state. The effect of astaxanthin was potentiated in the presence of aspirin which separately had adverse effects on nitroxidative stress. These findings indicate a new approach to reducing atherothrombotic risk with astaxanthin in a manner that complements other anti-platelet therapy, such as aspirin.

Metabolism of Carotenoid Derivatives

Pharmacokinetic data showing that the carotenoids derivatives described herein, when administered to animals, results in the accumulation of the parent carotenoid in the plasma has been determined. For example, we have determined that when astaxanthin derivatives are introduced into animals, the astaxanthin derivates are metabolized to produce free astaxanthin in the blood stream of the animal.

Example 21

Figure 21:
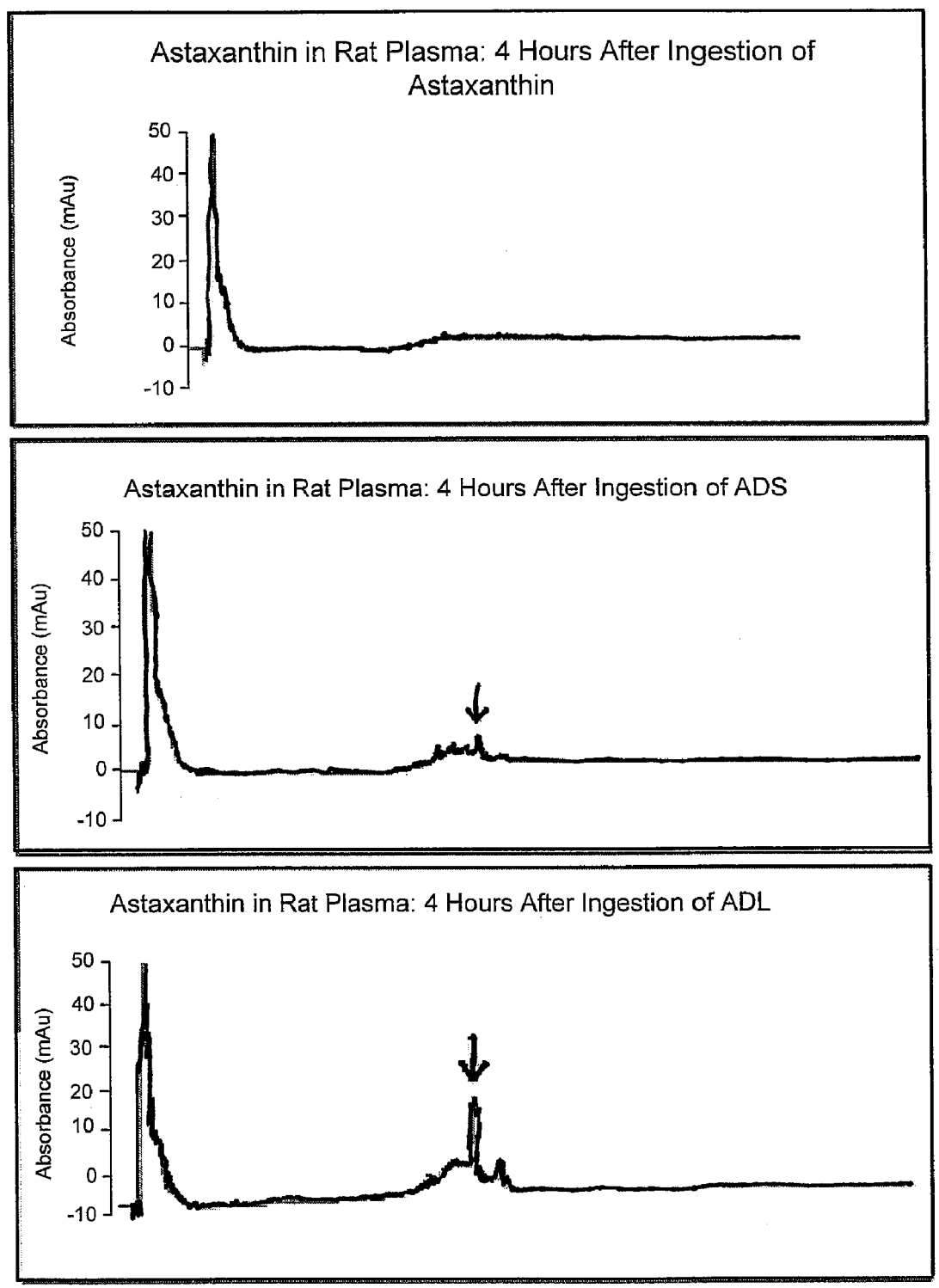
FIG. 21 shows chromatograms of rat plasma 4 and 8 hours after the administration of carotenoid derivatives.
Figure 21:
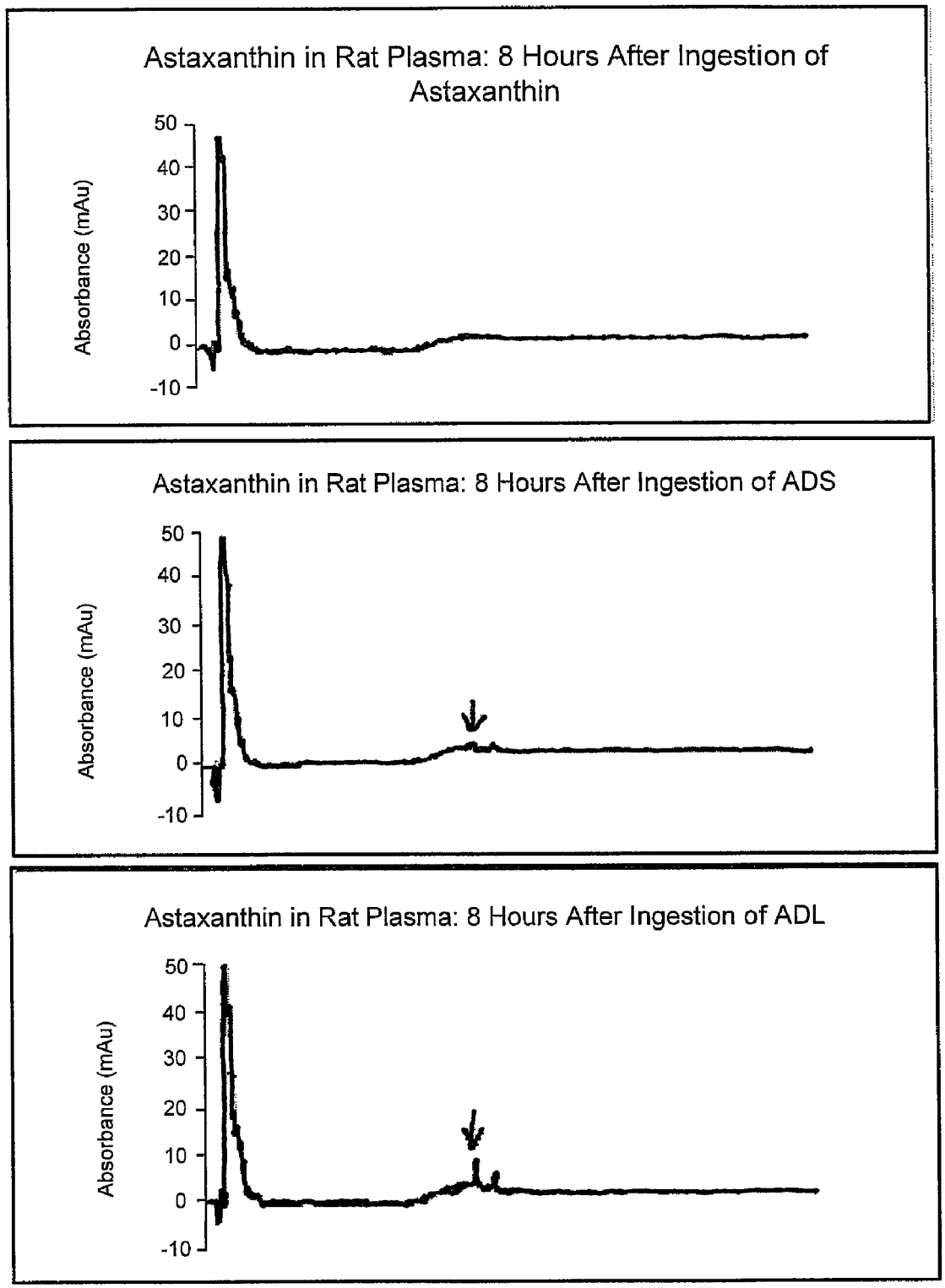

In one experiment, astaxanthin; all-trans 3S,3'S-astaxanthin diester disuccinate disodium salt (hereinafter "ADS"); and all-trans 3S,3'S-astaxanthin diester dilysinate tetrahydrochloride salt (hereinafter "ADL") were administered orally to separate rats as a lipid suspension. A single dose that included 500 mg/kg of the carotenoid/carotenoid derivative was administered to each rat. (See FIG. 20, PK Study #CXPK07201). Plasma from each of the rats was collected 4 hours after ingestion and 8 hours after ingestion and all samples were analyzed by high performance liquid chromatography ("HPLC"). HPLC analysis was used to detect the presence of free underivatized carotenoid (e.g., in this example, astaxanthin) in the plasma. HPLC chromatograms were collected for each plasma sample taken. The HPLC chromatograms are presented in FIG. 21. As can be seen in the chromatograms, four hours after ingestion of astaxanthin, there was no significant amount of free astaxanthin in the rat plasma collected. Eight hour after ingestion of astaxanthin, there was no significant amount of free astaxanthin in the rat plasma collected. This indicates that very little (if any) astaxanthin is absorbed by the rats through oral dosage. Four hours after ingestion of ADS and ADL shows a significant amount of free astaxanthin in the rat plasma collected. Eight hour after ingestion of ADS and ADL also shows a significant amount of free astaxanthin in the rat plasma collected. This indicates that carotenoid derivatives are absorbed and metabolized by the rats to produce underivatized carotenoid.

Example 22

In a another experiment, all-trans 3S,3'S-astaxanthin diester diglycinate dihydrochloride salt (hereinafter "ADG"); all-trans 3S,3'S-astaxanthin diester disarcosinate dihydrochloride salt (hereinafter "ADSa"); and ADL were administered orally to separate rats as a aqueous suspension containing 0.5% carboxymethylcellulose. A single dose that included 40 mg/kg of the carotenoid derivative was administered to each rat. (See FIG. 20, PK Study #CXPK07202). For each carotenoid derivative given to the rats in this example, the amount of all astaxanthin isomers, the amount of trans astaxanthin isomers, and the amount of cis astaxanthin isomers in the plasma was determined at predefined time intervals for 3 days (72 hours). Cmax (the peak plasma concentration of astaxanthin, trans astaxanthin and cis astaxanthin); Tmax (the time it took for the plasma concentration to reach Cmax); AUC (the area under the concentration curve); and $T_{1/2}$ (elimination half life) was determined for each sample and is presented in FIG. 22. As shown in FIG. 22, oral dosages of ADG, ADSa, and ADL were absorbed by the rats and metabolized to produce various Cmax concentrations of astaxanthin. This indicates that carotenoid derivatives ADG, ADSa, and ADL are absorbed and metabolized by the rats to produce underivatized carotenoid (in this example, astaxanthin).

Example 23

In another experiment, ADG; ADSa; and ADL were administered to separate rats intravenously as an aqueous solution. A single dose that included 5 mg/kg of the carotenoid derivative was administered to each rat. (See FIG. 20, PK Study #CXPK07202). For each carotenoid derivative given to the rats in this example, the amount of all astaxanthin isomers, the amount of trans astaxanthin isomers, and the amount of cis astaxanthin isomers in the plasma was determined at predefined time intervals for 3 days (72 hours). Cmax; Tmax; AUC; and T½ was determined for each sample and is presented in FIG. 22. As shown in FIG. 22, intravenous dosages of ADG, ADSa, and ADL were absorbed by the rats and metabolized to produce various Cmax concentrations of astaxanthin. This indicates that carotenoid derivatives ADG, ADSa, and ADL are absorbed and metabolized by the rats to produce underivatized carotenoid (in this example, astaxanthin).

Example 24

In another experiment, ADL was administered to non-naïve beagle dogs orally (as an aqueous suspension containing 0.5% carboxymethylcellulose) and intravenously as an aqueous solution. Oral doses that included 10 mg/kg of the carotenoid derivative, 100 mg/kg of the carotenoid derivative, and 500 mg/kg of the carotenoid derivative were administered to each dog. The intravenous dosage was 5 mg/kg. (See FIG. 20, PK Study #CXPK07402). For each carotenoid derivative given to the dogs in this example, the amount of all astaxanthin isomers, the amount of trans astaxanthin isomers, and the amount of cis astaxanthin isomers in the plasma was determined at predefined time intervals for 3 days (72 hours). Cmax; Tmax; AUC; and $T_{1/2}$ was determined for each sample and is presented in FIG. 23. As shown in FIG. 23, intravenous and oral dosages of ADL were absorbed by the dogs and metabolized to produce various Cmax concentrations of astaxanthin. This indicates that carotenoid derivatives ADL are absorbed and metabolized by the dogs to produce underivatized carotenoid (in this example, astaxanthin).

Example 25

In another experiment, ADL was administered to naïve beagle dogs orally (as an aqueous suspension containing 0.5% carboxymethylcellulose) twice a day for six days. Each oral dose included 75 mg/kg of the carotenoid derivative. (See FIG. 20, PK Study #CXPK07404). For each carotenoid derivative given to the dogs in this example, the amount of all astaxanthin isomers, the amount of trans astaxanthin isomers, and the amount of cis astaxanthin isomers in the plasma was determined at predefined time intervals for 6 days. Cmax; Tmax; AUC; and $T_{1/2}$ was determined for each sample and is presented in FIG. 24. As shown in FIG. 24, oral dosages of ADL were absorbed by the dogs and metabolized to produce various Cmax concentrations of astaxanthin over the six-day period. This indicates that carotenoid derivatives ADL are absorbed and metabolized by the dogs to produce underivatized carotenoid (in this example, astaxanthin).

Example 26

Figure 25:
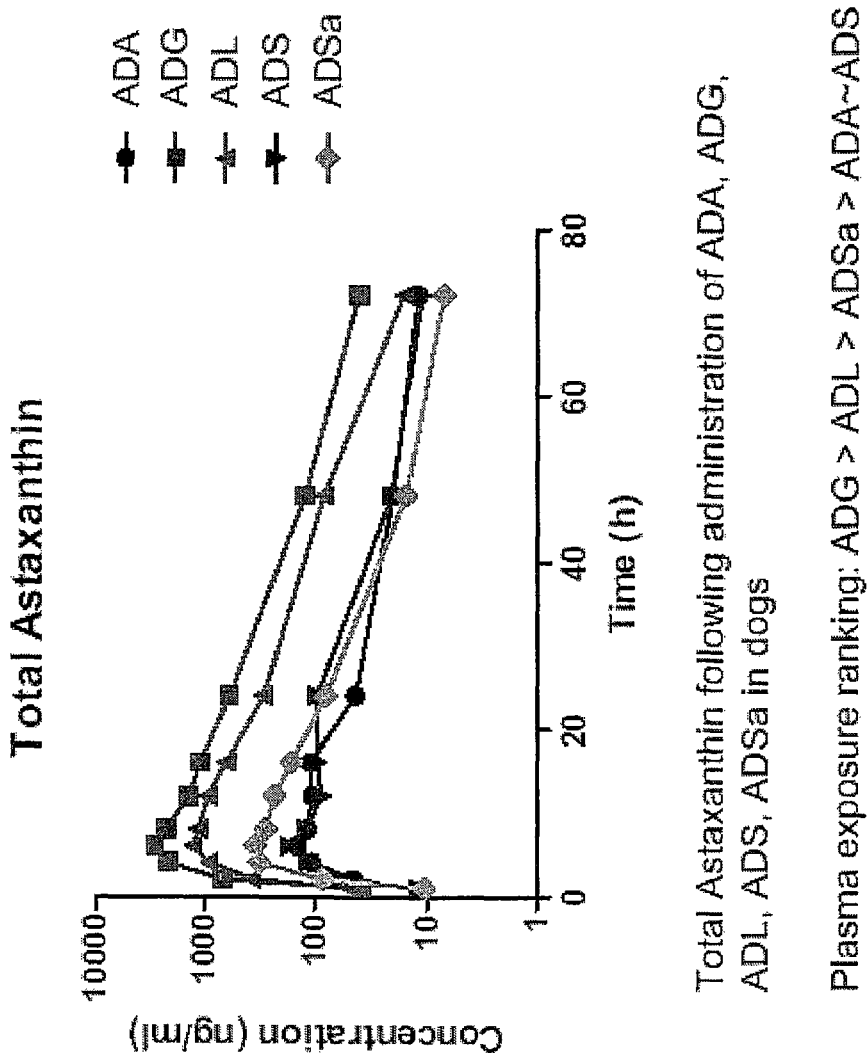
FIG. 25 shows a graph of the blood plasma concentration of carotenoid determined after the administration of carotenoid derivatives to dogs.

In another experiment, all-trans 3S,3' S-astaxanthin diester di-beta-alanine dihydrochloride salt (hereinafter "ADA"); ADG; ADL; ADSa; and ADS were administered orally to separate non-naïve dogs as a aqueous suspension containing 0.5% carboxymethylcellulose. A single dose that included 20 mg/kg of the carotenoid derivative was administered to each dog. (See FIG. 20, PK Study #CXPK07405). For each carotenoid derivative given to the dogs in this example, the amount of all astaxanthin isomers was determined at predefined time intervals for 3 days (72 hours). Cmax was determined for each sample and a graph representing the obtained data is presented in FIG. 25. As shown in FIG. 25, oral dosages of ADA, ADG, ADL, ADSa, and ADS were absorbed by the dogs and metabolized to produce various Cmax concentrations of astaxanthin. This indicates that carotenoid derivatives ADA, ADG, ADL, ADSa, and ADS are absorbed and metabolized by the dogs to produce underivatized carotenoid (in this example, astaxanthin).

Example 27

In another experiment, ADG or ADSa was administered to non-naïve beagle dogs orally (as an aqueous suspension containing 0.5% carboxymethylcellulose). Oral doses included either 50 mg/kg of the carotenoid derivative or 100 mg/kg of the carotenoid derivative. (See FIG. 20, PK Study #CXPK07406). For each carotenoid derivative given to the dogs in this example, the amount of all astaxanthin isomers, the amount of trans astaxanthin isomers, and the amount of cis astaxanthin isomers in the plasma was determined at predefined time intervals for 3 days (72 hours). Cmax; Tmax; AUC; and $T_{1/2}$ was determined for each sample and is presented in FIG. 26. As shown in FIG. 26, oral dosages of ADG or ADSa were absorbed by the dogs and metabolized to produce various Cmax concentrations of astaxanthin. This indicates that carotenoid derivatives ADL are absorbed and metabolized by the dogs to produce underivatized carotenoid (in this example, astaxanthin).

Example 28

In another experiment, ADSa was administered to non-naïve beagle monkeys orally (as an aqueous suspension containing 0.5% carboxymethylcellulose) and intravenously as an aqueous solution. Oral doses that included 10 mg/kg of the carotenoid derivative, 300 mg/kg of the carotenoid derivative, and 500 mg/kg of the carotenoid derivative were administered to each monkey. The intravenous dosage was 5 mg/kg. (See FIG. 20, PK Study #CXPK07502). For each carotenoid derivative given to the monkeys in this example, the amount of all astaxanthin isomers, the amount of trans astaxanthin isomers, and the amount of cis astaxanthin isomers in the plasma was determined at predefined time intervals for 3 days (72 hours). Cmax; Tmax; AUC; and $T_{1/2}$ was determined for each sample and is presented in FIG. 27. As shown in FIG. 27, intravenous and oral dosages of ADSa were absorbed by the monkeys and metabolized to produce various Cmax concentrations of astaxanthin. This indicates that carotenoid derivatives ADL are absorbed and metabolized by the monkeys to produce underivatized carotenoid (in this example, astaxanthin).

We have shown through these, and other unreported experiments, that carotenoid ester derivatives are readily metabolized by a variety of animals. Metabolism of carotenoid derivatives produces biologically significant amounts of the parent carotenoid in the blood stream of the animal.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes may be made in the elements described herein without departing from the spirit and scope of the invention as described in the following claims. In addition, it is to be understood that features described herein independently may, in certain embodiments, be combined.

What is claimed is:

1. A method of treating a disorder associated with platelet aggregation in a subject comprising administering to a subject who would benefit from such treatment a pharmaceutically acceptable composition comprising a therapeutically effective amount of a carotenoid analog or derivative wherein the carotenoid analog or derivative has the structure

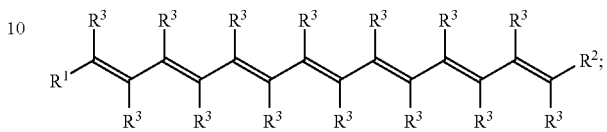

where each $R^3$ is independently hydrogen or methyl, and where $R^1$ and $R^2$ are each independently:

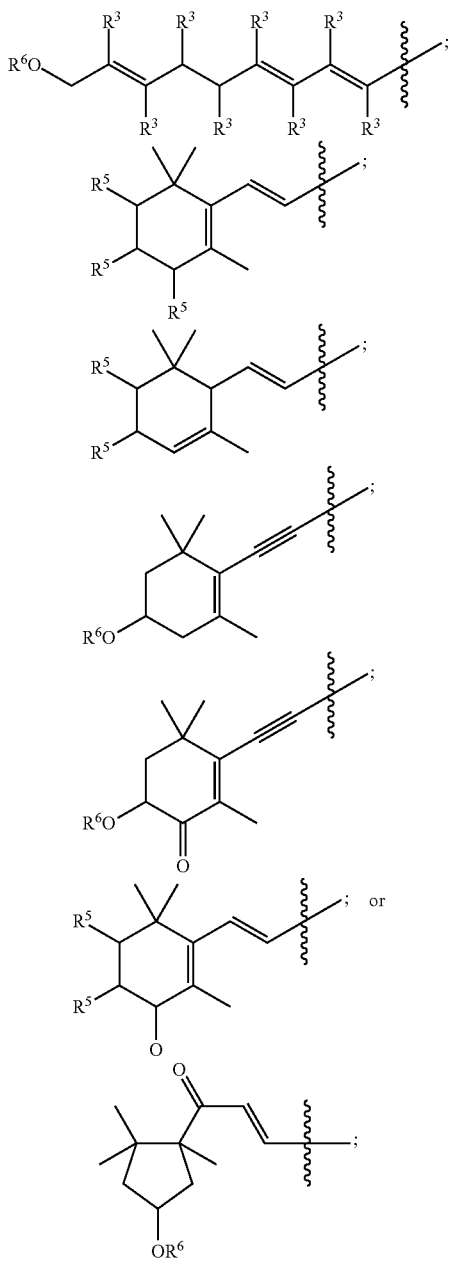

101

-continued

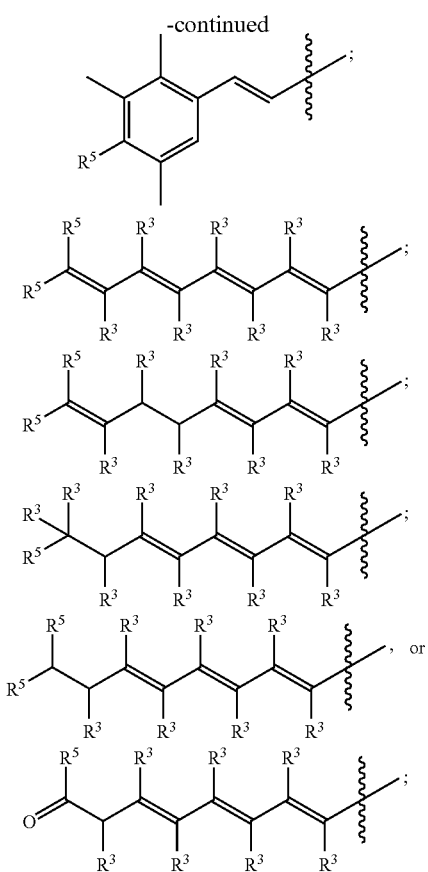

where each R⁵ is independently hydrogen, —CH₃, —OH, —CH₂OH or —OR⁶ wherein at least one R⁵ group in the carotenoid analog or derivative is —OR⁶; wherein each R⁶ is independently: H; alkyl; aryl; -alkyl-N(R⁷)₂; -aryl-N(R⁷)₂; -alkyl-N⁺(R⁷)₃; -aryl-N⁺(R⁷)₃; -alkyl-CO₂R⁹; -aryl-CO₂R⁹; -alkyl-CO₂⁻; -aryl-CO₂⁻; —C(O)-alkyl-N(R⁷)₂; —C(O)-aryl-N(R⁷)₂; —C(O)-alkyl-N⁺(R⁷)₃; —C(O)-aryl-N⁺(R⁷)₃; —C(O)-alkyl-CO₂R⁹; —C(O)-aryl-CO₂R⁹; -C(O)-alkyl-CO₂⁻; —C(O)-aryl-CO₂⁻; —C(O)—(NR⁷)-alkyl-N(R⁷)₂; —C(O)—(NR⁷)-aryl-N(R⁷)₂; —C(O)—(NR⁷)-alkyl-N⁺(R⁷)₃; —C(O)—(NR⁷)-aryl-N⁺(R⁷)₃; —C(O)—(NR⁷)-alkyl-CO₂R⁹; —C(O)—(NR⁷)-aryl-CO₂R⁹; —C(O)—(NR⁷)-alkyl-CO₂⁻; —C(O)—(NR⁷)-aryl-CO₂⁻; —C(O)—(NR⁷)-alkyl-N(R⁷)-alkyl-N(R⁷)₂; —C(O)—OR⁸; —P(O)(OR⁸)₂; —S(O)(OR⁸)₂; —C(O)—[C₆-C₂₄ saturated hydrocarbon]; —C(O)—[C₆-C₂₄ monounsaturated hydrocarbon]; —C(O)—[C₆-C₂₄ polyunsaturated hydrocarbon]; a peptide; a carbohydrate; a nucleoside reside; or a co-antioxidant; where R⁷ is hydrogen, alkyl, or aryl; where R⁸ is hydrogen, alkyl, aryl, benzyl or a co-antioxidant; and where R⁹ is hydrogen, alkyl, aryl, —P(O)(OR⁸)₂, —S(O)(OR⁸)₂, an amino acid, a peptide, a carbohydrate, a nucleoside, or a co-antioxidant.

2. A pharmaceutical composition comprising:
a therapeutically effective amount of a one or more carotenoid analogs or derivatives; and
a therapeutically effective amount of at least one additional non-carotenoid medicament or composition suitable for the treatment of a disorder associated with platelet aggregation wherein the carotenoid analog or derivative has the structure

102

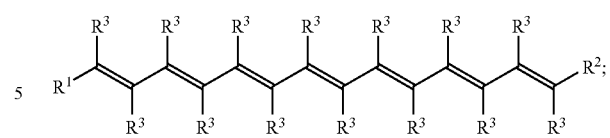

where each R³ is independently hydrogen or methyl, and where R¹ and R² are each independently:

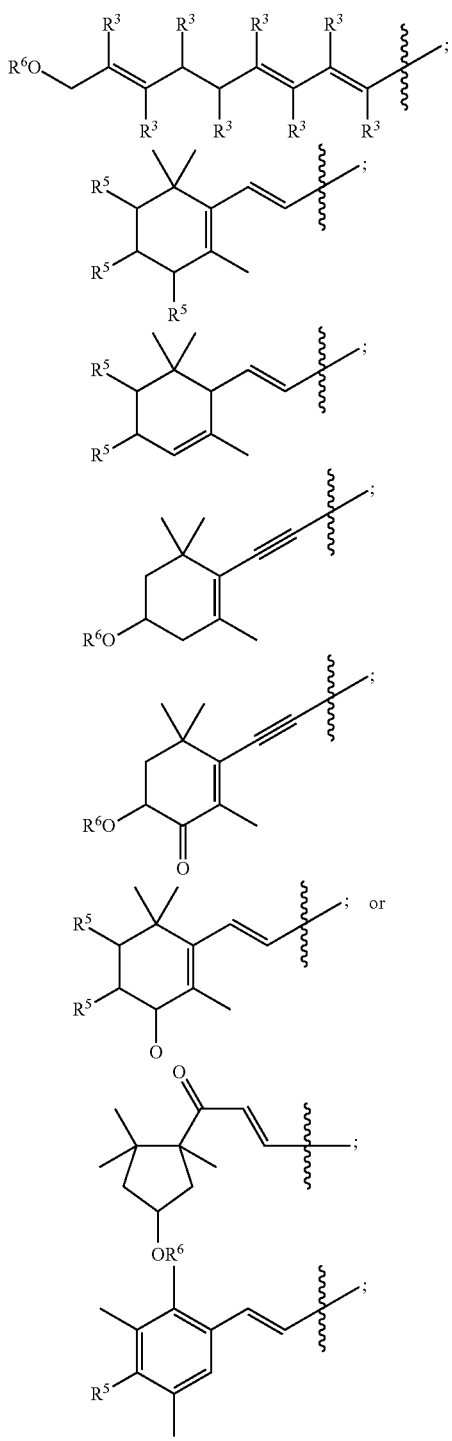

103

-continued

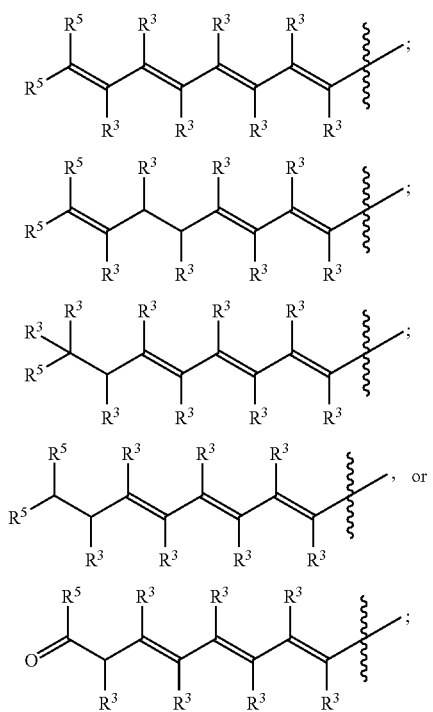

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-$N(R^7)_2$; -aryl-$N(R^7)_2$; -alkyl-$N^+(R^7)_3$; -aryl-$N^+(R^7)_3$; -alkyl-$CO_2R^9$; -aryl-$CO_2R^9$; -alkyl-$CO_2^-$; -aryl-$CO_2^-$; —C(O)-alkyl-$N(R^7)_2$; —C(O)-aryl-$N(R^7)_2$; —C(O)-alkyl-$N^+(R^7)_3$; —C(O)-aryl-$N^+(R^7)_3$; —C(O)-alkyl-$CO_2R^9$; —C(O)-aryl-$CO_2R^9$; -C(O)-alkyl-$CO_2^-$; —C(O)-aryl-$CO_2^-$; —C(O)—($NR^7$)-alkyl-$N(R^7)_2$; —C(O)—($NR^7$)-aryl-$N(R^7)_2$; —C(O)—($NR^7$)-alkyl-$N^+(R^7)_3$; —C(O)—($NR^7$)-aryl-$N^+(R^7)_3$; —C(O)—($NR^7$)-alkyl-$CO_2R^9$; —C(O)—($NR^7$)-aryl-$CO_2R^9$; —C(O)—($NR^7$)-alkyl-$CO_2^-$; —C(O)—($NR^7$)-aryl-$CO_2^-$; —C(O)—($NR^7$)-alkyl-$N(R^7)$-alkyl-$N(R^7)_2$; —C(O)—$OR^8$; —P(O)($OR^8$)$_2$; —S(O)($OR^8$)$_2$; —C(O)—[$C_6$-$C_{24}$ saturated hydrocarbon]; —C(O)—[$C_6$-$C_{24}$ monounsaturated hydrocarbon]; —C(O)—[$C_6$-$C_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)($OR^8$)$_2$, —S(O)($OR^8$)$_2$, an amino acid, a peptide, a carbohydrate, a nucleoside, or a co-antioxidant.

3. The composition of claim 2, wherein the carotenoid analog or derivative has the structure

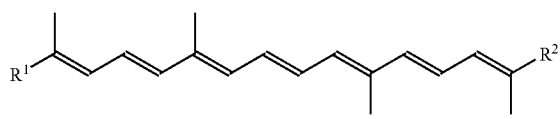

104 where each $R^1$ and $R^2$ are independently:

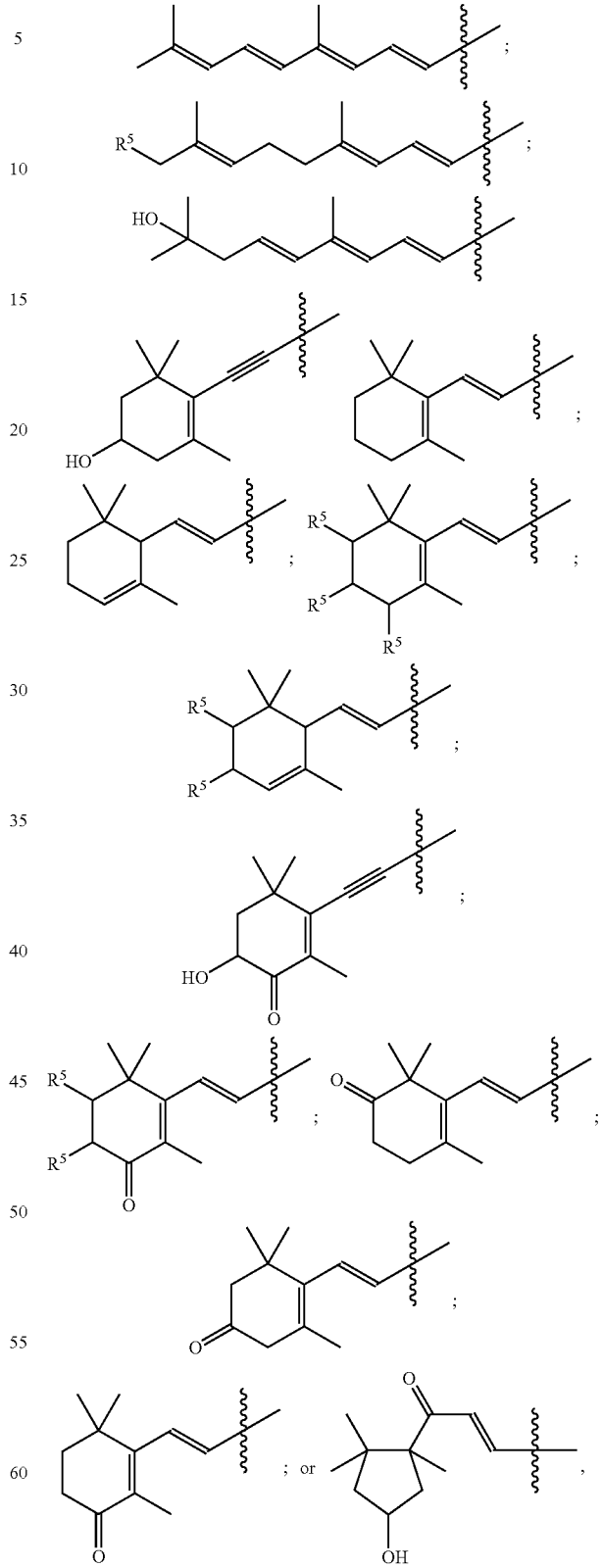

where $R^4$ is hydrogen, methyl, or —$CH_2OH$; and where each $R^5$ is independently hydrogen or —OH.

4. The composition of claim 2, wherein the carotenoid analog or derivative has the structure

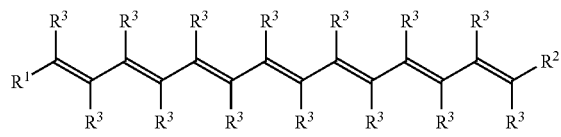

where each $R^3$ is independently hydrogen or methyl, and where each $R^1$ and $R^2$ are independently:

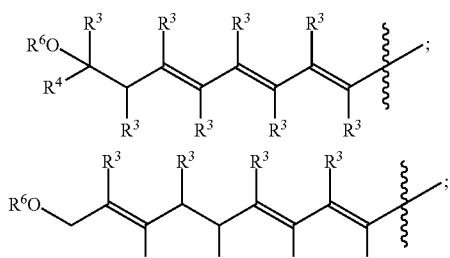

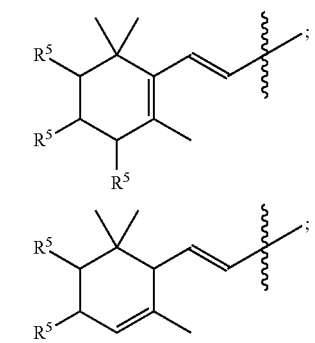

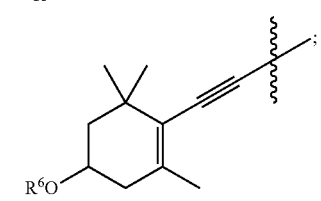

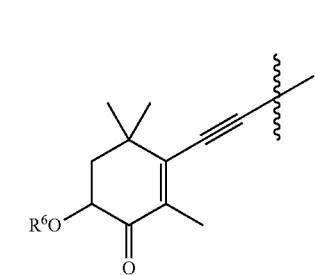

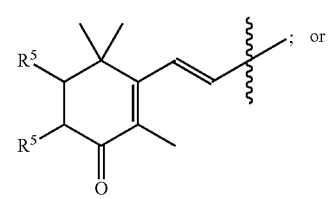

-continued

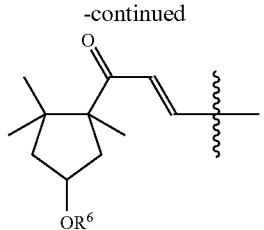

where $R^4$ is hydrogen or methyl; where each $R^5$ is independently hydrogen, —OH, or —OR$^6$ wherein at least one $R^5$ group is —OR$^6$; wherein each $R^6$ is independently: alkyl; aryl; -alkyl-N(R$^7$)$_2$; -aryl-N(R$^7$)$_2$; -alkyl-CO$_2$H; -aryl-CO$_2$H; —O—C(O)—R$^8$; —P(O)(OR$^8$)$_2$; —S(O)(OR$^8$)$_2$; an amino acid; a peptide, a carbohydrate; —C(O)—(CH$_2$)$_n$—CO$_2$R$^9$; a nucleoside reside, or a co-antioxidant; where $R^7$ is hydrogen, alkyl, or aryl; wherein $R^8$ is hydrogen, alkyl, aryl, benzyl or a con-antioxidant; where $R^9$ is hydrogen; alkyl; aryl; —P(O)(OR$^8$)$_2$; —S(O)(OR$^8$)$_2$; an amino acid; a peptide, a carbohydrate; a nucleoside, or a co-antioxidant; and where n is 1 to 9.

5. The composition of claim 2, wherein the carotenoid analog or derivative has the structure

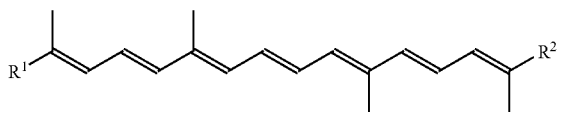

where each $R^1$ and $R^2$ are independently:

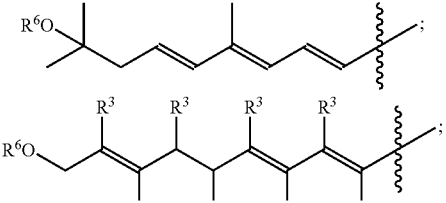

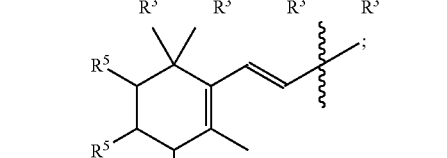

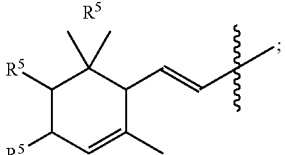

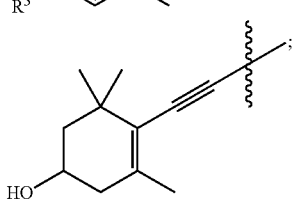

-continued

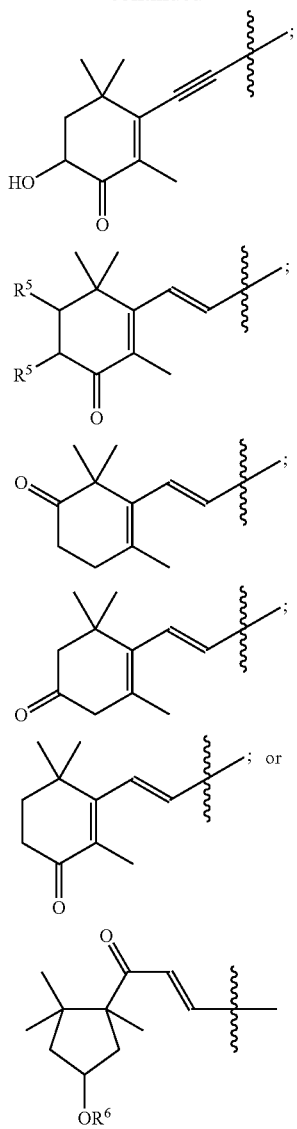

where each R[5] is independently hydrogen, —OH, or —OR[6] wherein at least one R[5] group is —OR[6]; wherein each R[6] is independently: alkyl; aryl; -alkyl-N(R[7])$_2$; -aryl-N(R[7])$_2$; -alkyl-CO$_2$H; -aryl-CO$_2$H; —O—C(O)—R[8]; —P(O)(OR[8])$_2$; —S(O)(OR[8])$_2$; an amino acid; a peptide, a carbohydrate; —C(O)—(CH$_2$)$_n$—CO$_2$R[9]; a nucleoside reside, or a co-antioxidant; where R[7] is hydrogen, alkyl, or aryl; wherein R[8] is hydrogen, alkyl, aryl, benzyl, or a co-antioxidant; and where R[9] is hydrogen; alkyl; aryl; —P(O)(OR[8])$_2$; —S(O)(OR[8])$_2$; an amino acid; a peptide, a carbohydrate; a nucleoside, or a co-antioxidant; and where n is 1 to 9.

6. The composition of claim 2, where each —OR[6] is independently

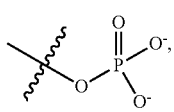

-continued

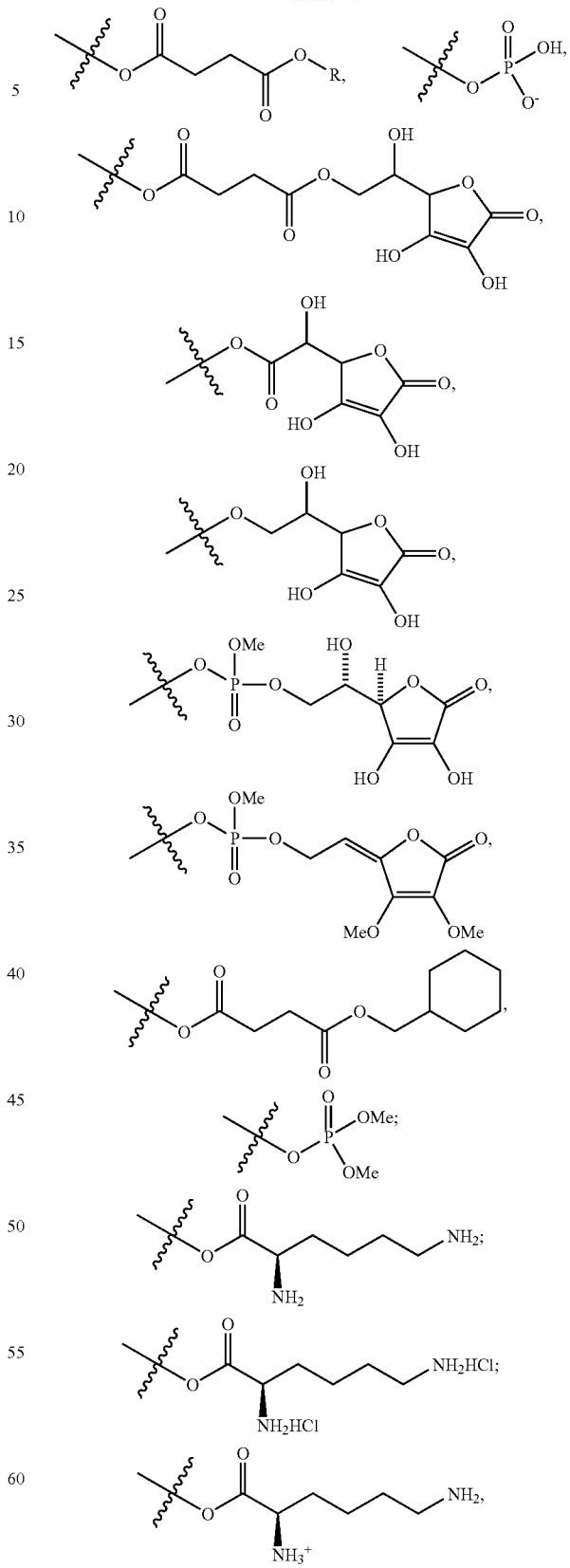

and wherein each R is independently H, alkyl, aryl, benzyl, Group IA metal, or co-antioxidant.

7. The composition of claim 6, where each —OR$^6$ is independently

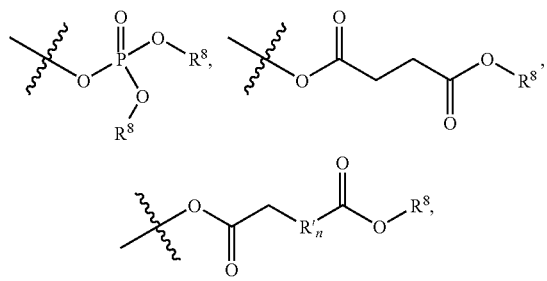

or a co-antioxidant; wherein R$^8$ is hydrogen, alkyl, aryl, benzyl, Group IA metal, or a co-antioxidant; wherein R' is CH$_2$; and wherein n is 1 to 9.

8. The composition of claim 6, where each —OR$^6$ is independently

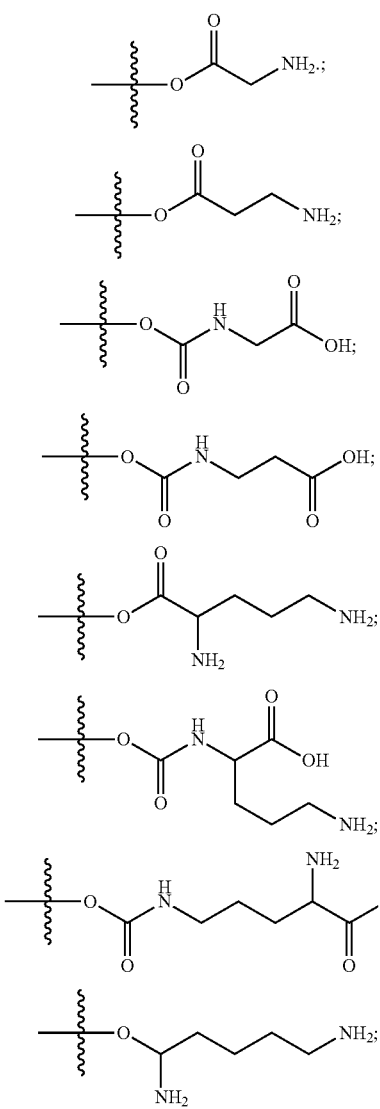

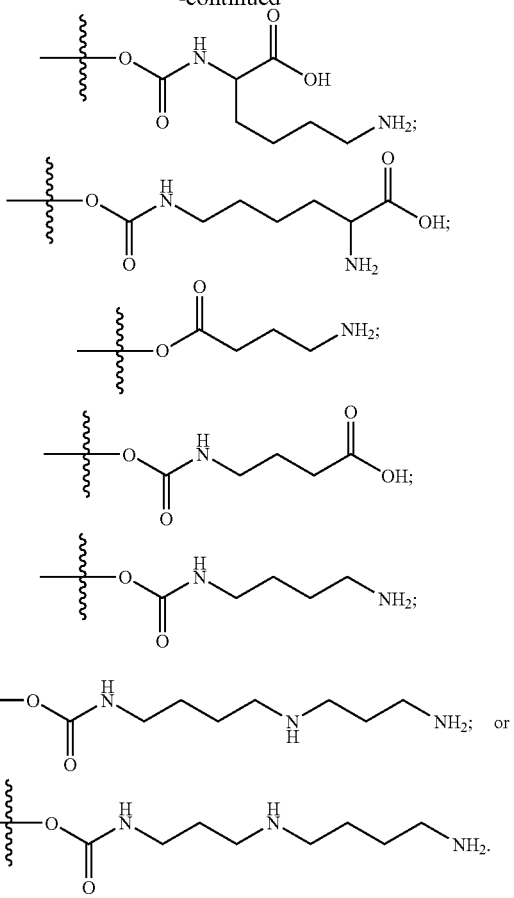

9. The composition of claim 2, wherein the carotenoid analog or derivative has the structure

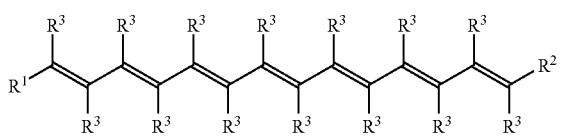

wherein each R$^3$ is independently hydrogen or methyl, and wherein each R$^1$ and R$^2$ are independently:

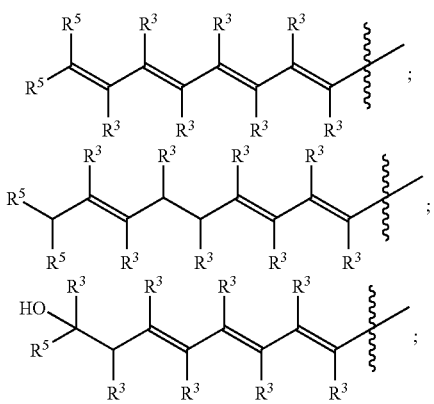

111

-continued

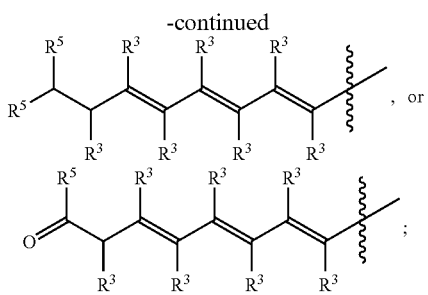

where each $R^5$ is independently hydrogen, —OH, —CH$_2$OH, or —OR$^6$, wherein at least one $R^5$ group is —OR$^6$; wherein each $R^5$ is independently: alkyl; aryl; —P(O)(OR$^8$)$_2$; an amino acid; a peptide, a carbohydrate; —C(O)—(CH$_2$)$_n$—CO$_2$R$^9$; a nucleoside residue, or a co-antioxidant; wherein $R^8$ is hydrogen, alkyl, aryl, benzyl or a co-antioxidant; wherein $R^9$ is hydrogen; alkyl; aryl; —P(O)(OR$^8$)$_2$; an amino acid; a peptide, a carbohydrate; a nucleoside, or a co-antioxidant; and wherein n is 1 to 9

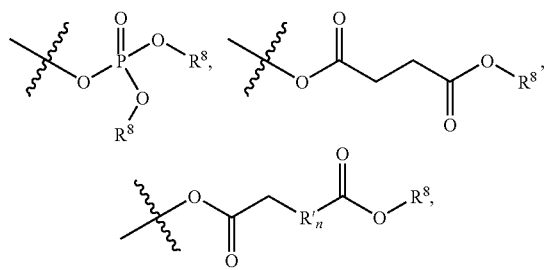

or a co-antioxidant; wherein $R^8$ is hydrogen, alkyl, aryl, benzyl, Group IA metal, or a co-antioxidant; wherein R' is CH$_2$; and wherein n is 1 to 9.

10. The composition of claim 2, wherein non-carotenoid medicament or composition suitable for the treatment of a disorder associated with platelet aggregation comprises one or more anticoagulants.

11. The composition of claim 10, wherein said anticoagulants comprise aspirin.

12. The composition of claim 2, wherein non-carotenoid medicament or composition suitable for the treatment of a disorder associated with platelet aggregation comprises one or more non-fractionated or fractionated heparins.

13. The composition of claim 2, wherein non-carotenoid medicament or composition suitable for the treatment of a disorder associated with platelet aggregation comprises one or more statins.

14. The composition of claim 13, wherein said statins comprise simvastatin.

15. The composition of claim 2, wherein non-carotenoid medicament or composition suitable for the treatment of a disorder associated with platelet aggregation comprises one or more ADP receptor inhibitors.

16. The composition of claim 15, wherein said ADP receptor inhibitors comprise clopidogrel.

17. The composition of claim 2, wherein non-carotenoid medicament or composition suitable for the treatment of a disorder associated with platelet aggregation comprises one or more thrombin inhibitors.

18. The composition of claim 2, wherein non-carotenoid medicament or composition suitable for the treatment of a disorder associated with platelet aggregation comprises one or more factor Xa inhibitors.

19. The composition of claim 2, wherein non-carotenoid medicament or composition suitable for the treatment of a disorder associated with platelet aggregation comprises one or more agonists of purinergic receptors.

20. The composition of claim 2, wherein non-carotenoid medicament or composition suitable for the treatment of a disorder associated with platelet aggregation comprises one or more antagonists of CD40 or CD40 ligand (CD40L) or compounds that disrupt the interaction of CD40 and CD40L.

21. The composition of claim 2, wherein non-carotenoid medicament or composition suitable for the treatment of a disorder associated with platelet aggregation comprises one or more PGE1 agonists, PG synthase inhibitors, TX synthase inhibitors, and TXA2 antagonists); glycoprotein IIb/IIIa antagonists, and any combination thereof.

22. The composition of claim 2, further comprising one or more pharmaceutically acceptable carriers.

23. A method of treating a disorder associated with platelet aggregation in a subject comprising administering to a subject who would benefit from such treatment a pharmaceutical composition comprising:

a therapeutically effective amount of a one or more carotenoid analogs or derivatives; and a therapeutically effective amount of at least one additional non-carotenoid medicament or composition suitable for the treatment of a disorder associated with platelet aggregation wherein the carotenoid analog or derivative has the structure

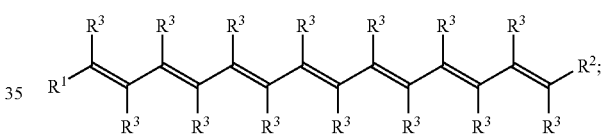

where each $R^3$ is independently hydrogen or methyl, and where $R^1$ and $R^2$ are each independently:

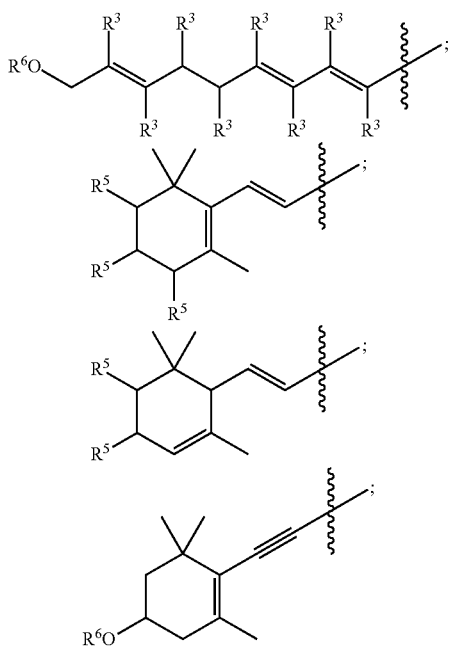

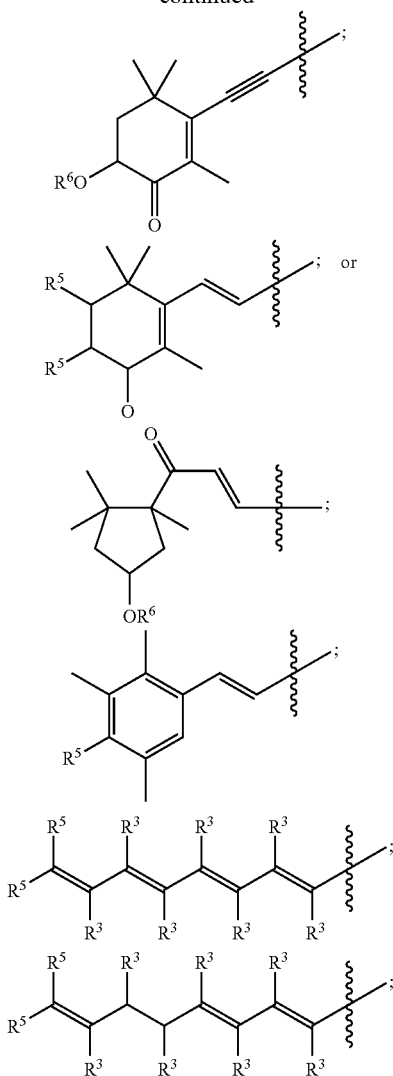

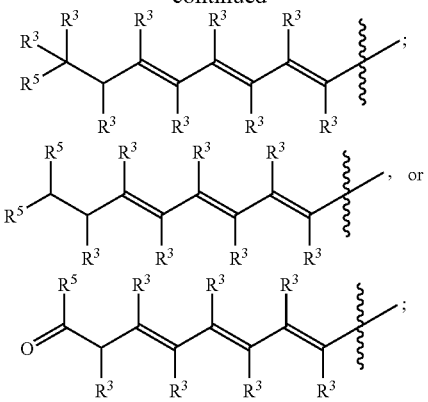

where each $R^5$ is independently hydrogen, —$CH_3$, —OH, —$CH_2OH$ or —$OR^6$ wherein at least one $R^5$ group in the carotenoid analog or derivative is —$OR^6$; wherein each $R^6$ is independently: H; alkyl; aryl; -alkyl-N($R^7$)$_2$; -aryl-N($R^7$)$_2$; -alkyl-N$^+$($R^7$)$_3$; -aryl-N$^+$($R^7$)$_3$; -alkyl-CO$_2$R$^9$; -aryl-CO$_2$R$^9$; -alkyl-CO$_2^-$; -aryl-CO$_2^-$; —C(O)-alkyl-N($R^7$)$_2$; —C(O)-aryl-N($R^7$)$_2$; —C(O)-alkyl-N$^+$($R^7$)$_3$; —C(O)-aryl-N$^+$($R^7$)$_3$; —C(O)-alkyl-CO$_2$R$^9$; —C(O)-aryl-CO$_2$R$^9$; —C(O)-alkyl-CO$_2^-$; —C(O)-aryl-CO$_2^-$; —C(O)—(NR$^7$)-alkyl-N(R$^7$)$_2$; —C(O)—(NR$^7$)-aryl-N(R$^7$)$_2$; —C(O)—(NR$^7$)-alkyl-N$^+$(R$^7$)$_3$; —C(O)—(NR$^7$)-aryl-N$^+$(R$^7$)$_3$; —C(O)—(NR$^7$)-alkyl-CO$_2$R$^9$; —C(O)—(NR$^7$)-aryl-CO$_2$R$^9$; —C(O)—(NR$^7$)-alkyl-CO$_2^-$; —C(O)—(NR$^7$)-aryl-CO$_2^-$; —C(O)—(NR$^7$)-alkyl-N(R$^7$)-alkyl-N(R$^7$)$_2$; —C(O)—OR$^8$; —P(O)(OR$^8$)$_2$; —S(O)(OR$^8$)$_2$; —C(O)—[C$_6$-C$_{24}$ saturated hydrocarbon]; —C(O)—[C$_6$-C$_{24}$ monounsaturated hydrocarbon]; —C(O)—[C$_6$-C$_{24}$ polyunsaturated hydrocarbon]; a peptide; a carbohydrate; a nucleoside reside; or a co-antioxidant; where $R^7$ is hydrogen, alkyl, or aryl; where $R^8$ is hydrogen, alkyl, aryl, benzyl or a co-antioxidant; and where $R^9$ is hydrogen, alkyl, aryl, —P(O)(OR$^8$)$_2$, —S(O)(OR$^8$)$_2$, an amino acid, a peptide, a carbohydrate, a nucleoside, or a co-antioxidant.

\* \* \* \* \*